United States Patent [19]

Bird

[11] Patent Number: 5,007,420
[45] Date of Patent: Apr. 16, 1991

[54] VENTILATOR HAVING AN OSCILLATORY INSPIRATORY PHASE AND METHOD

[76] Inventor: Forrest M. Bird, P.O. Box 817, Sandpoint, Id. 83864

[21] Appl. No.: 145,734

[22] Filed: Jan. 14, 1988

Related U.S. Application Data

[63] Continuation of Ser. No. 671,491, Nov. 14, 1984, abandoned, which is a continuation-in-part of Ser. No. 516,133, Jul. 21, 1983, Pat. No. 4,592,349, which is a continuation-in-part of Ser. No. 291,622, Aug. 10, 1981, abandoned, which is a continuation-in-part of Ser. No. 269,929, Apr. 3, 1981, abandoned, and Ser. No. 250,586, Jun. 2, 1981, abandoned.

[51] Int. Cl.$^5$ .............................................. A61M 16/00
[52] U.S. Cl. ........................... 128/200.14; 128/203.14; 128/204.25; 128/205.24
[58] Field of Search ................ 128/200.11, 200.20, 128/200.21, 200.13, 204.18, 204.21, 204.23–204.25, 205.13, 205.18, 205.21, 205.24, 207.14, 207.16

[56] References Cited

U.S. PATENT DOCUMENTS

| | | | |
|---|---|---|---|
| 3,771,721 | 11/1973 | Van Amerongen | 128/200.21 |
| 3,923,055 | 12/1975 | Hammacher | 128/204.21 |
| 3,993,059 | 11/1976 | Sjostrand | 128/205.13 |
| 4,020,834 | 5/1977 | Bird | 128/204.25 |
| 4,060,078 | 11/1977 | Bird | 128/204.25 |
| 4,121,579 | 10/1978 | Bird | 128/204.26 |
| 4,127,123 | 11/1978 | Bird | 128/204.26 |
| 4,155,356 | 1/1979 | Venegas | 125/207.14 |
| 4,197,843 | 4/1980 | Bird | 128/204.26 |
| 4,215,681 | 5/1980 | Zalkin et al. | 128/204.21 |
| 4,265,237 | 5/1981 | Schwanbom et al. | 128/204.25 |
| 4,270,530 | 6/1981 | Baum et al. | 128/204.25 |
| 4,481,944 | 11/1984 | Bunnell | 128/204.18 |
| 4,592,349 | 6/1986 | Bird | 128/205.04 |

FOREIGN PATENT DOCUMENTS 2105594  3/1983  United Kingdom ........... 128/207.15

Primary Examiner—Randall L. Green
Assistant Examiner—K. M. Reichle
Attorney, Agent, or Firm—Flehr, Hohbach, Test, Albritton & Herbert

[57] ABSTRACT

Ventilator for use with a source of gas under pressure for supplying such gas to the airway of a patient having an inlet adapted to be connected to the source of gas, and an outlet adapted to be connected to the airway of the patient. A pneumatic oscillator is connected to the inlet for supplying pulsatile gas in the form of successive small volumes of gas to the airway of the patient during a breath of the patient to cause diffusive ventilation of the airway to the patient. An exhalation valve assembly is connected to the patient airway for permitting the patient to exhale gases introduced into the patient airway.

35 Claims, 27 Drawing Sheets

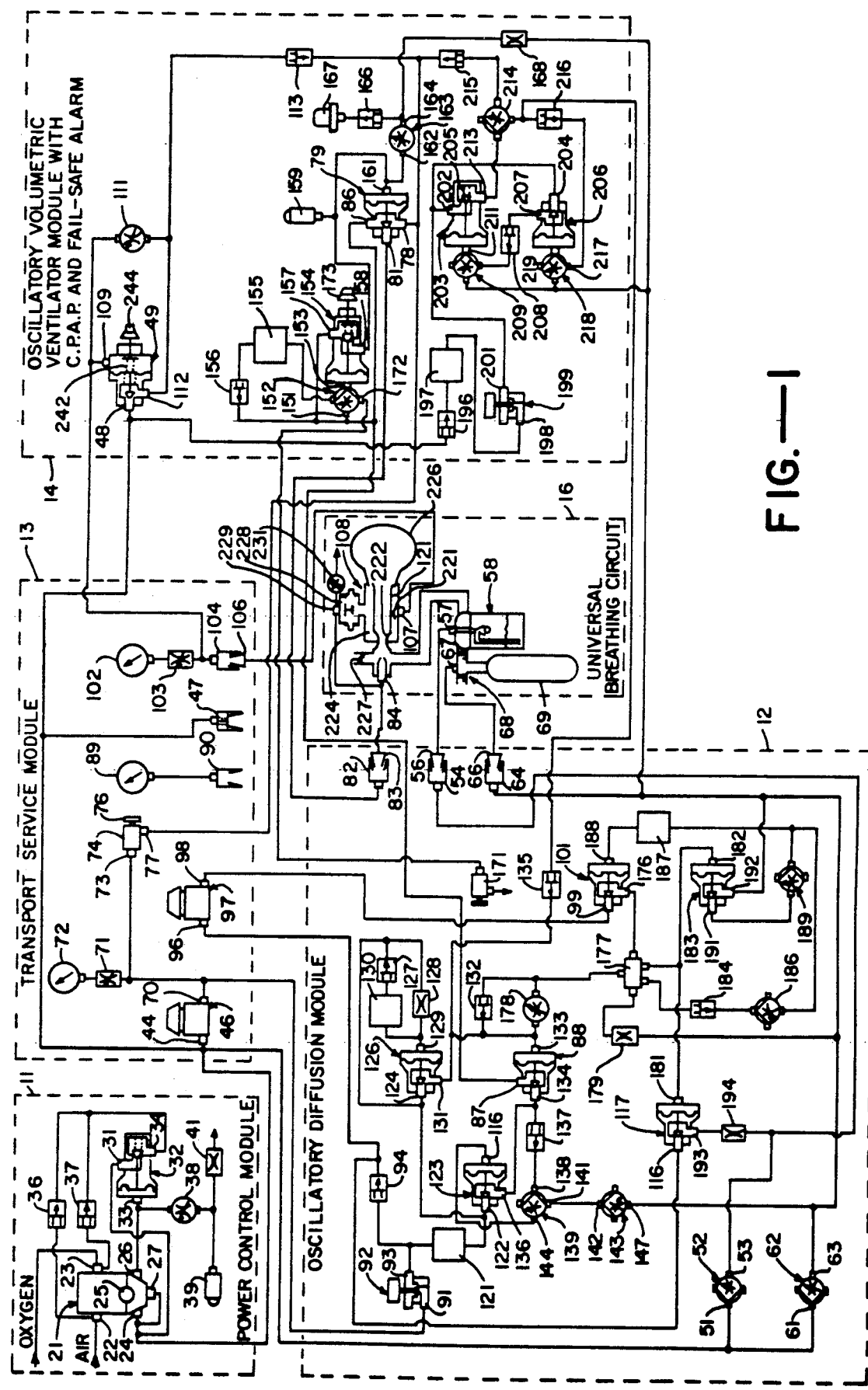
FIG.—1

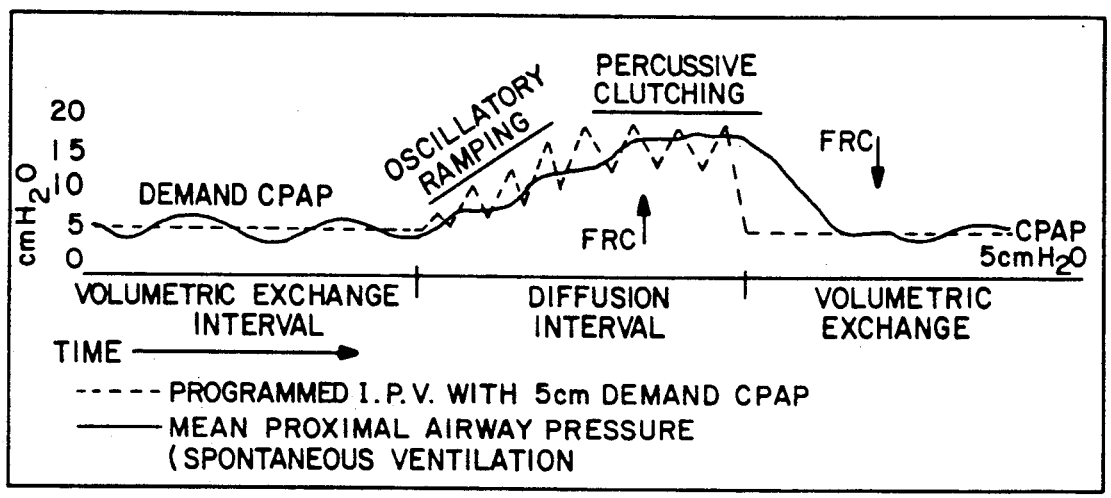
FIG.—2
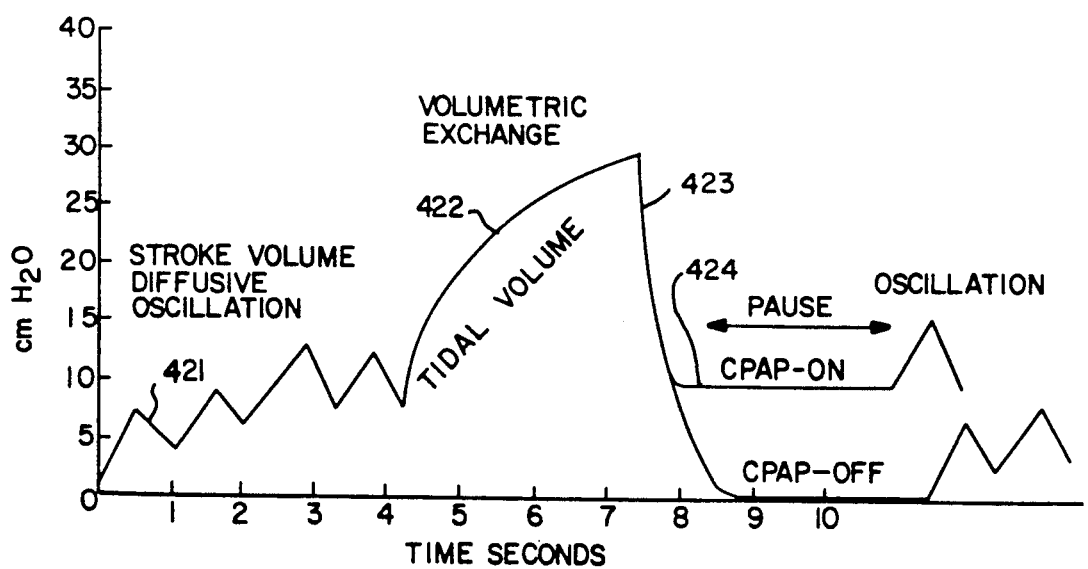
FIG.—4

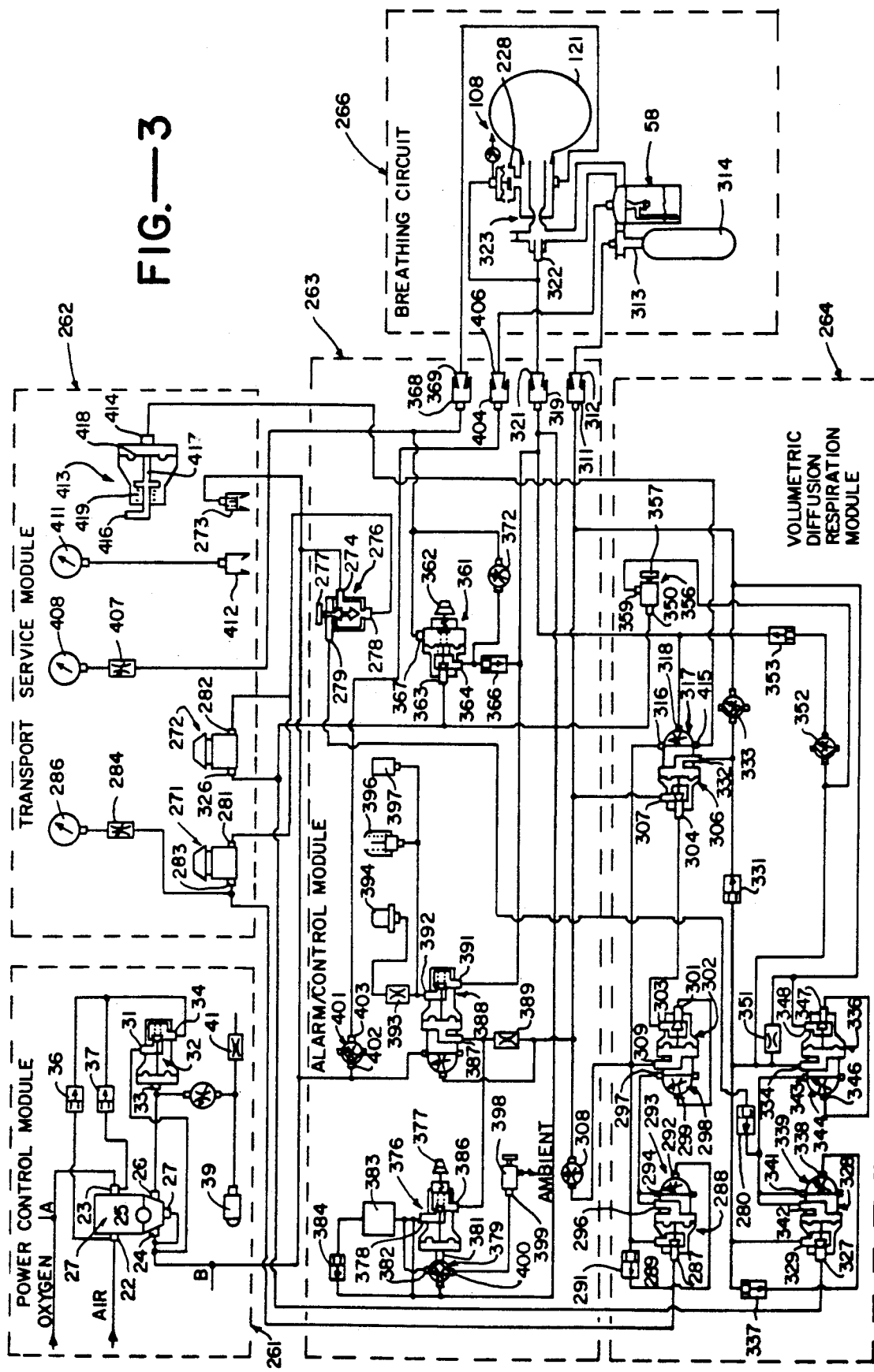

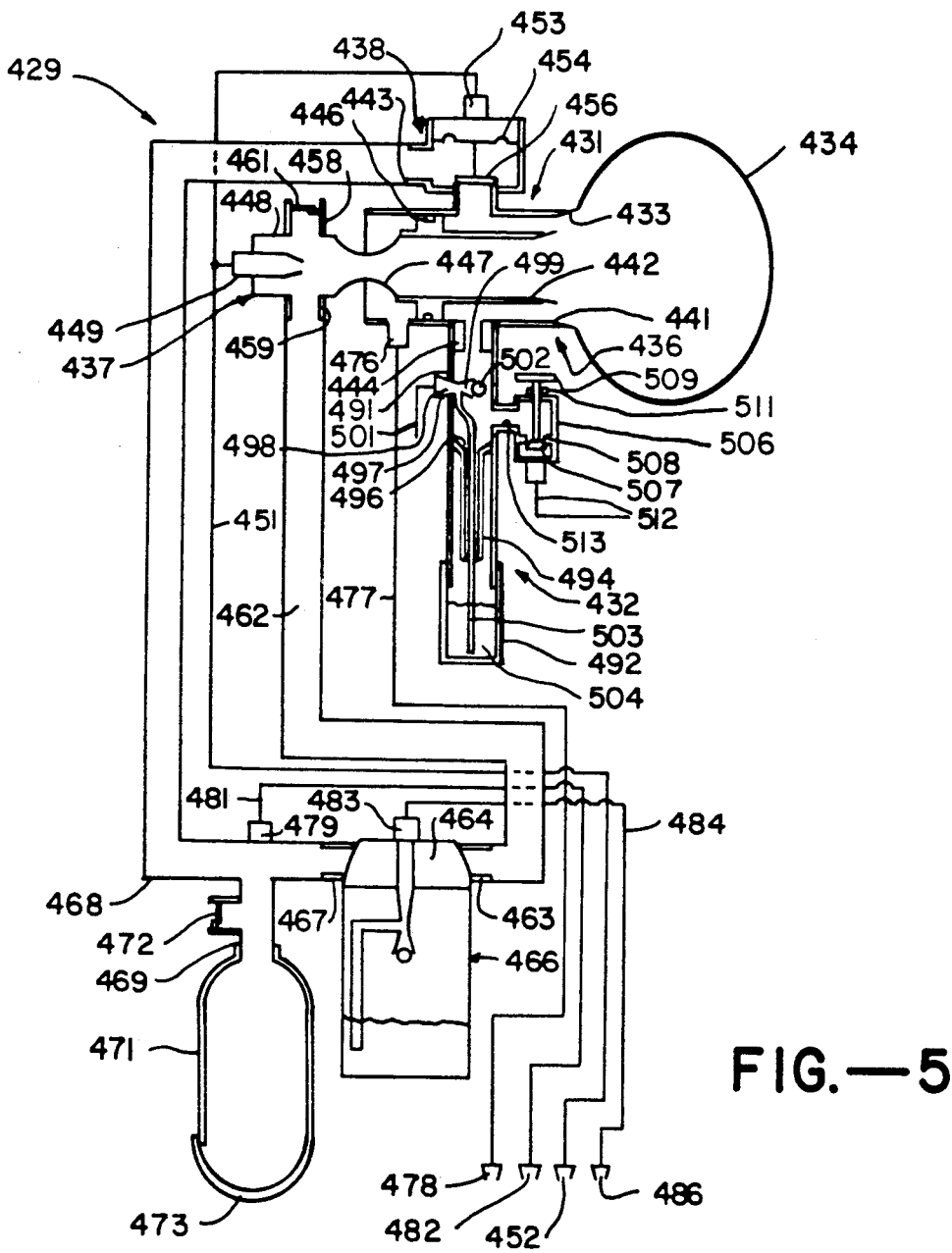
FIG.—5
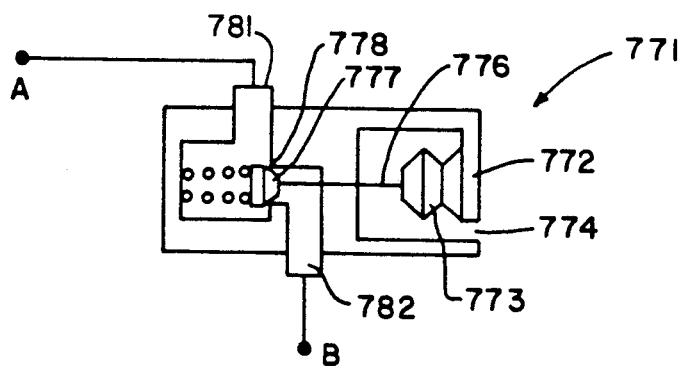
FIG.—8

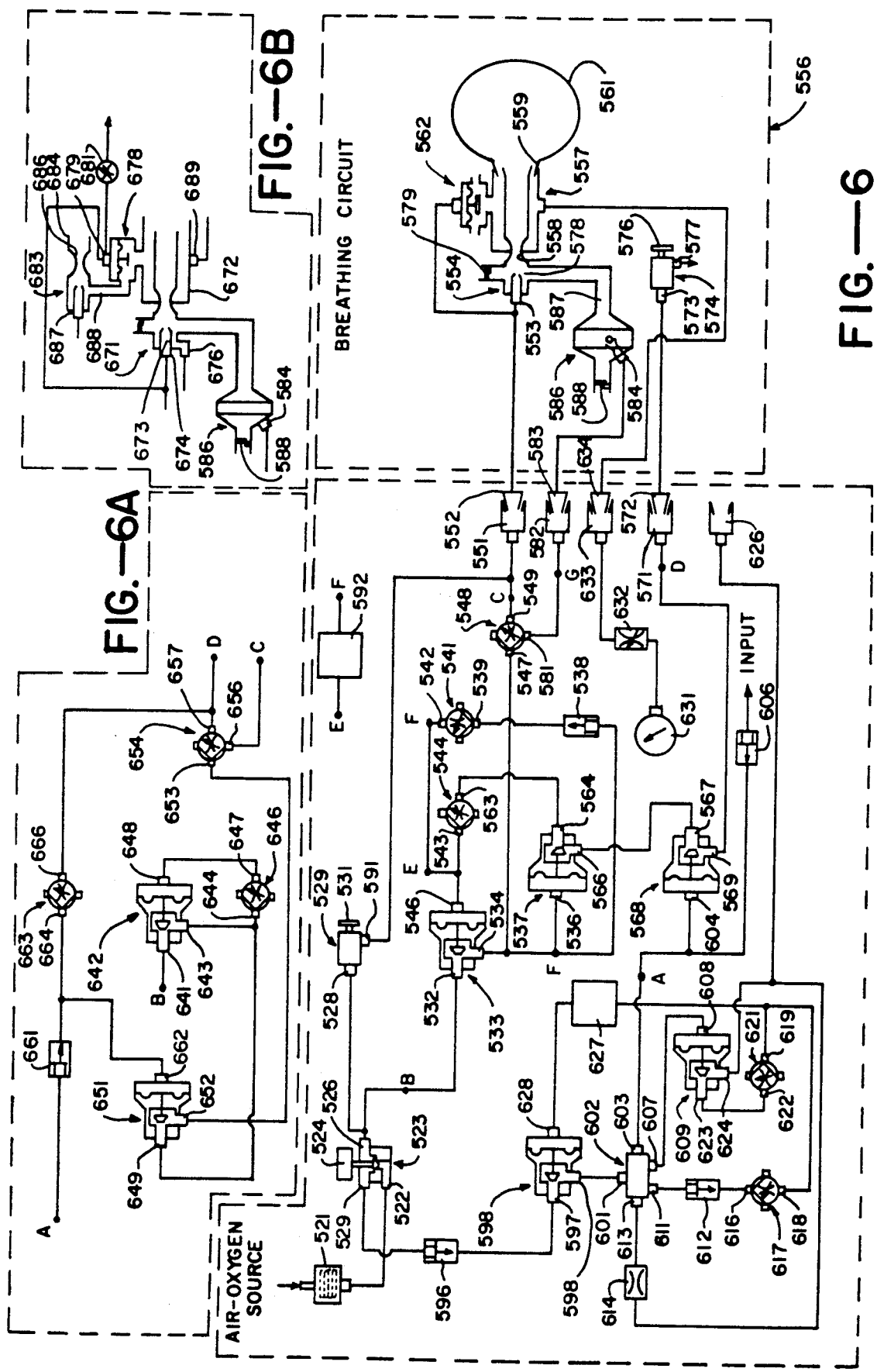

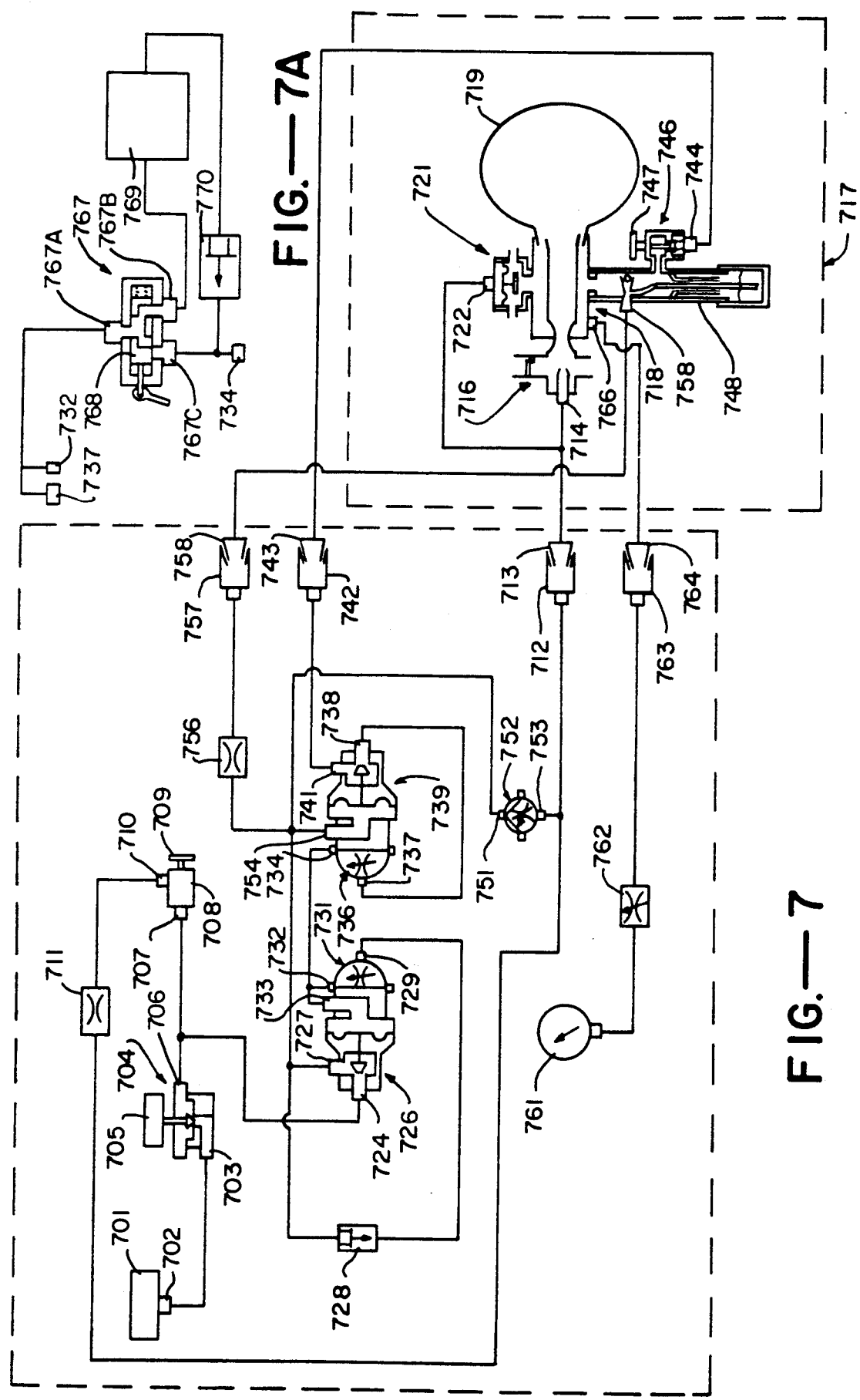

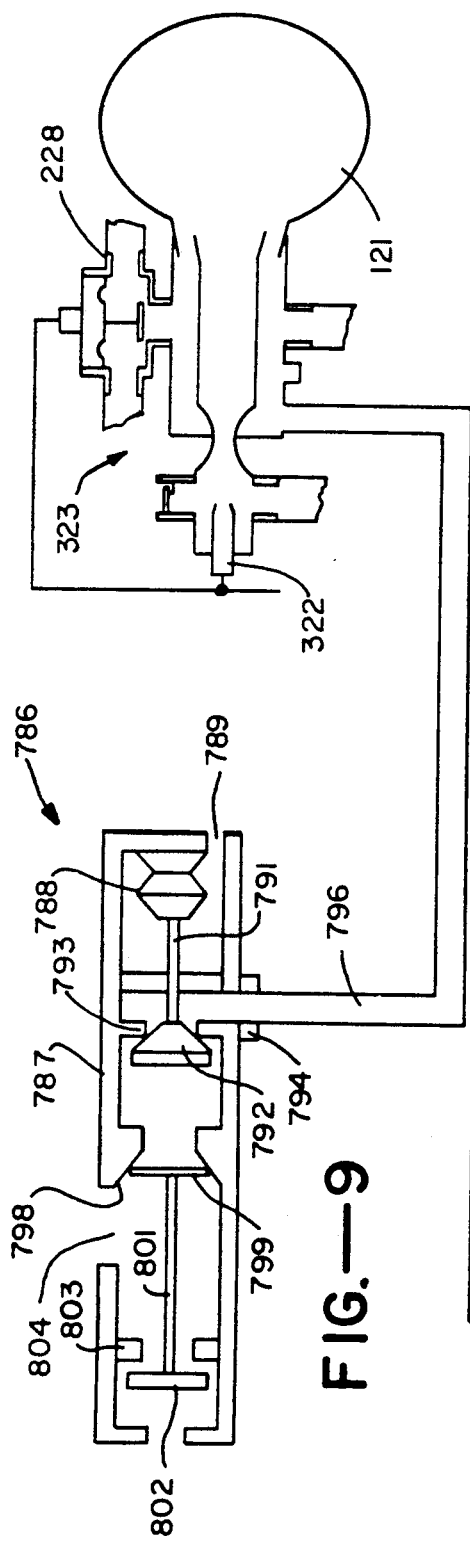
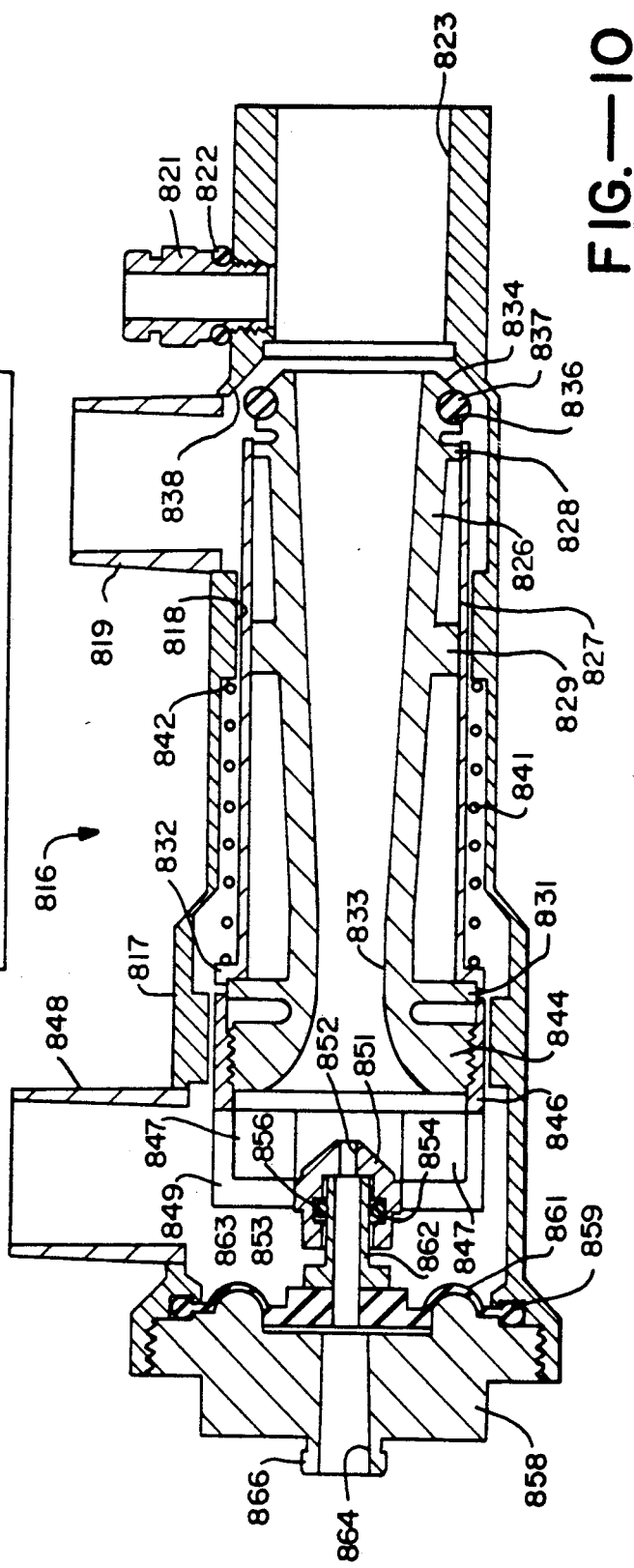
FIG.—9
FIG.—10

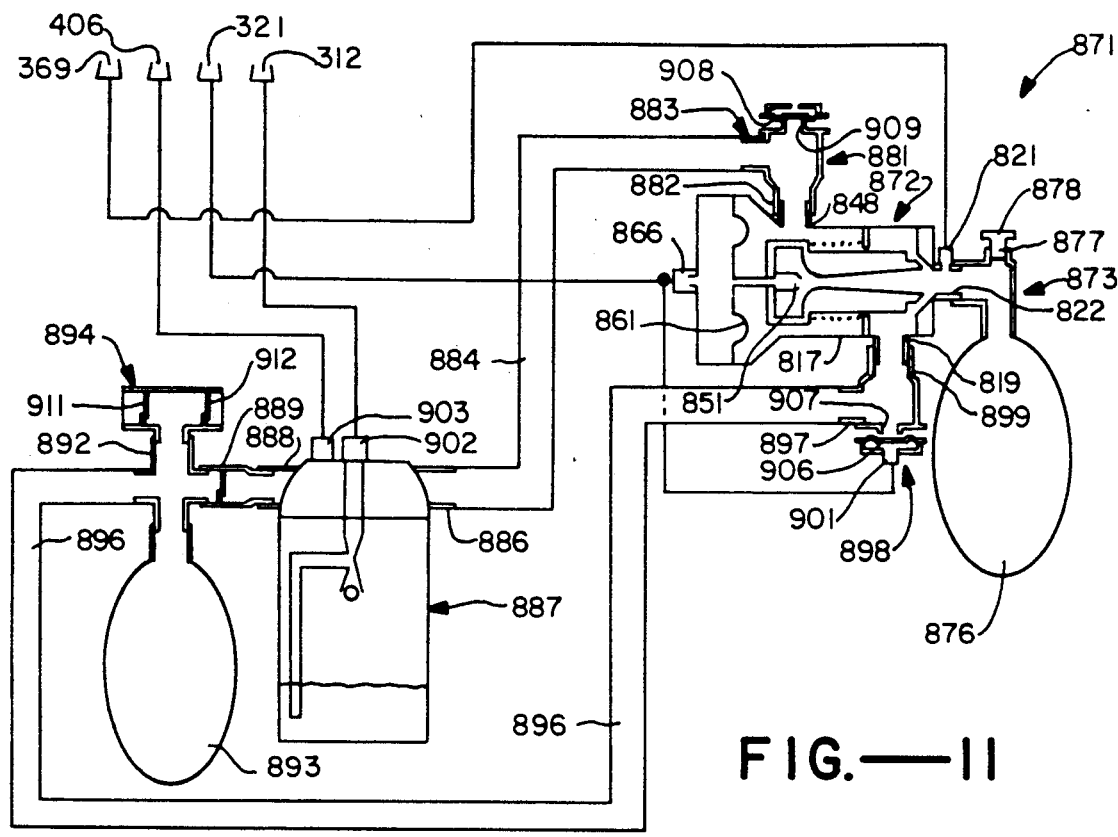
FIG.—11
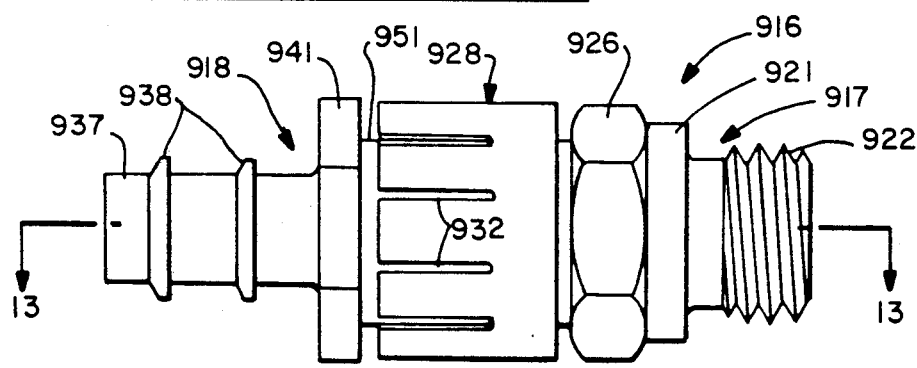
FIG.—12
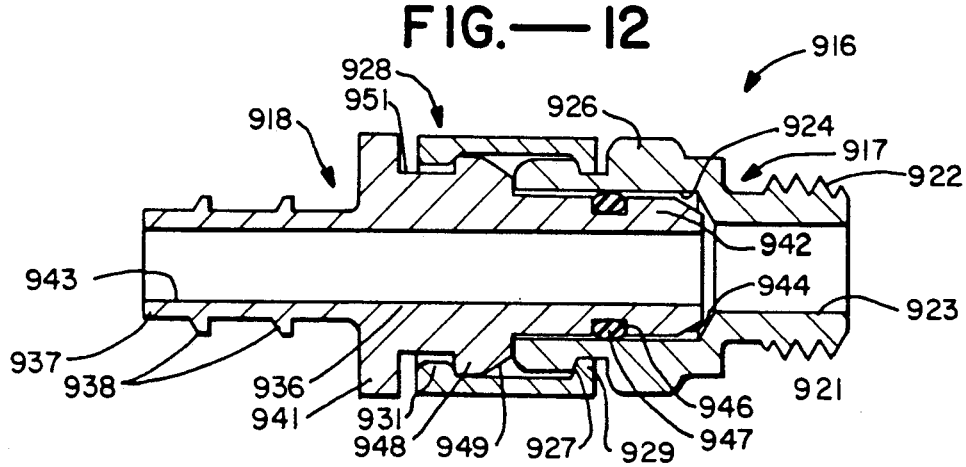
FIG.—13

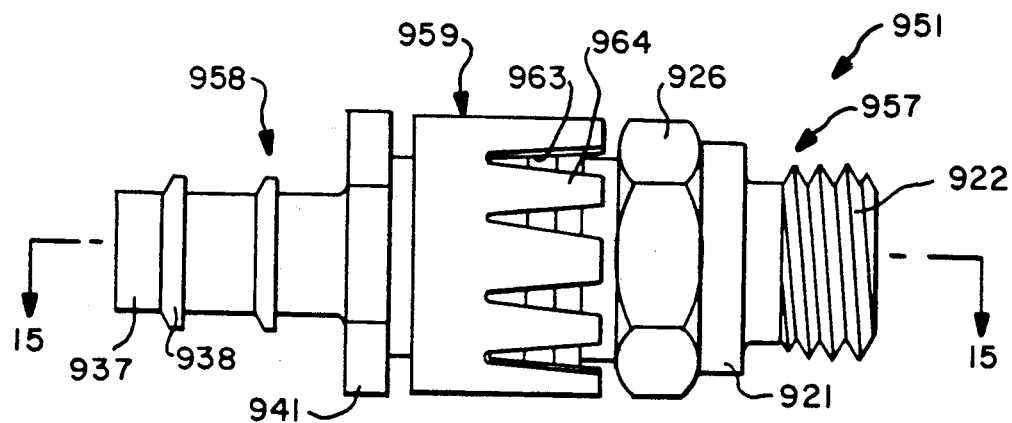
FIG.—14
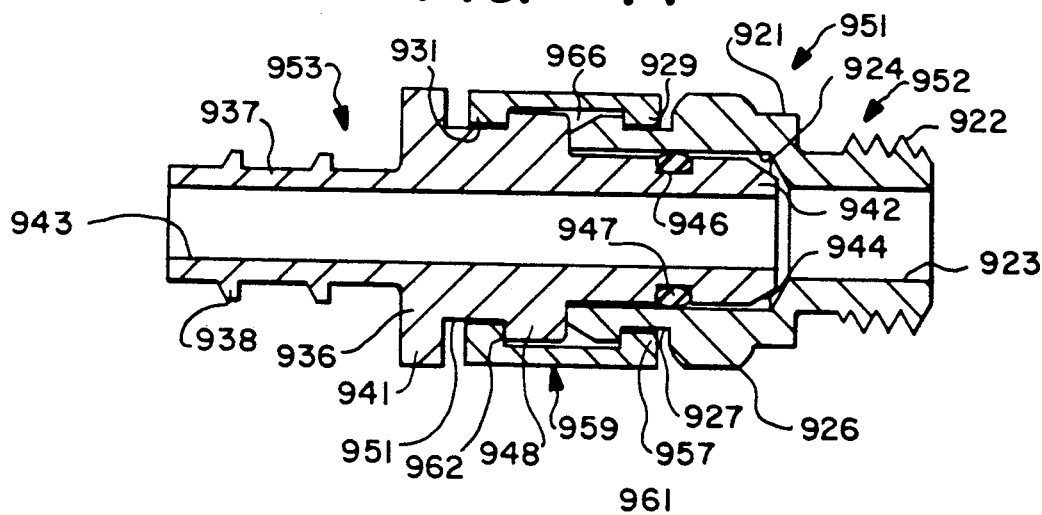
FIG.—15
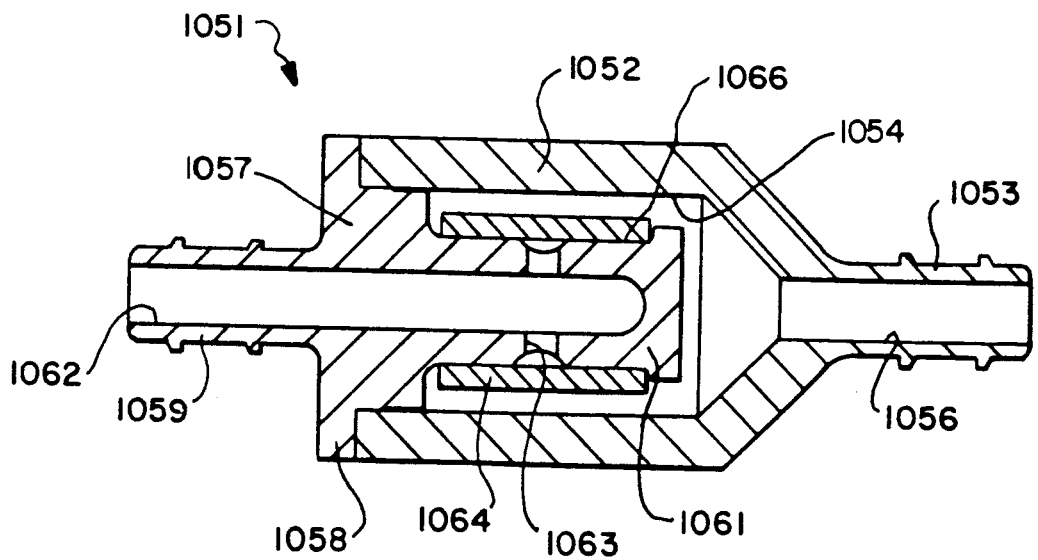
FIG.—19

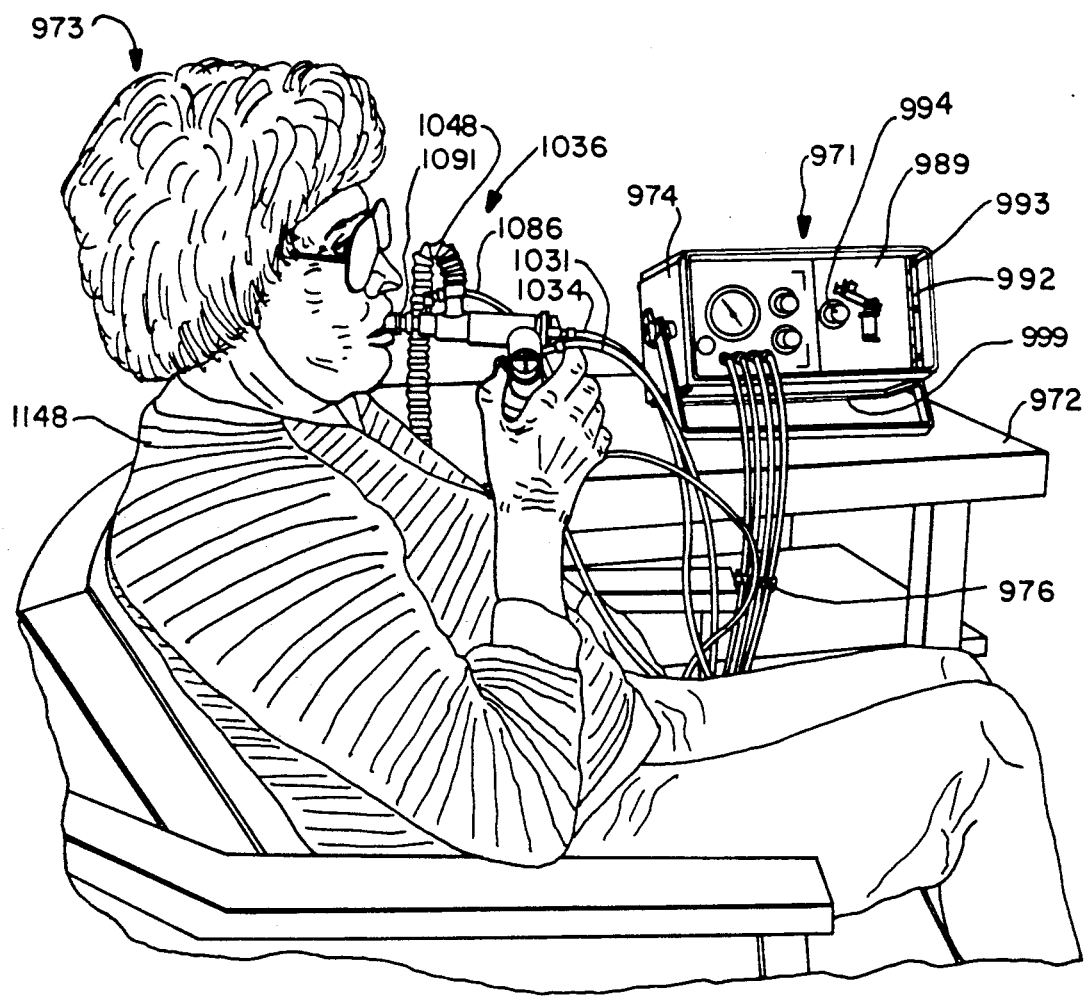
FIG.—16
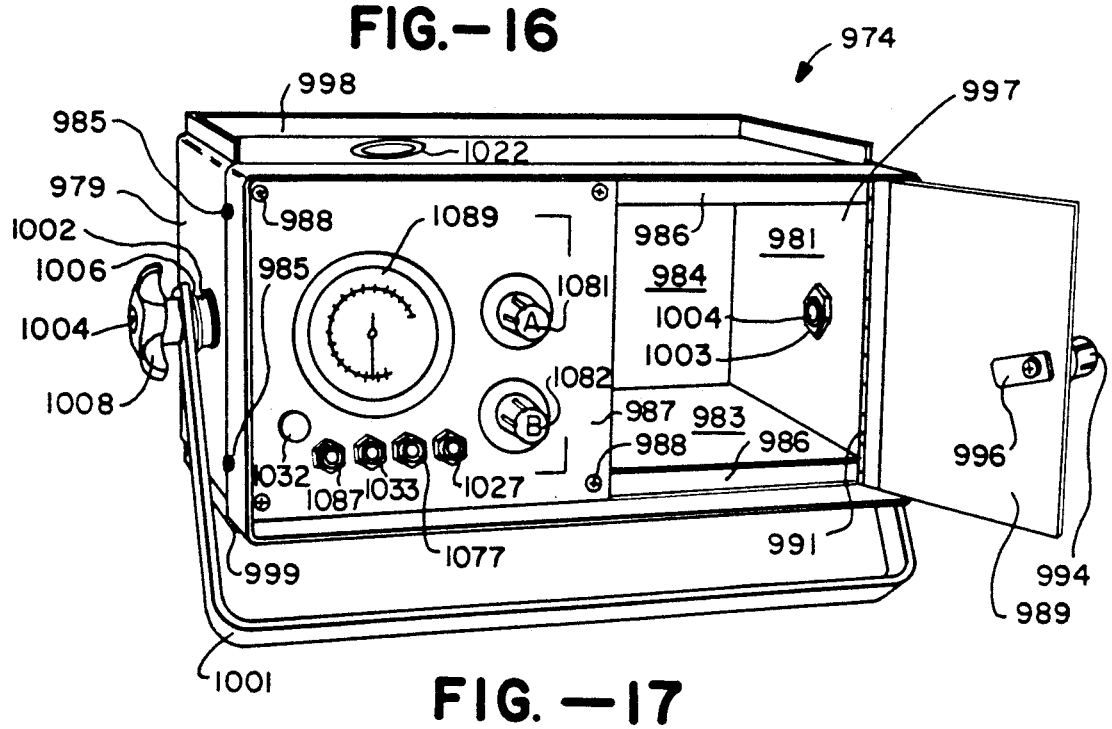
FIG.—17

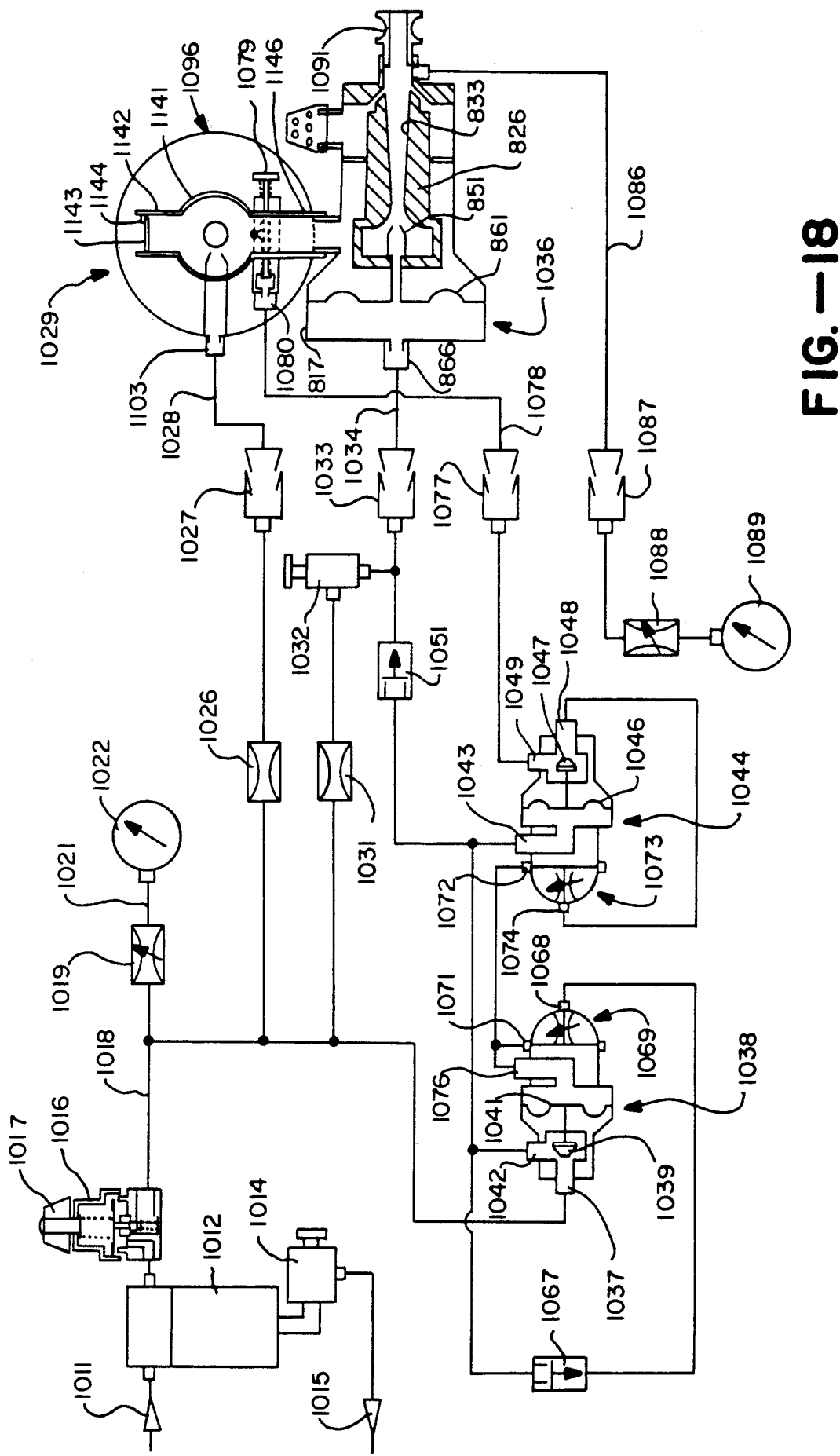
FIG.—18

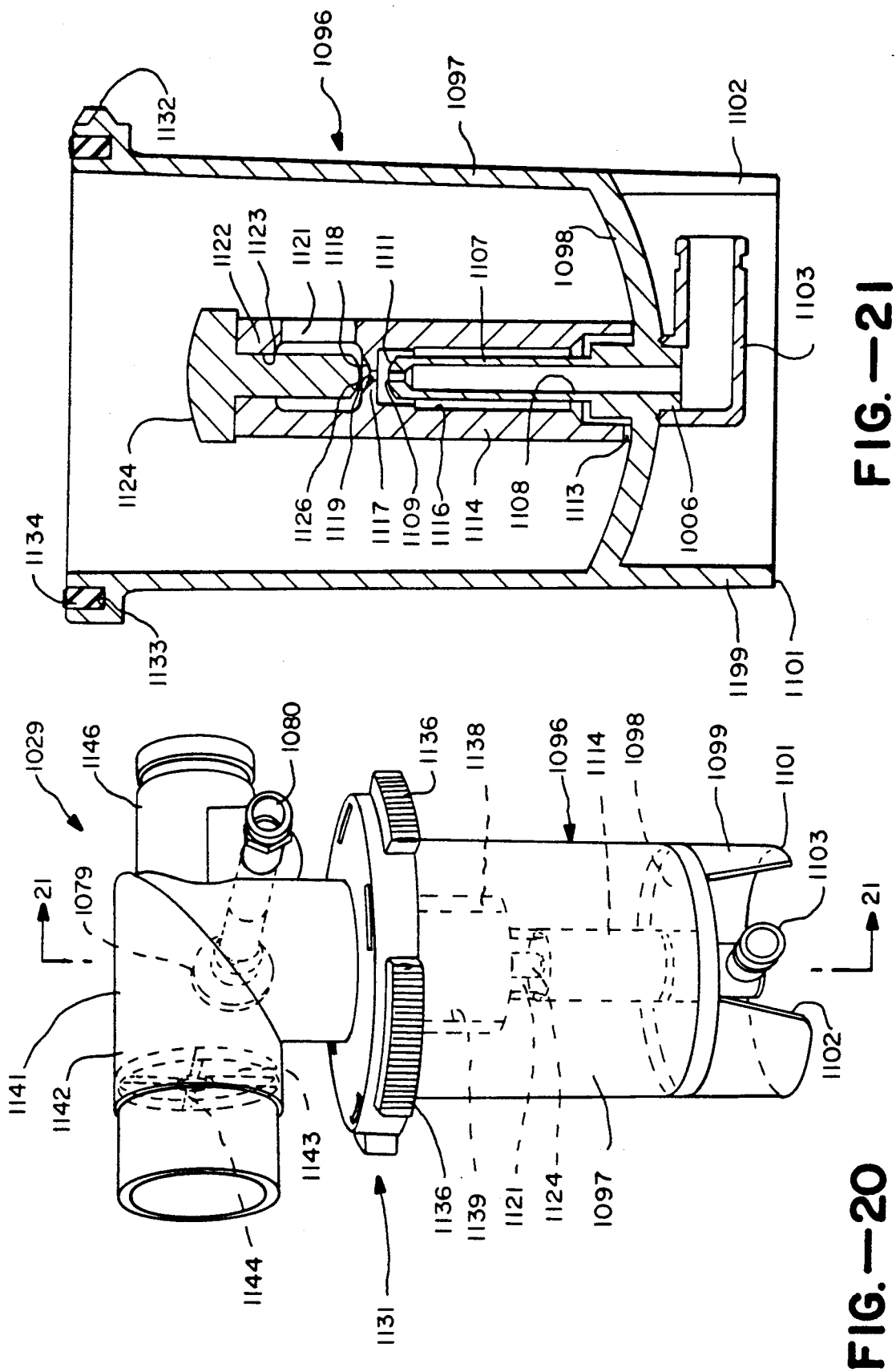

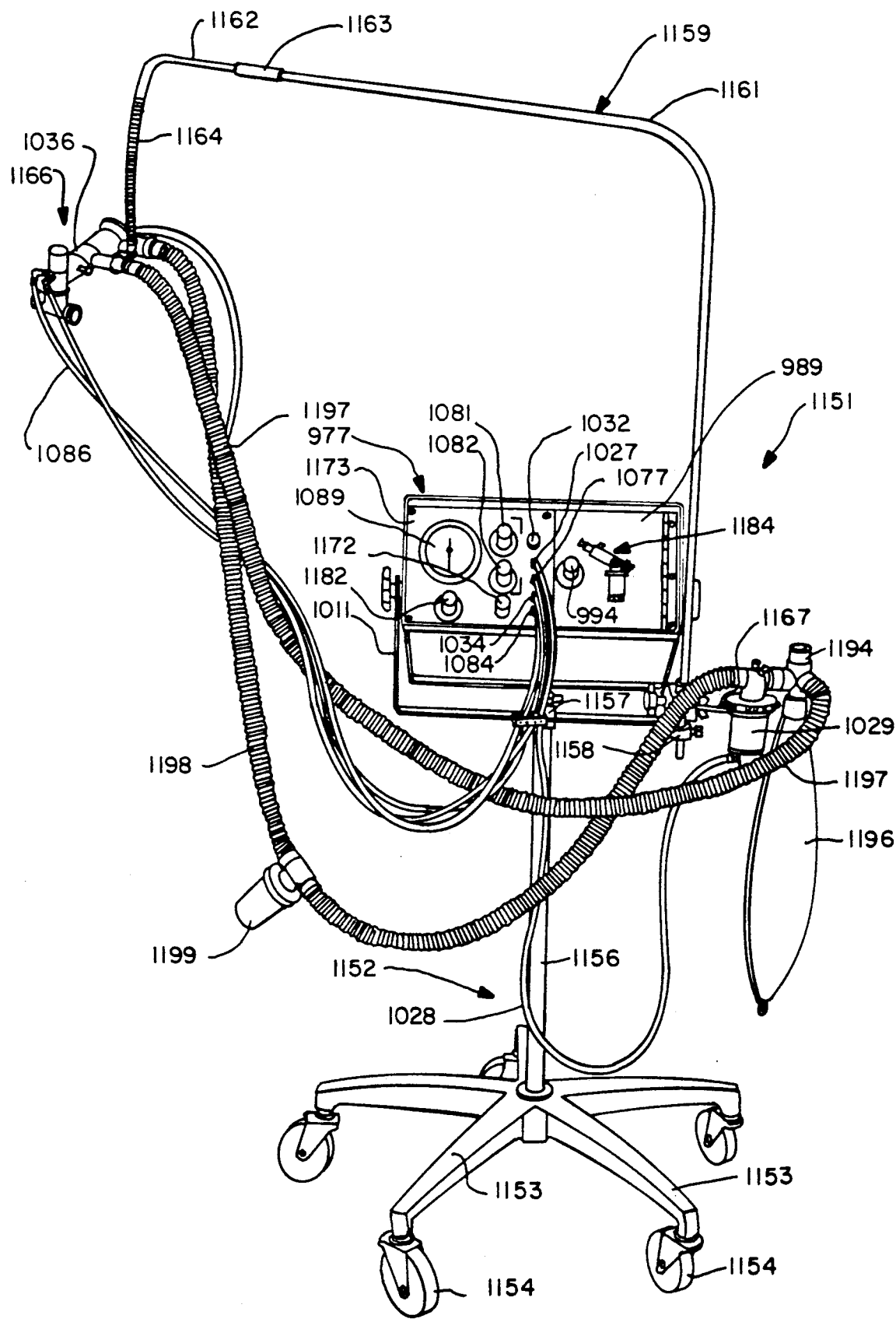
FIG.—22

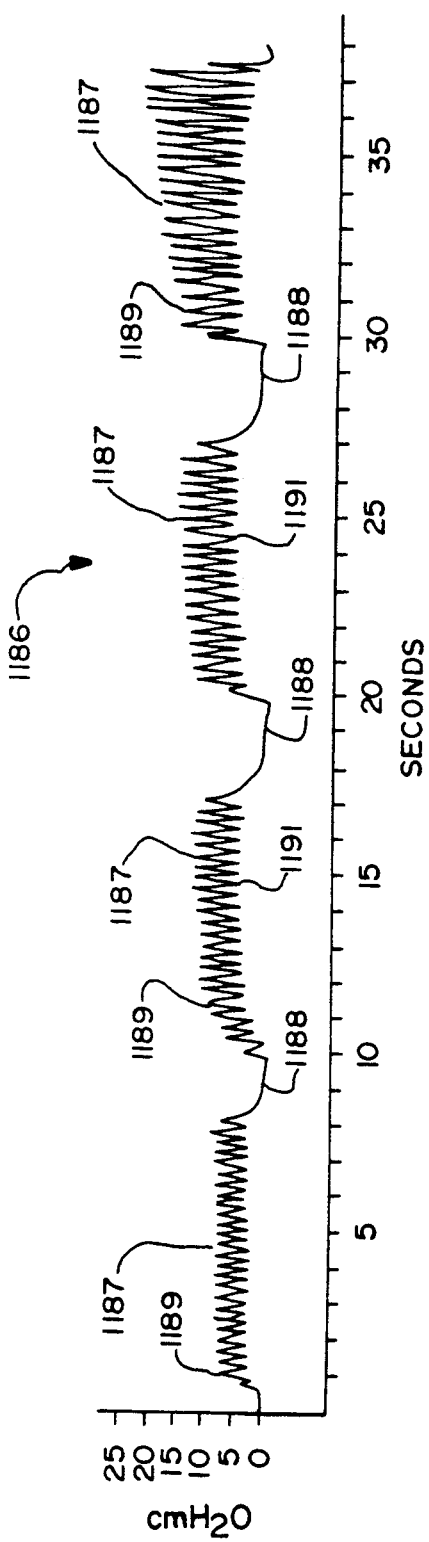
FIG.—24
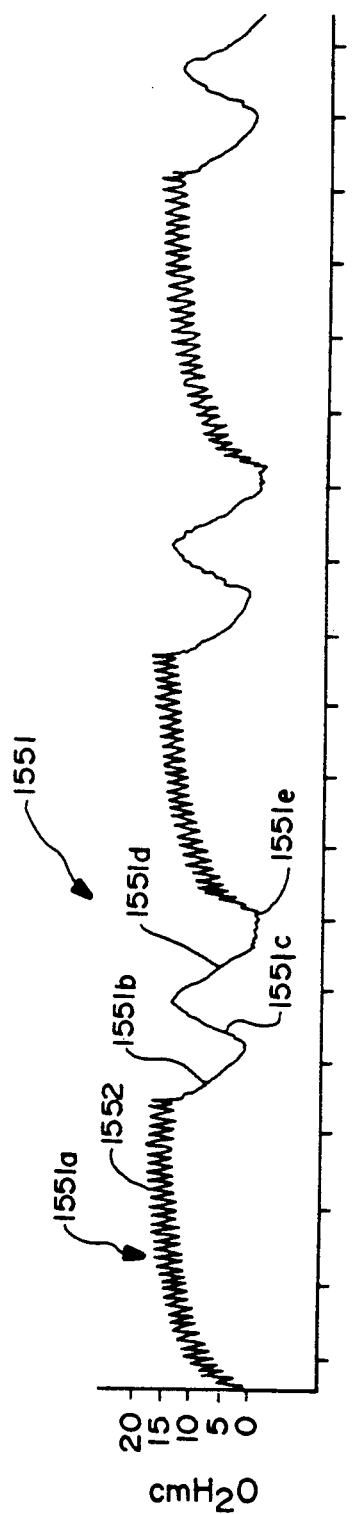
FIG.—32

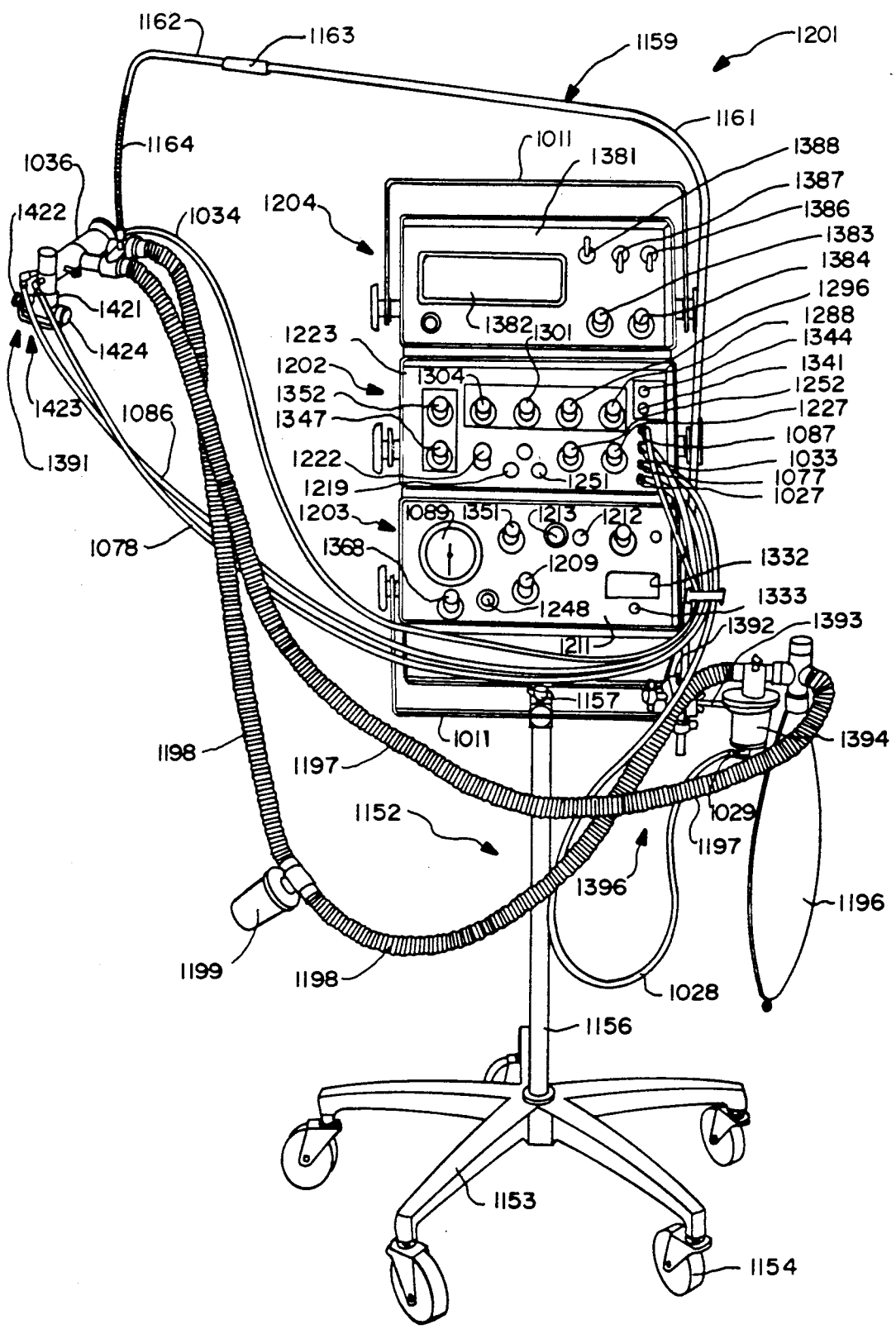
FIG. —25

FIG. —27

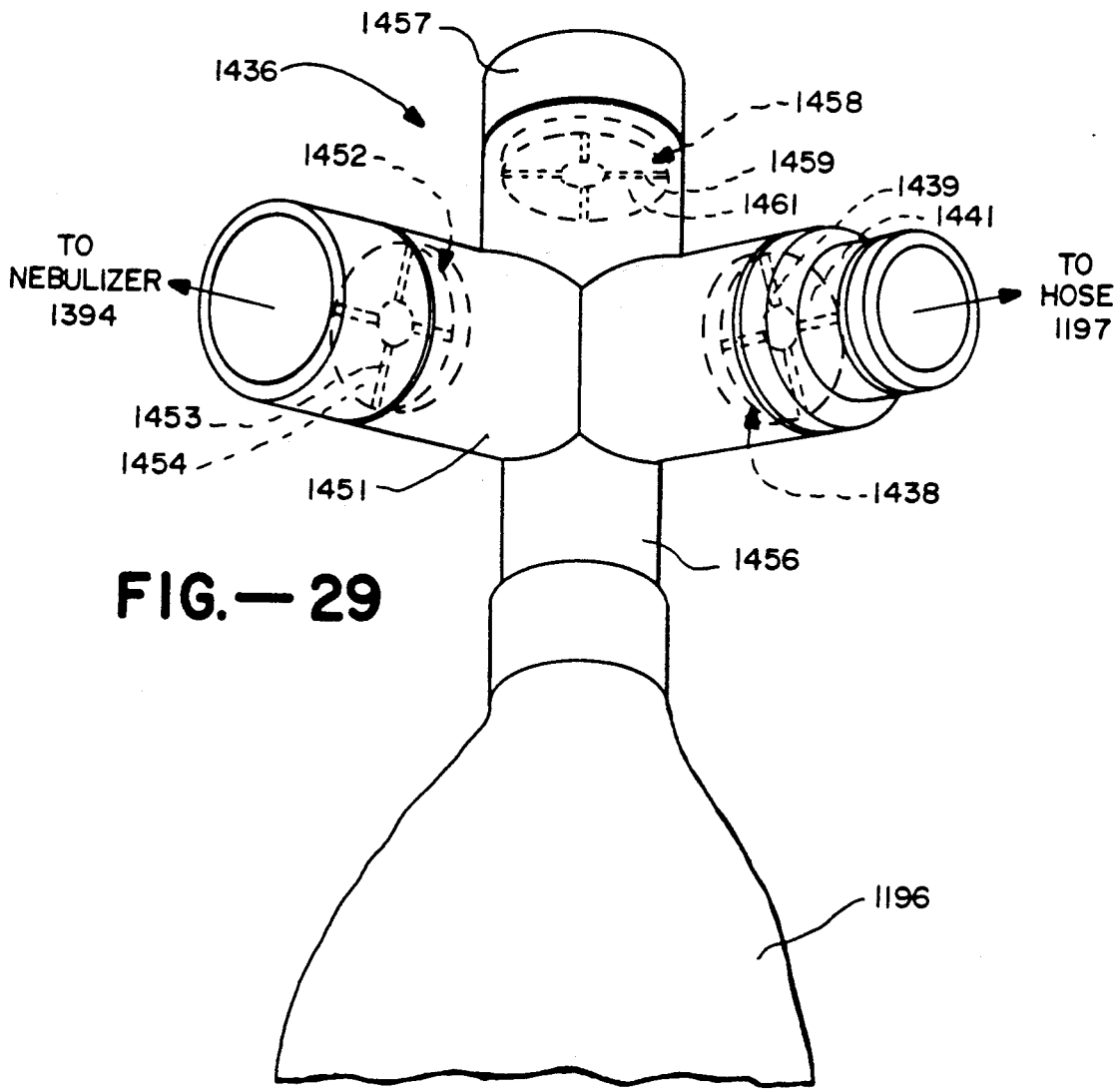
FIG.—29
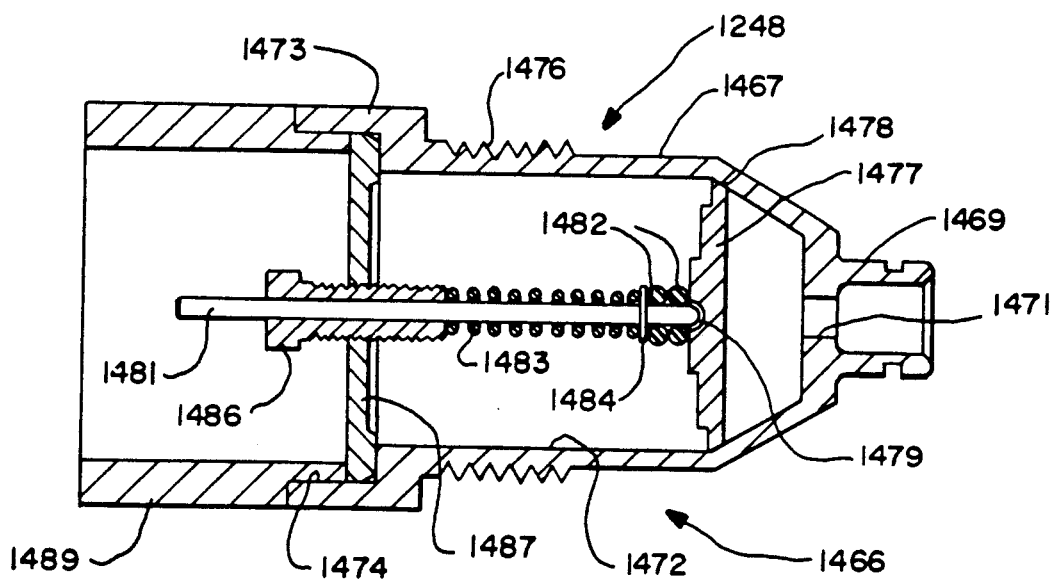
FIG.—30

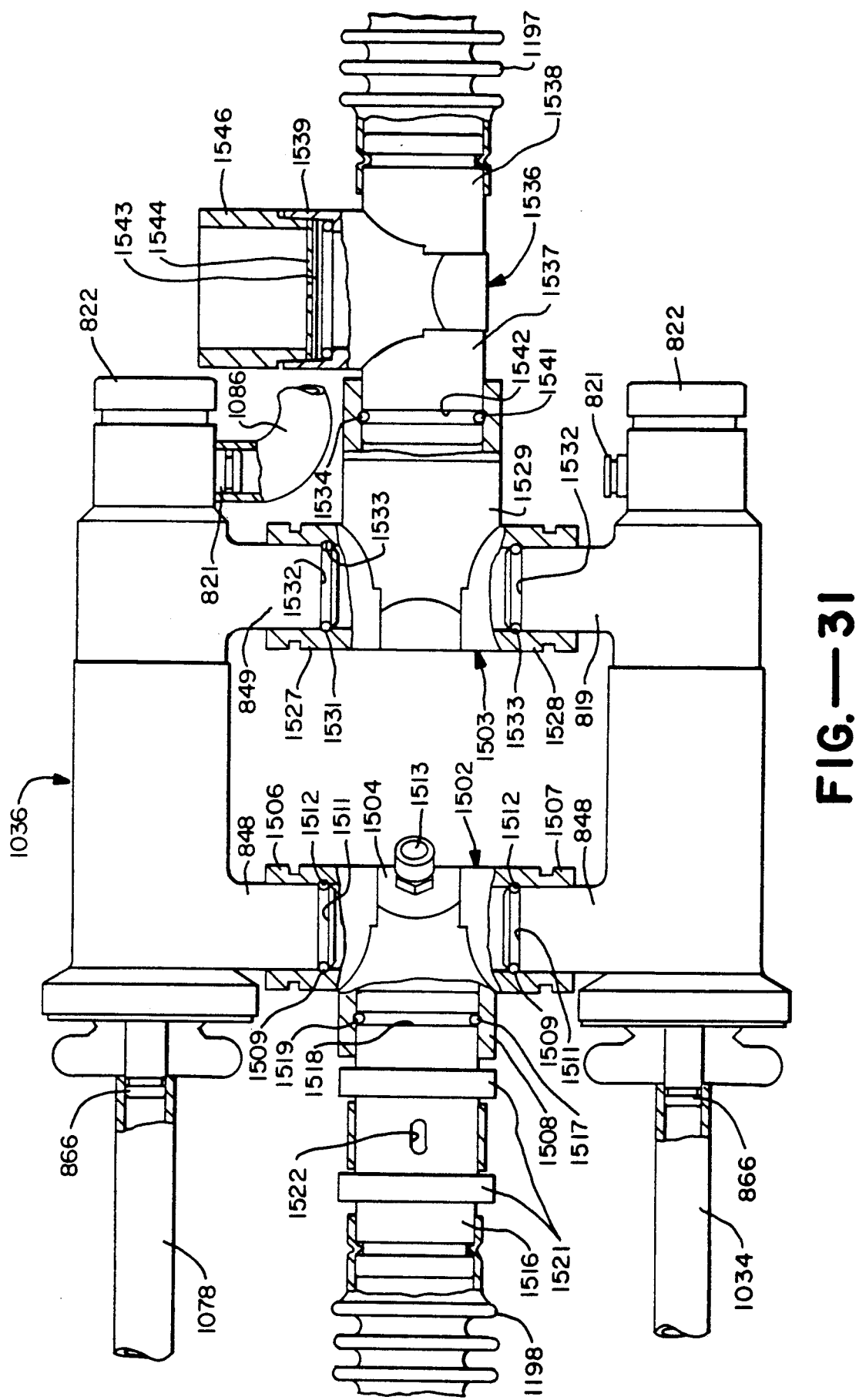
FIG.—31

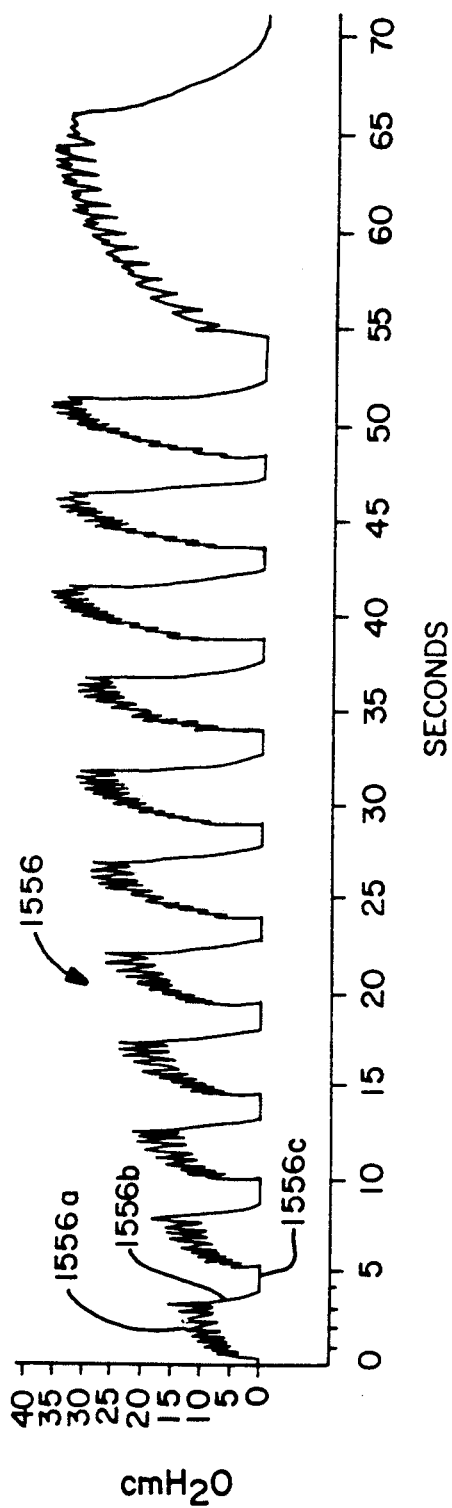
FIG.—33
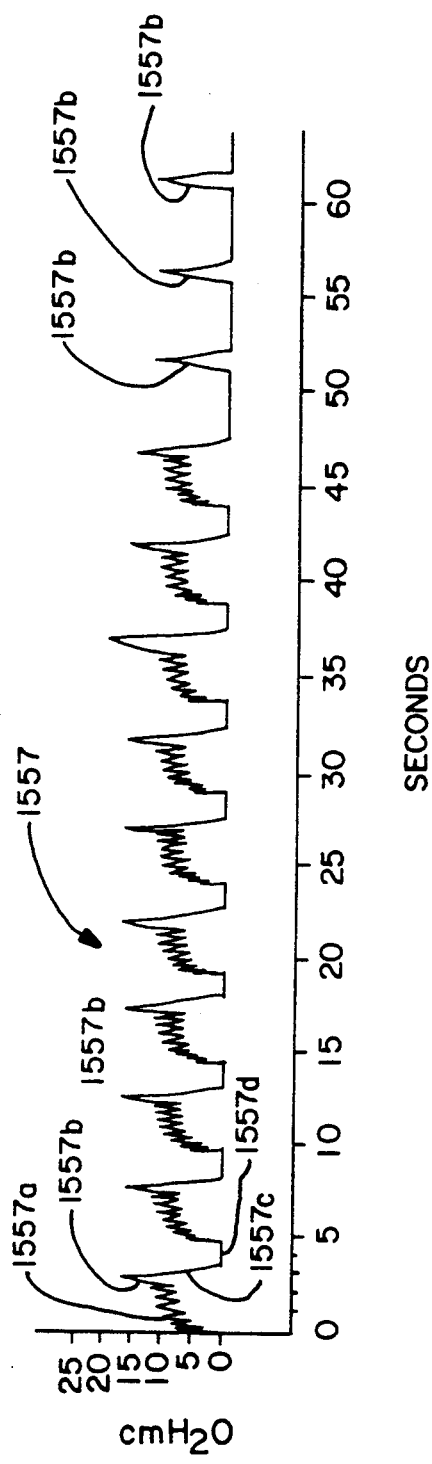
FIG.—34

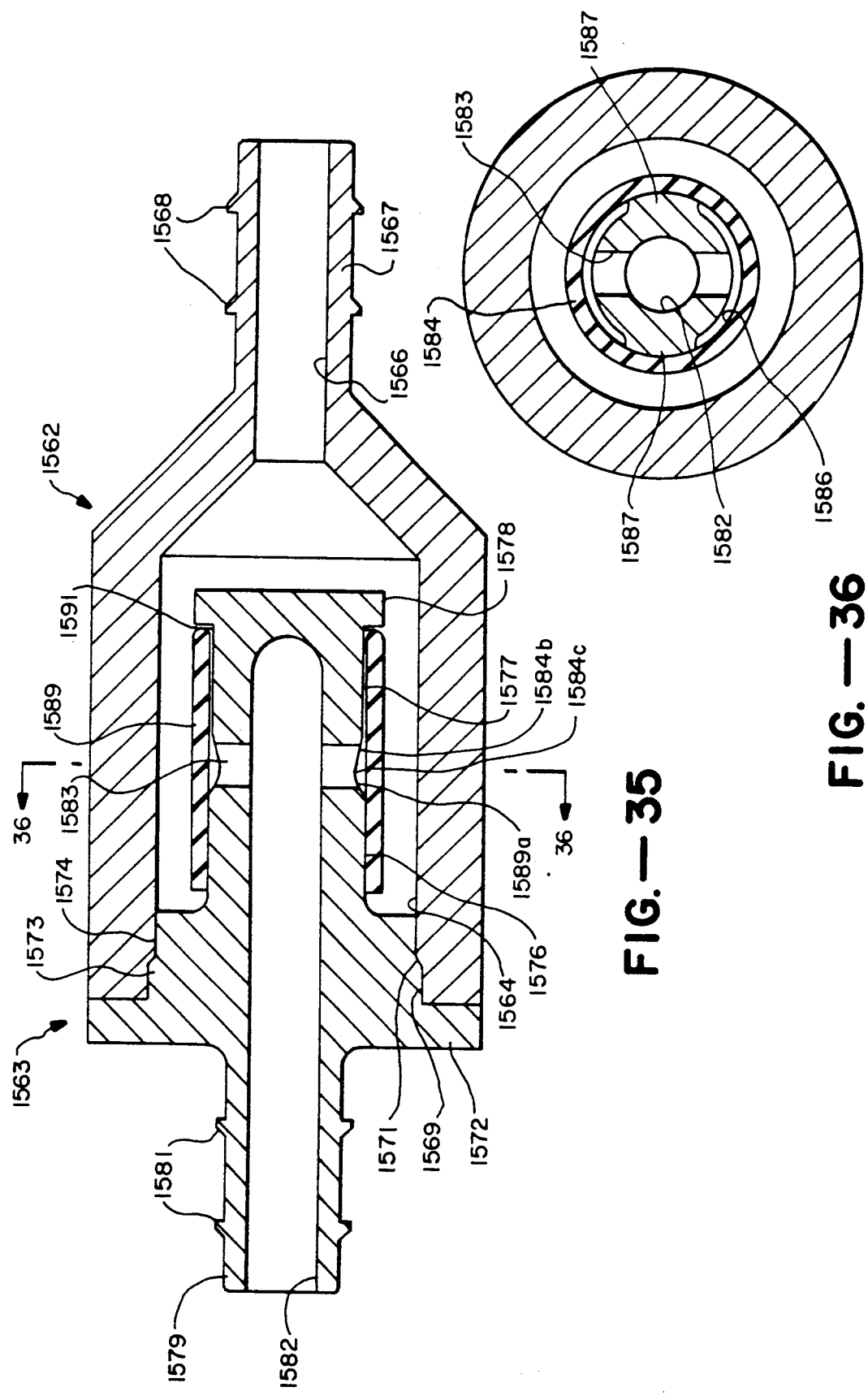

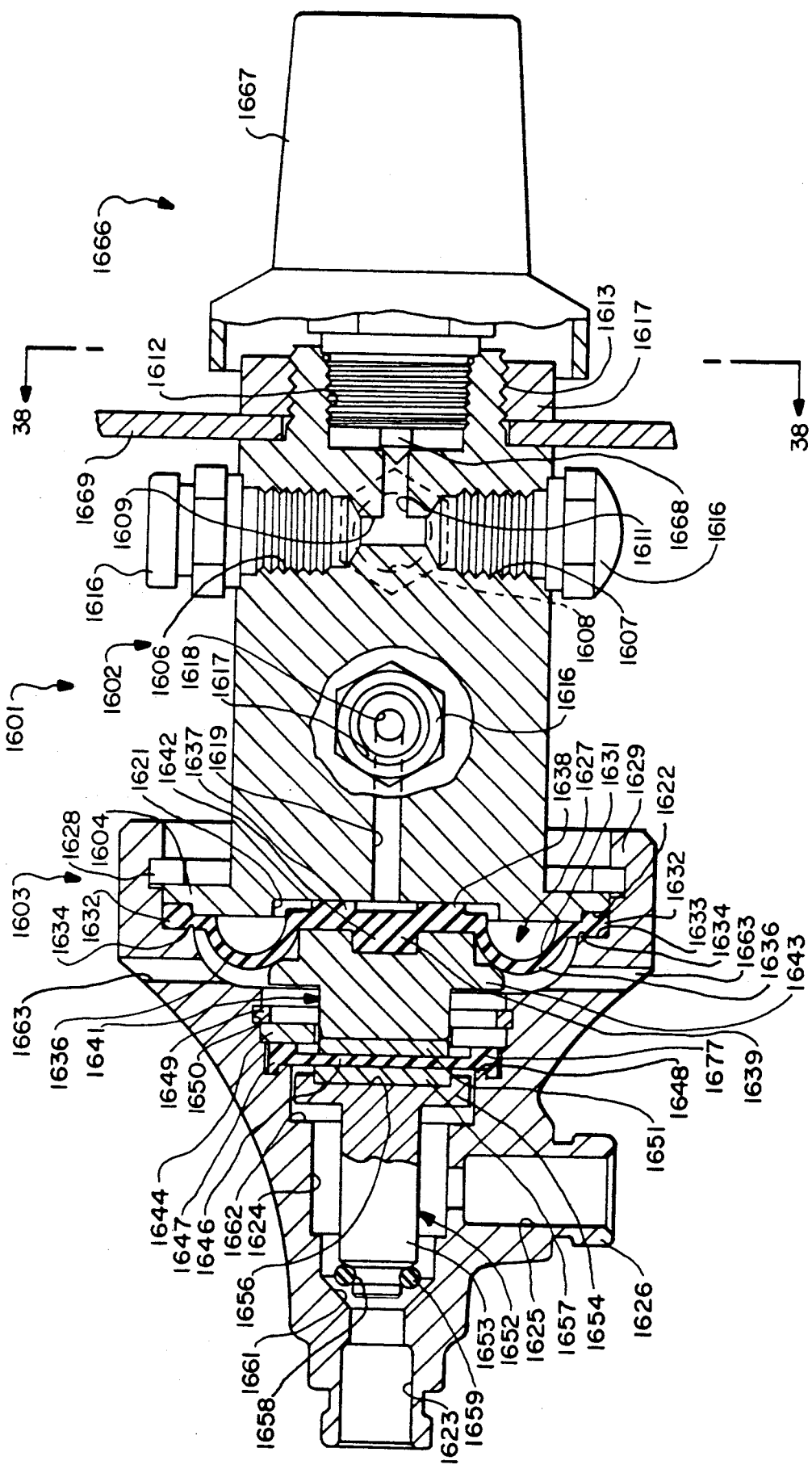
FIG.—37

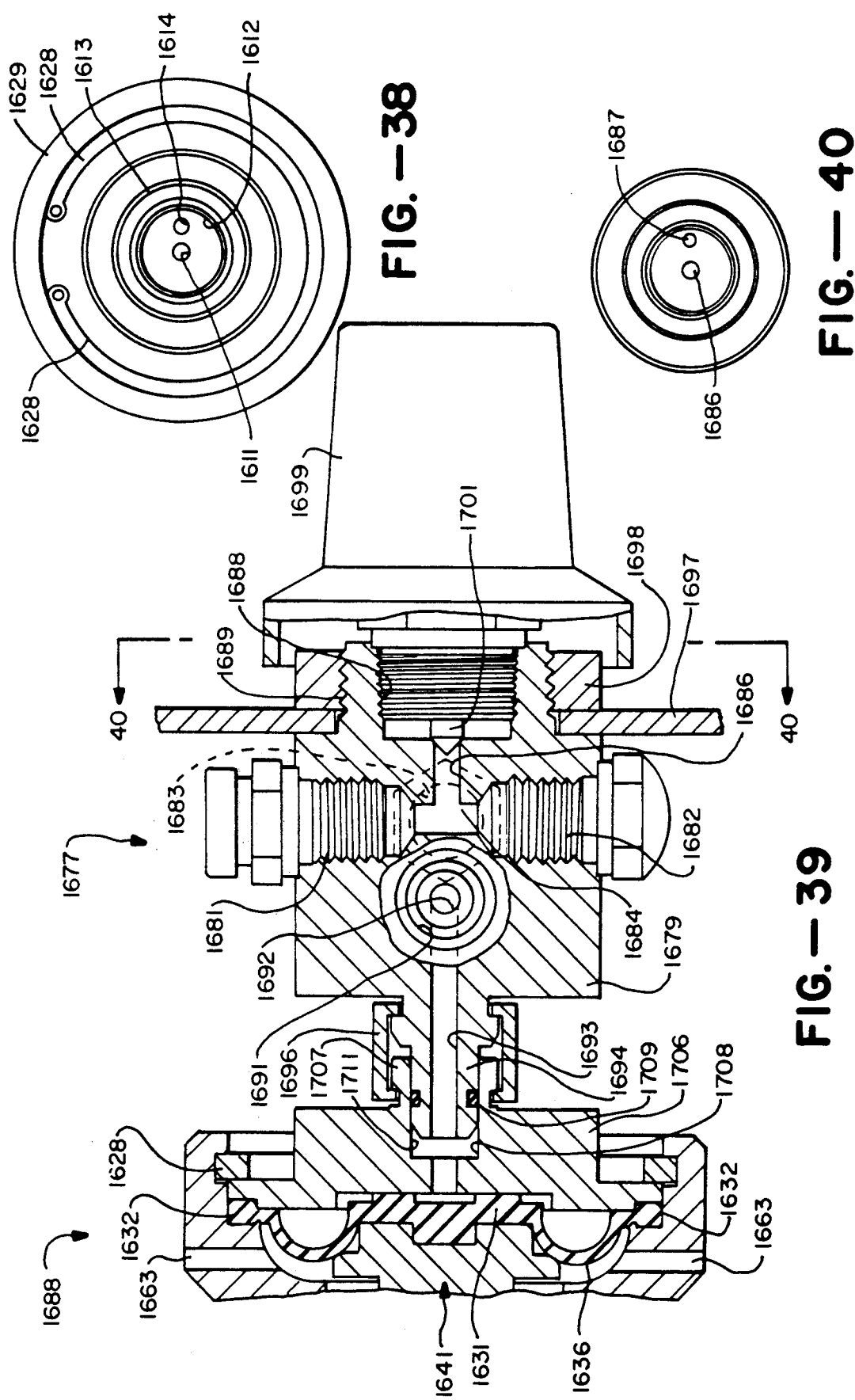

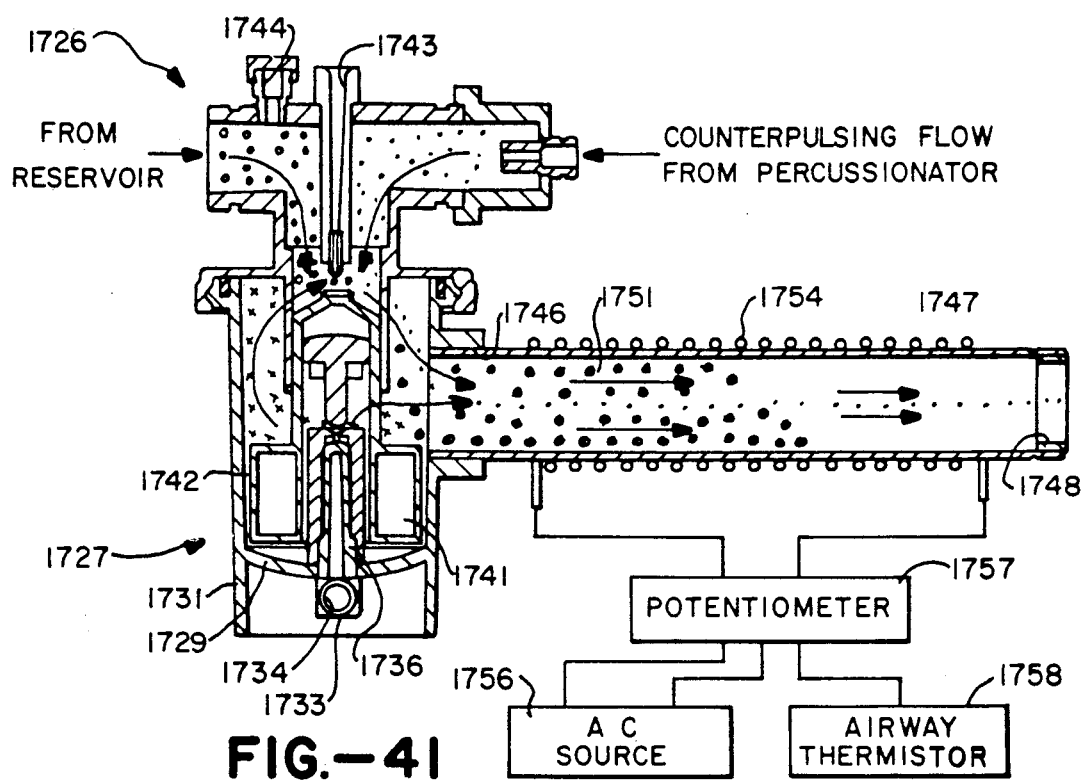
FIG.—41
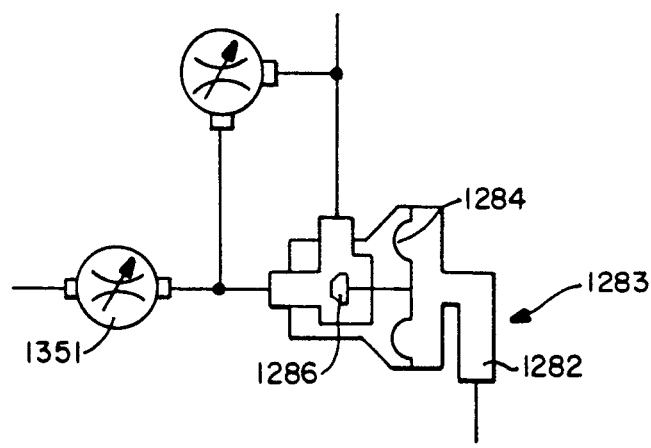
FIG.—42
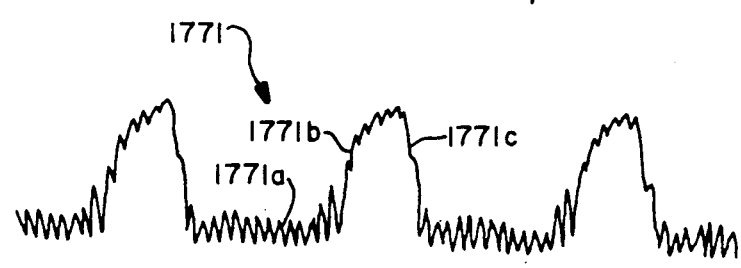
FIG.—43
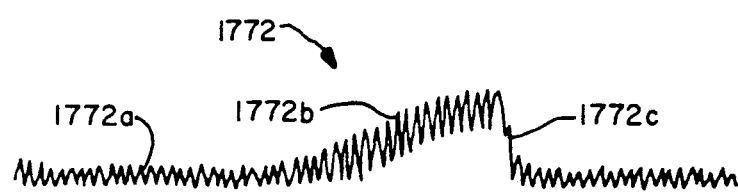
FIG.—44

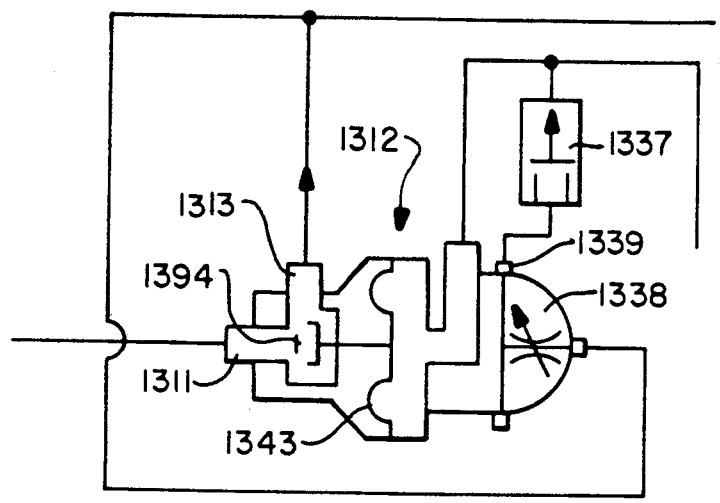
FIG. —45
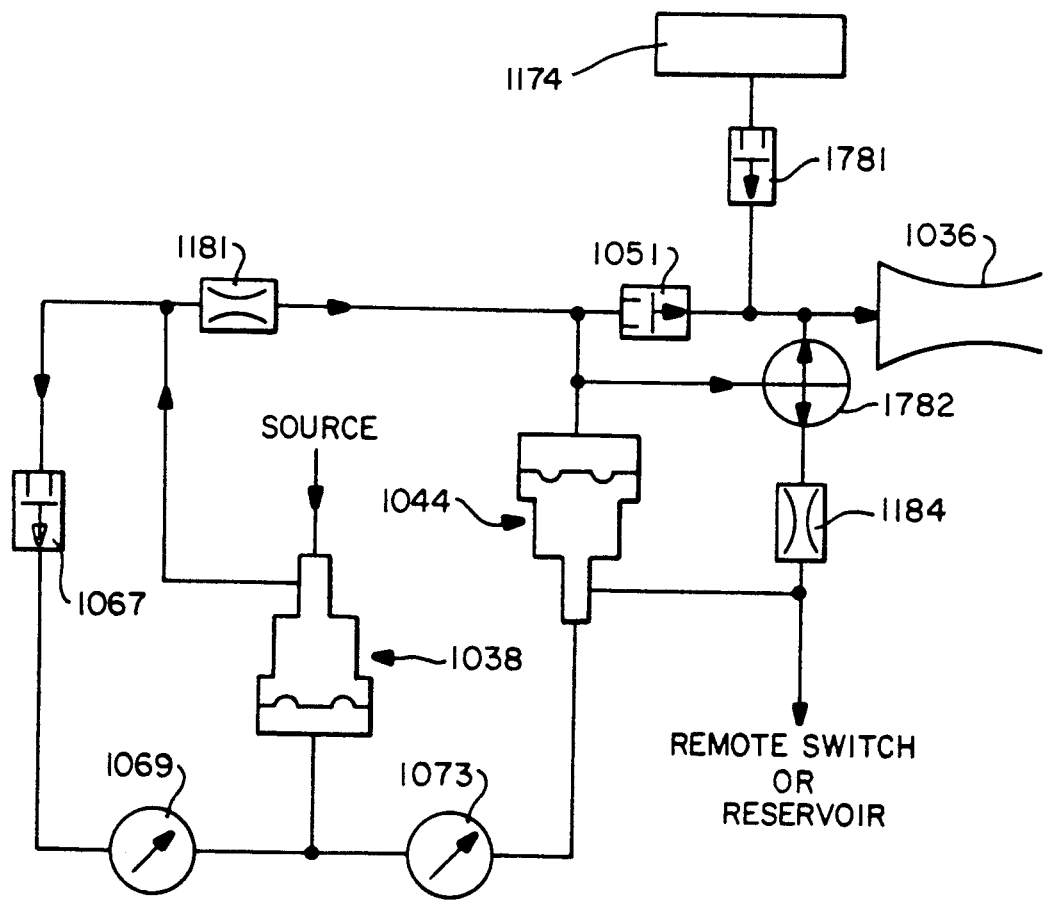
FIG. —46

VENTILATOR HAVING AN OSCILLATORY INSPIRATORY PHASE AND METHOD

This application is a continuation of a continuation-in-part application Ser. No. 671,491 filed on Nov. 11, 1984, abandoned, which is a continuation-in-part of continuation-in-part application Ser. No. 516,133, filed July 21, 1983, now issued as U.S. Pat. No. 4,592,349 on June 3, 1986 which is a continuation-in-part of application Ser. No. 291,622, filed Aug. 10, 1981 and now abandoned and is a continuation-in-part of application Ser. Nos. 269,929 and 250,586, filed on Apr. 3, 1981 and June 2, 1981, respectively, both now abandoned.

This invention relates generally to a ventilator and a method and more particularly to a ventilator having an oscillatory inspiratory phase and method.

Heretofore, ventilators have been provided. However, there has always been a need to obtain better distribution of gas volumes throughout the pulmonary structures of the patient to increase the available blood gas interface. With conventional ventilators, it has become increasingly difficult to make any substantial improvements in obtaining better distribution of gas volumes and therefore there is a need for an improved ventilator and method making this possible.

In general, it is the object of the present invention to provide an improved ventilator and method in which microvolumes of gases can be delivered to the patient airway.

Another object of the invention is to provide a ventilator and method of the above character in which the ventilator gases are delivered in pulsatile form to the patient airway.

Another object of the invention is to provide a ventilator and method of the above character in which the pulsatile gases can be delivered against a constant positive airway pressure in the patient airway.

Another object of the invention is to provide a ventilator and method in which pulsatile gases can be delivered in a programmed manner.

Another object of the invention is to provide a ventilator and method of the above character in which pulsatile gases can be delivered to the airway of the patient under manual control.

Another object of the invention is to provide a ventilator and method of the above character in which the pulsatile gases can be supplied to the airway of the patient at automatically timed intervals.

Another object of the invention is to provide a ventilator and method of the above character in which tidal volumes of gases can be superimposed upon the pulsatile gases delivered to the airway of the patient.

Another object of the invention is to provide a ventilator and method of the above character in which the tidal volumes of gases can be delivered under manual or automatic control.

Another object of the invention is to provide a ventilator and method of the above character in which it is possible to deliver pulsatile gases during the time that tidal volumes of gases are being delivered to the airway of the patient.

Another object of the invention is to provide a ventilator and method of the above character in which pulsatile gases with a programmed amplitude can be supplied to the proximal airway of the patient to produce intrapulmonary mechanical mixing with secondary acceleration of pulmonary gas diffusion.

Another object of the invention is to provide a ventilator and method of the above character in which percussive pulses of gases are supplied to the physiological cardiopulmonary structures of the patient to maintain maximum blood/gas interface and cardiac output while mobilizing intrapulmonary secretions with minimal tendency toward pulmonary barotrauma.

Another object of the invention is to provide a ventilator and method of the above character in which the volume of gases delivered to the patient can be proportioned in accordance with the size of the mammal by increasing or decreasing source pressures.

Another object of the invention is to provide a ventilator and method of the above character in which adequate gases can be supplied to the patient while lowering the source pressure and changing the frequency range proportionally to maintain optimal clinical parameters for frequency and pressure rise.

Another object of the invention is to provide a ventilator and method of the above character in which if failure occurs will fail into a failsafe mode with the initiation of an alarm.

Another object of the invention is to provide a ventilator and method of the above character which prevents overinflation of the pulmonary structures of the patient beyond those mechanically programmed.

Another object of the invention is to provide a ventilator and method of the above character which accommodates both diffusion and volume exchange respiration.

Another object of the invention is to provide a ventilator and method of the above character in which automatic oxygen enrichment is provided during an explosive decompression.

Another object of the invention is to provide a ventilator and method of the above character in which automatic decompression of the patient airway is provided in the event of an explosive decompression.

Another object of the invention is to provide a ventilator and method of the above character in which positive airway pressure is maintained during the time that the patient airway is emptied to the atmosphere in the event of an explosive decompression.

Another object of the invention is to provide a ventilator and method of the above character with which can be utilized adjustable source pressures to provide higher pressures for larger tidal volumes for volumetric respiration and lower pressure for higher frequency stroke volume for diffusion respiration.

Another object of the invention is to provide a ventilator and method of the above character in which higher stroke volumes are utilized for increasing arterial oxygen by diffusion.

Another object of the invention is to provide a ventilator and method of the above character in which periodic large tidal volumes are supplied to the patient airway for diluting or washing out the carbon dioxide in the patient airway.

Another object of the invention is to provide a ventilator and method of the above character in which an oscillatory constant positive airway pressure is maintained for controlling right to left pulmonary shunts and maintaining an effective respiratory diffusion and volumetric exchange.

Another object of the invention is to provide a ventilator and method of the above character in which a minimum amount of dead space is provided with a maximum stroke volume and a minimal oscillatory constant positive airway pressure.

Another object of the invention is to provide a ventilator and method of the above character in which cyclic oscillatory timing is provided with capabilities of manual override to permit patient self-treatment to thereby permit phasing so that the patient can expectorate.

Another object of the invention is to provide a ventilator and method of the above character in which the termination of ventilation is accomplished in a gradual manner in order to minimize the possibility of patient airway collapse.

Another object of the invention is to provide a ventilator and method of the above character which remains in phase at high frequencies.

Another object of the invention is to provide a ventilator of the above character which is entirely under pneumatic control.

Another object of the invention is to provide a ventilator of the above character which can operate reliably at high frequencies for long periods of time.

Another object of the invention is to provide a ventilator and method of the above character which can be utilized with infants and adults.

Another object of the invention is to provide a ventilator which is modular in form.

Another object of the invention is to provide a ventilator of the above character which can be utilized for ventilating neonates to giants.

Another object of the invention is to provide a ventilator of the above character in which control is provided over inspiratory time, expiratory time, inspiratory flow rate, demand CPAP/PEEP and aerosol generation.

Another object of the invention is to provide a ventilator of the above character in which various I/E ratios can be selected.

Another object of the invention is to provide a ventilator of the above character in which inspiratory and expiratory times can be varied.

Another object of the invention is to provide a respirator of the above character in which time cycled expiratory/ inspiratory intervals can be provided.

Another object of the invention is to provide a ventilator of the above character in which a failsafe governor alert has been provided.

Another object of the invention is to provide a ventilator of the above character in which a counterpulsing flow is provided.

Another object of the invention is to provide a ventilator of the above character in which the counterpulsing flow is out of phase with the flow provided by the timing circuit.

Another object of the invention is to provide a ventilator of the above character in which constant positive airway pressure can be provided while the ventilator is being time cycled.

Another object of the invention is to provide a ventilator of the above character in which large variations in timing can be obtained.

Another object of the invention is to provide a ventilator of the above character in which time cycling can be provided with a desired inspiratory/expiratory ratio.

Another object of the invention is to provide a ventilator of the above character in which it is possible to adjust the rate of inspiratory flow while retaining the capability to vary the inspiratory/expiratory ratio.

Another object of the invention is to provide a ventilator of the above character in which the frequency can be controlled independent of the inspiratory/expiratory ratio selected.

Another object of the invention is to provide a ventilator of the above character in which the amplitude can be controlled independent of the selected inspiratory/expiratory ratio.

Another object of the invention is to provide a ventilator of the above character in which certain components of the ventilator bypass the on/off switch to make certain functions of the ventilator obligatory as soon as source gas is connected to the ventilator.

Another object of the invention is to provide a ventilator of the above character which has various failsafe features which prevent overpressures being applied to the patient airway.

Another object of the invention is to provide a ventilator of the above character which prevents a sudden rush of inspiratory gas into the airway of the patient.

Another object of the invention is to provide a ventilator of the above character which prevents a sudden rush of inspiratory gas being supplied to the patient even prior to turning on of the on/off switch of the ventilator.

Another object of the invention is to provide a ventilator of the above character in which certain functions are provided before the ventilator is turned on including demand constant positive airway pressure, manual override, nebulization and failsafe operation.

Another object of the invention is to provide a ventilator of the above character in which a gas leak is provided in the system to prevent a lockout of the system.

Another object of the invention is to provide a ventilator of the above character in which a failsafe exhalation valve assembly is provided in close proximity to the patient airway.

Another object of the invention is to provide a check valve for use in a ventilator which will operate at high frequencies.

Another object of the invention is to provide a check valve of the above character which does not dance or flutter at high frequencies.

Another object of the invention is to provide a flow/-timing cartridge for use in a ventilator which will operate over a very wide range of operational pressures extending from the neo-natal range to the adult range.

Another object of the invention is to provide a flow/-timing cartridge which has an extremely long life.

Another object of the invention is to provide a flow/-timing cartridge which is stable at high frequencies without observable chatter or wobble of the poppet.

Another object of the invention is to provide a flow/-timing cartridge of the above character with excellent flow capabilities while maintaining a substantial pressure drop across the valve gate.

Another object of the invention is to provide a flow/-timing cartridge of the above character which can be constructed in two sections to facilitate replacement of a section.

Another object of the invention is to provide an augmented nebulizer for use in a ventilator of the character described in which the nebulized output is substantially increased.

Another object of the invention is to provide an augmented nebulizer of the above character in which the temperature of the nebulized output gases can be increased.

Another object of the invention is to provide an augmented nebulizer of the above character in which the output gases can be heated to a predetermined temperature.

Another object of the invention is to provide a ventilator having oscillatory demand constant positive airway pressure.

Another object of the invention is to provide a ventilator of the above character having oscillatory demand CPAP in which the ramping up of the wave form occurs in smaller and smaller stroke volumes until a maximum is reached.

Another object of the invention is to provide a ventilator having oscillatory demand CPAP in which there is a relatively smooth ramping up of the wave form and a relatively smooth ramping down of the wave form.

Another object of the invention is to provide a ventilator of the above character in which a substantially sinusoidal wave pattern can be produced.

Another object of the invention is to provide a ventilator of the above character in which stable pulsations can be provided over the entire range of operation of the ventilator.

Another object of the invention is to provide a ventilator of the above character which remains stable at different altitudes.

Another object of the invention is to provide a ventilator of the above character in which such stability at various altitudes is obtained by shifting the position of the loading valve with respect to the primary oscillator cartridge.

Another object of the invention is to provide a ventilator which incorporates mode switching so that patient care can be programmed to the amount of medical source gas available.

Another object of the invention is to provide a ventilator of the above character incorporating the present invention which can be utilized with relatively small volumes of available medical source gas.

Another object of the invention is to provide a ventilator of the above character which is provided for means for limiting pressure rise in a time cycled pressure variable ventilator.

Additional objects and features of the invention will appear from the following description in which the preferred embodiment is set forth in detail in conjunction with the accompanying drawings.

FIG. 1 is a schematic illustration of a ventilator incorporating the present invention.

FIG. 2 is a graph showing the method by which a patient is ventilated with the present ventilator.

FIG. 3 is a schematic illustration of another embodiment of a ventilator incorporating the present invention.

FIG. 4 is a graph showing the method by which a patient is ventilated with the ventilator shown in FIG. 3.

FIG. 5 is a schematic diagram of a breathing circuit for use in ventilators of the present invention and which incorporates a particularly novel nebulizer and shrouded venturi assembly.

FIG. 6 is a schematic illustration of still another ventilator incorporating the present invention.

FIG. 6A is a schematic diagram of an optional oscillator and breathing circuit for use in the ventilator shown in FIG. 6.

FIG. 6B is a schematic illustration of a breathing circuit utilizing a sub-ambient venturi for the exhalation valve assembly for use in the ventilator shown in FIG. 6.

FIG. 7 is a schematic illustration of still another ventilator incorporating the present invention.

FIG. 7A is a schematic diagram of an optical circuit for use in the ventilator shown in FIG. 7.

FIG. 8 is a schematic illustration of a decompression and expiratory oscillation module for use in a ventilator of the type shown in FIG. 3.

FIG. 9 is a schematic illustration of an automatic aneroid decompression relief valve assembly adapted to be used in a ventilator of the type shown in FIG. 3.

FIG. 10 is a cross sectional view of a combination venturi assembly and exhalation valve assembly which can be utilized in the ventilator of the present invention.

FIG. 11 is a schematic illustration of a breathing circuit for use with the ventilators of the present invention.

FIG. 12 is a side elevational view of a quick-disconnect fitting for use in ventilators of the present invention.

FIG. 13 is a cross sectional view taken along the line 13—13 of FIG. 12.

FIG. 14 is a side elevational view of another embodiment of a quick disconnect fitting for use in ventilators of the present invention.

FIG. 15 is a cross sectional view taken along the line 15—15 of FIG. 14.

FIG. 16 is a perspective view of a ventilator incorporating the present invention being utilized by a patient.

FIG. 17 is a view of the ventilator shown in FIG. 16 but showing the compartment door in an open position and showing the handle supporting the ventilator so that the front panel is inclined.

FIG. 18 is a schematic circuit of the pneumatic circuitry utilized in the invention shown in FIG. 17.

FIG. 19 is a cross sectional view of a flow obtunder used in the circuitry shown in FIG. 18.

FIG. 20 is a side elevational view of a nebulizer incorporating the present invention.

FIG. 21 is a cross sectional view of a portion of the nebulizer shown in FIG. 20.

FIG. 22 is still another embodiment of a ventilator incorporating the present invention and showing the same mounted upon a stand so that it can be wheeled from one location to another.

FIG. 24 is a graph showing the performance of the ventilator shown in FIG. 22 and 23.

FIG. 25 is still another embodiment of a ventilator incorporating the present invention.

FIG. 29 is an isometric view of a portion of the breathing apparatus connected to the ventilator in FIG. 25.

FIG. 30 is a cross sectional view of a governor alert incorporating the present invention and used in the ventilator in FIG. 25.

FIG. 31 is a view of a dual combination venturi jet and exhalation valve assembly with certain portions broken away. FIGS. 32 through 34 are graphs showing the performance of the ventilator shown in FIG. 25.

FIG. 35 is an enlarged cross-sectional view of a modified sleeve check valve.

FIG. 36 is an enlarged cross-sectional view taken along the line 36—36 of FIG. 35.

FIG. 37 is a side elevational view partially in cross section of a flow/timing cartridge incorporating the present invention and for use in a ventilator.

FIG. 38 is a cross sectional view taken along the line 38—38 of FIG. 37.

FIG. 39 is a cross sectional view, also partly in cross section of a flow/timing cartridge incorporating the present invention for use in a ventilator and similar to the flow timing cartridge shown in FIGS. 37 and 38 but differing in that it is formed in two sections which may be removably detached from each other.

FIG. 40 is a cross sectional view taken along the line 40—40 of FIG. 39.

FIG. 41 is a cross sectional view, partially in schematic form of an augmented nebulizer incorporating the present invention for use in a ventilator and having auxiliary heating means.

FIG. 42 is a schematic diagram of an enhancement metering circuit which can be utilized in the circuit shown in FIG. 26 to provide oscillatory demand CPAP.

FIG. 43 is a wave form obtained from the circuitry shown in FIG. 42 and providing an oscillatory demand CPAP.

FIG. 44 is a graph produced from the ventilator shown in FIG. 42 and in which a sinusoidal oscillatory demand CPAP is obtained.

FIG. 45 is a partial schematic view of the ventilator shown in FIG. 26 showing the manner in which the loading valve position has been changed with respect to the primary oscillator cartridge to obtain ventilator stability at different altitudes.

FIG. 46 is a schematic diagram of the mode switching arrangement for use with ventilators of the present invention.

Figure 23:
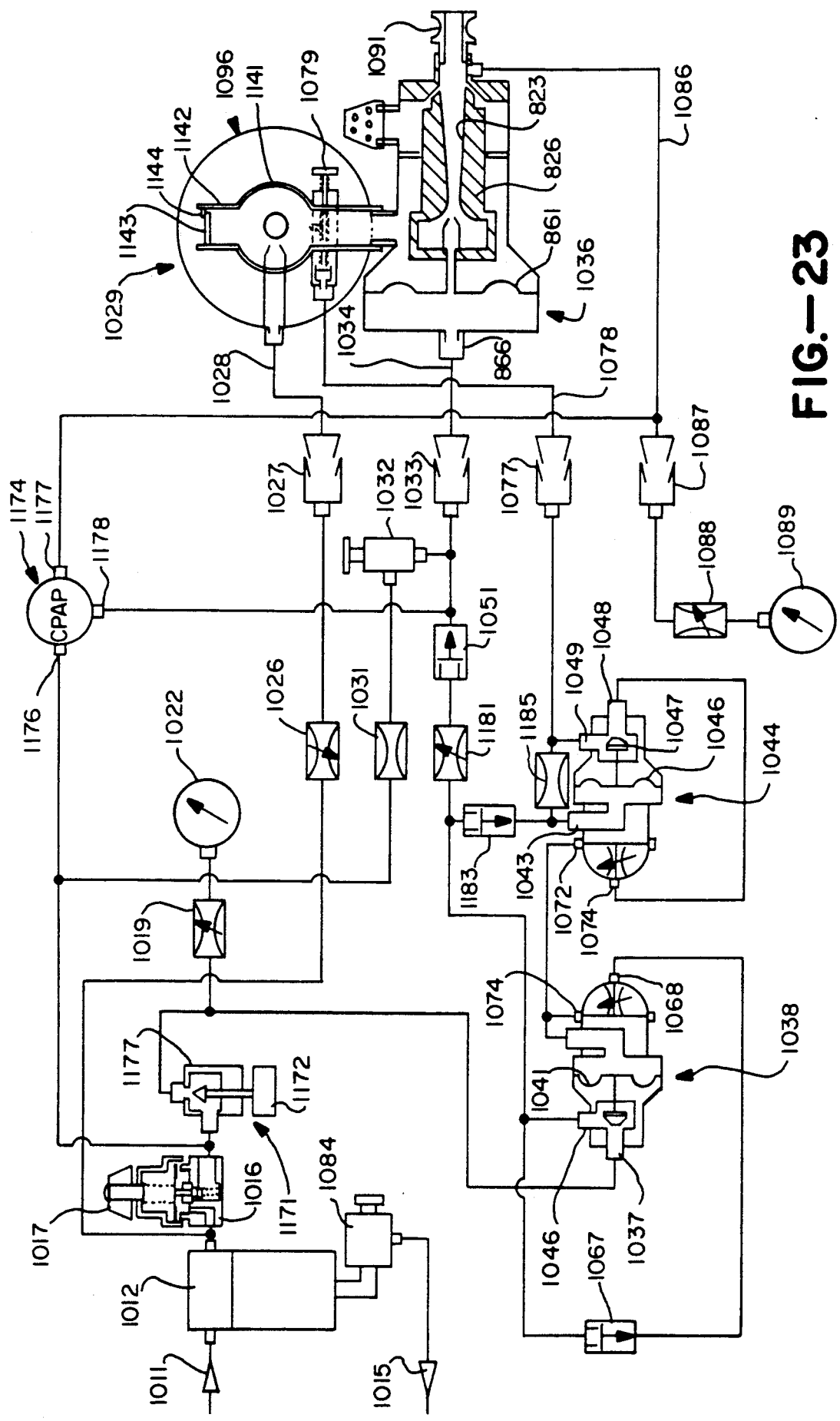
FIG. 23 is a schematic diagram of the pneumatic circuitry ventilator shown in FIG. 22.

In FIG. 1, there is shown a schematic diagram of a ventilator having an oscillatory inspiratory phase which as shown consists generally of a power control module 11, an oscillatory diffusion module 12, a transport service module 13, an oscillatory volumetric ventilator module with CPAP and alarm-failsafe 14, and a universal breathing circuit 16.

The power control module 11 consists of an oxygen blender 21 of conventional type such as that described in U.S. Pat. No. 3,727,627. The oxygen blender 21 is provided with inlet ports 22 and 23 with inlet port 22 being connected to a suitable source of gas such as air under pressure and port 23 being connected to another source of gas as, for example, oxygen under pressure. The blender 21 is provided with a control knob 25 to permit the adjustment of the ratio of air to oxygen. The blender 21 is provided with additional ports 24, 26 and 27. The port 24 is connected to port 27. The port 24 is also connected to the outlet port 31 of a normally closed bypass cartridge 32. The bypass cartridge 32 is adapted to be moved to an open position by gas being supplied to a servo port 33 of the bypass cartridge 32. The bypass cartridge 32 is also provided with an inlet port 34 which is connected through isolation check valves 36 and 37 connected respectively to the inlet ports 22 and 23 and to the sources of air and oxygen as shown.

The outlet 26 from the blender 21 typically is an outlet which provides an alarm when there is inadequate or single gas available to the blender 21. As pointed out herebefore, this outlet 26 is connected to the inlet port 33 of the bypass cartridge 32 so that in the event there is insufficient gas flow through the blender 21, the bypass cartridge 32 is actuated to move it to an open position to permit gas to flow either from the sources of air or oxygen through the isolation valves 36 and 37 through the inlet port 34 and through the outlet port 31 to the outlet port 24 of the blender 21.

Means is provided for giving an indication as to when the bypass cartridge is actuated to cause bypassing of the blender 21 and consists of an adjustable bypass indicator calibration valve 38 which is connected to the inlet port 33 of the bypass cartridge 32. The calibration valve 38 is also connected to a bypass indicator 39 of a conventional type such as a "Rotowink" light which is a light which changes color from a normal black to a red during the time that the bypass cartridge is bypassing gas. The valve 38 is also connected to a fixed bleed orifice 41 which is open to ambient. For example, it can have a suitable size such as 0.013 of an inch and is utilized to prevent an overpressure from occurring. If desired, the bleed orifice can be connected to a suitable audible alarm, as for example a whistle.

Gas from the power control module 11 from the outlet 24 of the blender 21 is supplied to the transport service module 13 to inlet 44 of an adjustable system pressure regulator 46. The system pressure regulator 46 is utilized for reducing the line pressure from above fifty pounds down to approximately fifty psi. The gas supplied from the power control module 11 in addition to being supplied to the inlet 44 of the pressure regulator 46 is also supplied to an aspirator power socket 47 of the transport service module 13. Gas is also delivered to the inlet port 48 of a demand CPAP cartridge 49.

Unregulated gas is also supplied from the inlet port 44 of the regulator 46 to the inlet port 51 of an adjustable nebulizer control valve 52 of the oscillatory diffusion module 12. Metered gas is then supplied from the valve 52 through its outlet port 53 to a nebulizer service socket 54. A fitting 56 is mounted in the service socket 54 and is connected to an inlet port 57 of a nebulizer 58. The nebulizer 58 can be of the type described in U.S. Pat. No. 3,353,536. In addition, unregulated gas is supplied from a line connected to the inlet 44 of the regulator 46 to the inlet 61 of another adjustable reservoir control needle valve 62. The outlet port 63 of the needle valve 62 is connected to a reservoir service socket 64. A fitting 66 is mounted in the service socket 64 and is connected to an inlet port 67 of an entrainment gate 68 which is connected to an entrainment reservoir 69. Thus it can be seen that unregulated mixed gases of the appropriate type are supplied to the aspirator power socket 47, to the inlet of the demand CPAP cartridge 48 and to the inlets of the nebulizer control metering valve 52 and the reservoir control valve 62.

With respect to gas which is supplied through the regulator 46, such regulated gas is supplied from an outlet 70 through an adjustable orifice 71 to a gauge 72 which registers the regulated pressure which is supplied from the regulator 46. The orifice 71 minimizes the effect of fluctuating pressures on the gauge 72. Regulated gas is also supplied to the inlet 73 of a manual inspiration valve 74. The manual inspiration valve 74 is provided with a push button 76 which when actuated places the ventilator in an inspiratory phase as hereinafter described and supplies regulated gas through its outlet port 77 to an inlet port 78 of a normally open failsafe cartridge 79. The gas flows from the inlet port 78 through an outlet port 81 to a venturi service socket 82. A fitting 83 is mounted in the service socket 82 and is connected to a jet or nozzle 84. An inlet port 86 of the normally open failsafe cartridge 79 is connected to an outlet port 87 of an interrupter cartridge 88.

The transport service module 13 also includes a gauge 89 which is utilized for measuring the vacuum which is established during aspiration. The gauge 89 is connected to aspirator monitor service socket 90. This aspirator service socket can receive a fitting which can be utilized to monitor the aspirator pressure which is being generated. The outlet port 47 of the regulator 46 is also connected to the inlet port 91 of a rotary on/off master switch 92 in the oscillatory diffusion module 12. The outlet 93 of the switch 92 is connected through a timing isolation check valve 94 to an inlet port 96 of a sealed aneroid timing regulator 97 forming a part of the transport service module 13. This regulator 97 is set at a lower pressure than the regulator 46 as, for example, 30 psi. The regulator 97 is provided with a sealed reference gas as, for example, a reference which will provide an output of 30 psi. This constant pressure of 30 psi is used in the master timing circuit as hereinafter described so that the timing is not changed in the event of an explosive decompression. The outlet port 98 of the regulator 97 is connected to an inlet port 99 on a timing cartridge 101.

The transport service module 13 also includes another gauge 102 which is provided for measuring the pressure in the patient's airway. This gauge is connected to an adjustable orifice 103 which is connected to a service socket 104. A fitting 106 is provided in the service socket and is connected to a port 107 of an encapsulated venturi assembly 108. In this way, the pressure in the proximal airway breathing circuit for the patient is measured. This airway pressure which is being monitored is supplied from the socket 104 to an inlet port 109 of the demand CPAP cartridge 49. This gas is also supplied to an adjustable metering valve 111 which is provided for CPAP dampening. The outlet of the metering valve 111 is connected to an outlet port 112 of the demand CPAP cartridge 49. The outlet is also connected to a one way check valve 113 to the inlet port 78 of the failsafe cartridge 79. The connection between the needle valve 111 and the outlet port 112 serves to stabilize the operation of the demand CPAP cartridge.

Now with respect to the oscillatory diffusion module 12, regulated gas which is supplied from the regulator 46 through the rotary on/off switch 92 is supplied through the timing isolation check valve 94 to an inlet port 116 of a normally open automatic nebulization cartridge 117.

In the oscillatory diffusion module, the outlet port 93 of the rotary master switch 92 is connected to an oscillator reservoir 121 which is utilized for smoothing out the operational pressures. The oscillator reservoir 121 is connected to an inlet port 122 of an oscillator cartridge 123. The oscillator reservoir 121 is also connected to the inlet port 124 of an autoload cartridge 126. Gas is also supplied to one side of the reset check valve 127 and to a loading orifice 128 of a suitable size such as 0.013 of an inch to the servo port 129 of the autoload cartridge 126. A loading reservoir 130 is connected between the servo port 129 of the autoload cartridge 126 and the reset check valve 127. The autoload cartridge 126 is a normally open cartridge and gas supplied to the inlet port 124 travels through an outlet port 131. Gas is supplied from the outlet port 131 to one side of a ramping isolation check valve 132 and to a servo port 133 of a normally open interrupter cartridge 88. The cartridge 88 is provided with an inlet port 134. Gas is also supplied from the outlet port 131 to one side of a servo isolation check valve 135.

The oscillator cartridge 123 is provided with an outlet port 136 connected to the inlet port 134 of the interrupter cartridge 88 and to one side of an oscillatory control isolation check valve 137. The other side of the check valve 137 is connected to an inlet port 138 of an inspiratory metering valve 139. The inspiratory metering valve 139 is provided with an outlet port 141 which is connected to an inlet port 142 of an expiratory metering valve 143. The inspiratory metering valve 139 is provided with an outlet port 144 connected to a servo port 146 of the oscillator cartridge 123. The expiratory metering valve 143 is provided with an outlet port 147 connected to the reservoir service socket 64 and thence into the bag-like entrainment reservoir 69.

When the interrupter cartridge 88 is open, gas flows from the outlet port 87 of the interrupter cartridge to an inlet port 151 of an adjustable metering valve 152 which meters gas into a servo port 153 of a failsafe servo cartridge 154 and to an anti-surge pressure balance reservoir 155 which is connected to one side of an alarm reset check valve 156. Gas in addition to being supplied to the inlet port 151 is supplied to the other side of the alarm reset check valve 156 and also to an inlet port 157 of the failsafe servo cartridge 154. The failsafe servo cartridge 154 is a normally closed cartridge and when gas supplied to the servo port 153, the cartridge is moved to the open position and gas flows through an outlet port 158 and is supplied to a failsafe indicator 159 and to a servo port 161 of the normally open failsafe cartridge 79. At the same time that gas is supplied to the servo port 161, it is also supplied to the inlet port 162 of a failsafe alarm calibration metering valve 163. The gas from the outlet port 164 of the metering valve 163 is supplied to an alarm isolation check valve 166 which is connected to an audible whistle alarm 167. The outlet port 164 is also connected to an alarm balance orifice 168 of a suitable size as, for example, 0.024 inches and is connected to the entrainment reservoir 69. If the tubing leading to reservoir 69 is overfilled, or in other words overwhelmed, gas will pass in a reverse direction through the alarm balance orifice 168 through the check valve 166 and into the alarm 167 to sound an alarm.

Once an alarm sounds, it is necessary to provide some means for resetting the failsafe servo. This is accomplished by the use of a normally closed failsafe reset pushbutton 171 which is connected to an outlet port 172 of the adjustable metering valve 152. When the pushbutton 171 is operated, gas is dumped from behind the diaphragm in the failsafe servo cartridge 154 permitting the failsafe servo cartridge to return to its normally closed position. This will permit the system to start operating again. The amount of pressure which is required for opening the failsafe servo cartridge can be adjusted by rotation of the knob 173 of the cartridge 154.

In the oscillatory diffusion module 12, the timing cartridge 101 is provided with an outlet port 176 which is connected to a timing manifold 177. The timing manifold 177 is connected to one side of the ramping isolation check valve 132. It is also connected to one side of an adjustable ramping orifice 178 which is connected to the servo port 133 of the interrupter cartridge 88. One side of the ramping isolation check valve 132 is connected to the servo port 133 and thus gas supplied from the timing manifold 177 rapidly servos the interrupter cartridge 88 to a closed position from its normally open position. Gas introduced into the interrupter cartridge 88 causing it to servo into the closed position will be gradually bled off through the ramping orifice 178 to create a slow opening of the interrupter cartridge to prevent stalling of the oscillator by dropping servoing pressure too rapidly. Gas bleeding from the interrupter cartridge bleeds through the ramping orifice 178 and back into the timing manifold 177 which would be depressurized by this time.

The manifold 177 is also connected to a reservoir refill orifice 179 of suitable size such as 0.024 inches. The other side of the orifice 179 is connected to the reservoir 69. The timing manifold 177 is also connected to the servo ports 181 of the automatic nebulization cartridge 117 and also to the servo port 182 of the timing reset cartridge 183. The timing manifold 177 is also connected to a timing isolation check valve 184 which is connected to a volumetric exchange or exhalation metering valve 186. The metering valve 186 is connected to a timing reservoir 187. The timing reservoir 187 is connected to a servo port 188 of the timing cartridge 101.

As hereinafter explained, when the timing cartridge 101 is servoed from its normally open position to a closed position, it will again open for an appropriate period of time as determined by the bleed down through a diffusion interval adjustable metering valve 189 which is connected to the inlet port 191 of the timing reset cartridge 183. Gas passing into the inlet port 191 passes through an outlet port 192 and into the reservoir 69.

The automatic nebulization cartridge 117 is provided with an outlet port 193 which is connected to a fixed nebulizer orifice of a suitable size such as 0.024 inches. The orifice 194 is connected to the nebulizer service socket 54 which is connected to the nebulizer 58 as hereinbefore described.

Now turning to the oscillatory volumetric ventilator module 14, the inlet port 48 of the demand CPAP cartridge 49 is connected to a source isolation check valve 196 through which gas passes and is supplied to a stabilization reservoir 197. The stabilization reservoir 197 is connected to the inlet port 198 of a time cycled on/off switch 199 of a rotary type. The outlet port 201 of the switch 199 is connected to an inlet port 202 of a normally closed inspiratory time cartridge 203. Gas is also supplied to an inlet port 204 of a normally open expiratory time cartridge 206. The cartridge 203 is provided with an adjustable spring 205 for biasing the opening of cartridge 203. Gas from the inlet port 204 of cartridge 206 normally flows through the cartridge through an outlet port 207 to one side of an inspiratory isolation check valve 208 which is connected to an adjustable metering valve 209. The metering valve 209 is connected to the servo port 211 of the inspiratory time cartridge 203. The metering valve 209 is also connected to the entrainment reservoir 69. The outlet port 213 of the inspiratory timing cartridge 203 is connected to an adjustable flow pressure metering valve 214. The metering valve is connected to a ventilator output low pressure check valve 215. The check valve 215 is connected to the check valve 113. The metering valve 214 is also connected to one side of an inspiratory isolation check valve 216. The check valve 216 is connected to an inlet port 217 of an adjustable metering valve 218. The metering valve 218 is connected to a servo port 219 of the expiratory time cartridge 206. The metering valve 218 is also connected to the entrainment reservoir 69 in the same manner as the metering valve 209.

In the universal breathing circuit 16, a generally cylindrical body 221 is provided which has formed therein a restricted venturi-like passageway 122. The nozzle or jet 84 is disposed so that the gases jetting therefrom travel axially of the venturi-like passageway 222. An additional cylindrical body 223 is provided which encircles the body 221 and forms space 224 between the body 223 and the body 221. The inlet port 107 is formed in the body 223 and is utilized for introducing gases into the annular space 224 provided between the bodies 221 and 223. One end of the body 223 is closed whereas the other end opens into the patient's airway represented by the balloon-like configuration 226. The body 221 is provided with an expiratory gate 227. The body 223 has connected thereto an exhalation valve assembly 228. The valve assembly 228 is provided with a servo port 229 which is connected to the nozzle inlet 84. The servo port 229 is also connected to a phasing orifice 231, which is open to ambient.

The demand CPAP cartridge 49 is provided with an adjustment knob 244 for adjusting the pressure on a spring 242 for varying the opening pressure required for the cartridge 49.

Operation of the ventilator as shown in FIG. 1 incoming gases such as oxygen and air are delivered from the source of gas to the oxygen blender 21 in the power control module 11. A flow of mixed gases is delivered at the outlet 24. When insufficient gas is being delivered by the blender 21, the blender 21 will bypass the flow of gas from the outlet port 24 to the port 27 and thence through the outlet port 26 to introduce gas into the servo inlet 33 of the bypass cartridge 32 causing it to open and to permit a flow of one of the gases, either air or oxygen through the bypass cartridge and out the outlet port 31 and into the lines or circuits downstream of the blender 21. Generally a flow of gas around the components of the blender 21 will occur when one of the two gas sources becomes unreliable or is exhausted. The isolation valves 36 and 37 prevent backflow between the oxygen and air inlets from the sources of gas.

When gas is being bypassed by the blender, a visible indication is given by metering gases through the metering valve 38 and supplying the same to the bypass indicator 39. Gas is also supplied to a bleed off orifice 41 which can be supplied to an audible alarm if desired.

The gas which is supplied from the power control module is supplied to the transport service module 13 to the regulator 46. The pressure regulator 46 provides a means for establishing an optimal pressure for a stable oscillatory frequency control with the optimal pressure being normally from 45 to 55 psi.

Regulated gas under pressure from the regulator 46 is supplied to the master oscillator on-off switch 92 forming a part of the oscillatory diffusion module 12. As soon as the master switch 92 is turned on, regulated gas under pressure is delivered through outlet post 93 to the reservoir 121 and to the inlet port 122 of the oscillator cartridge 123. The oscillator cartridge 123 is normally open with a pneumatic opening and closing differential. Regulated gas is delivered from the oscillator reservoir 121 which serves as a surge/stabilizer to the oscillator cartridge 123 which is normally open and gas is delivered through the outlet port 136 to the inlet of the oscillator frequency inspiratory (flow on) valve 139 through the oscillator control isolation check valve 137.

Also when the oscillator on-off switch 92 is turned on, regulated gas in addition to being supplied to the oscillator cartridge 123 is also supplied to the inlet port 124 of the autoload cartridge 126. Regulated gas is also delivered against the outlet of the reset check valve 127 and to the inlet of the loading orifice 128. As soon as gas is supplied to the inlet port 124 of the autoload cartridge 126, gas flows through the normally open autoload cartridge 126 through the outlet port 131 and directly loads the diaphragm of the interrupter cartridge 88 through the servo port 133 and provides substantially instantaneous closing of the interrupter cartridge 88. This prevents a surge of gas through the oscillator cartridge 123 into the circuit connected to the main venturi nozzle 84 negating a potential oscillator stall and a large stroke volume at the physiological airway. The loading orifice 128 for the autoload cartridge 126 is sufficiently restrictive so as to allow a two to three second servoing time before passing sufficient gas to the servo port 129 to servo the autoload diaphragm to the off position. Therefore, it can be seen that the autoload cartridge 126 servos the interrupter cartridge 88 closed when the master switch 92 is rotated to the "on" position. The oscillator cartridge 123 remains in the expiratory phase until the timing circuit associated with the interrupter cartridge 88 enters its programmed diffusion (inspiratory) phase with the normal ramping function. The autoload cartridge 126 remains closed until the source of gas pressure supplied to it through the master on-off switch 92 is turned off. At that time, servoing gases are then dumped from the autoload cartridge 126 out through the reset check valve 127 to permit the autoload cartridge to return to its normally open position.

At the time that the master on/off switch 92 is turned on, regulated gas is also delivered through the timing isolation check valve 94 to the timing regulator 97 which as hereinbefore explained, delivers gas at a controlled pressure as, for example, at 30 psi. This regulator is used to prevent a surge in case of an explosive decompression as, for example, if the ventilator is aboard an airborne vehicle during such an event. Gas under 30 psi pressure is delivered from the outlet 98 into the inlet port 99 of the timing cartridge 101. The timing cartridge 101 is normally open and therefore when gas is delivered into the inlet port 99, gas is delivered to the outlet port 176 to the timing manifold 177. When the regulated gas of 30 psi is delivered into the timing manifold 177, 30 psi timing gases are distributed to a number of locations. Timing gas is delivered to the servo port 181 of the automatic nebulization cartridge 117. Timing gas is also delivered to the servo port 182 of the timing reset cartridge 183. Timing gas is also delivered to the ramping circuit for the interrupter cartridge 88 which includes the ramping isolation check valve 132 and the ramping orifice 178. Timing gas is also supplied from the timing manifold 177 to a diffusion-volumetric exchange timing circuit which includes the timing isolation check valve 184, the volumetric exchange valve 186 and the diffusion interval valve 189. Timing gas travels through the timing isolation check valve 184 and the valves 186 and 189 to the inlet port 191 of the timing reset cartridge 183. Timing gas is also delivered to the reservoir refill bleed orifice 179.

It should be appreciated that when the master switch 92 is rotated to the on position, the ramping circuit for the interrupter cartridge 88 is charged by the autoload cartridge slightly ahead of flow into the master timing circuit from the timing cartridge 101.

As the master timing circuit is pressurized from the timing manifold 177, the normally open automatic nebulization cartridge 117 is servoed closed by the entrance of timing gas through the servo port 181. Similarly, the normally open timing reset cartridge 183 is servoed closed through the entrance of gas through its servo port 182. The ramping circuit for the interrupter cartridge 88 is serviced by introducing timing gas flow against the ramping orifice 178 and to the inlet of the ramping isolation check valve 132. Timing gas enters the diffusion-volumetric exchange interval timing circuit through the timing isolation valve 184 and reservoir refill gas is delivered by the timing cartridge 101 through the fixed timing reservoir refill orifice 179.

Timing gas continues to flow through the master timing circuit from the timing manifold 177 through the timing isolation check valve 184 and through the valve 186 which provides a metered flow of gas that is supplied to the diffusion interval valve 189 which provides a further metered gas flow to the inlet port 191 of the timing reset cartridge 183. Metered gas from the valve 186 is also supplied through the timing reservoir 187 and into the servo port 188 of the timing cartridge 101. The timing cartridge 101 is normally open and when the pressure behind the diaphragm rises a yield point the timing cartridge 101 is moved beyond to a closed position which instantaneously interrupts the flow of gas into the master timing circuit. The inspiratory phase commences at this point which also can be characterized as a phasic sequencing of the diffusion interval. The diffusion interval (inspiratory phase) is initiated by depressurization of the master timing circuit through the fixed timing reservoir refill orifice 179 which bleeds the gas from the master timing circuit into the reservoir 69. The exact timing of the inspiratory phase of the diffusion interval starts when the timing reset cartridge 183 opens after the gas from behind the diaphragm has bled down sufficiently through the manifold 177 and through the reservoir refill orifice 179. The opening of the timing reset cartridge 183 permits gas to bleed down from the diffusion interval valve 189 through the timing reset cartridge 183 into the entrainment reservoir 69. The length of the inspiratory phase or diffusion interval is determined by the size of the orifice in the volumetric exchange valve 186.

Thus, it can be seen that the servoing gases which are produced by the loading and unloading of the timing cartridge 101 pass through independent irreversible pathways to provide infinite inspiratory-expiratory ratios with the times for the inspiratory and expiratory phases being determined by the positioning of the adjustable valves 186 and 189.

Other than the control provided by the timing cartridge 101, manual initiation of the inspiratory phase can be accomplished by operating the manual inspiration push button 76. When this is accomplished regulated gas is delivered from the regulator 46 through the manual inspiration valve 74 to the inlet port 78 of the failsafe cartridge 79 which is normally open and permits regulated gas to be delivered through its outlet port 81 to the nozzle 84 to deliver gas into the main venturi-like passageway 122 and into the airway of the patient. By operation of the manual inspiration valve 74, it is possible to hand pace the inspiratory and expiratory phases. This manual inspiration circuit provides means for manually inflating the lungs of a patient through pressure regulated circuitry associated with the failsafe servo cartridge 154. Because of this feature, the peak delivery pressure of the gases supplied to the patient will not exceed that programmed for oscillatory delivery. Thus, there is provided an important safety factor for the patient. By operation of the manual inspiration valve 74, it is possible to hand pace the inspiratory and expiratory phases.

The master timing means hereinbefore described controls the opening and closing of the interrupter cartridge 88. Because the pressures downstream of the oscillator cartridge 123 are too low to operate a pneumatic timing circuit, an independent timing circuit has been created and servoed by a normally open timing cartridge 101.

It can be seen that the periodic master timing circuit hereinbefore described provides programmable means for infinite inspiratory-expiratory ratios, or volume exchange ratios. Closing the diffusion interval metering valve 189 will produce an infinite oscillatory interval while closing the volumetric exchange metering valve 186 will produce an infinite non-oscillatory interval. Whichever valve is closed first will command.

Regulated oscillatory gases are supplied by the oscillator cartridge 123 and its associated timing circuitry. Oscillation of the oscillator cartridge 123 is a function of the intermittent loading of the oscillator timing circuit. The normally open oscillator cartridge 123 delivers gas to the interrupter cartridge 88 from the outlet port 136 of the oscillator cartridge 123 to the inlet port 134 of the interrupter cartridge 88. As pressure rises in port 134, flow is introduced through the oscillator control check valve 137 into the inlet port 138 of the manifold of the metering valve 139 so that unmetered gas is delivered through the outlet port 141 to the inlet port 142 of the valve 143. Metered gas is delivered from outlet port 144 of the metering valve 139 to the servo port 146 of the oscillator cartridge 123. When pressure rises sufficiently in the servo port of the oscillator cartridge 123 as, for example, to approximately 20 psi, the diaphragm of the oscillator cartridge will cause movement of the valve member to interrupt the flow of regulated gas through the oscillator cartridge 123 to the interrupter cartridge 88. When the servoing pressure within the oscillator cartridge 123 drops below a predetermined pressure as, for example, 10 psi the valve member of the oscillator cartridge will again open.

The oscillator cartridge has approximately a 10 psi opening and closing differential which serves as an air cam during rapid oscillation for effective translatory opening and closing. Stroke volume is increased by a more complete opening and closing travel of the valve member in the oscillator cartridge 123 in the time permitted. This is particularly important for maximum amplitude (stroke volume) at each frequency. The opening and closing differential is accommodated by the difference in piston effect between the closed (end of the poppet valve only) and open positions (a much larger area of the diaphragm).

The oscillatory frequency is a factor of the inspiratory/expiratory ratio during oscillation of the gate valve member or poppet that is in the oscillator cartridge 123. The metering valve 139 determines the time required to servo the diaphragm off by metering flow to the servoing diaphragm. The flow of gas through the metering valve 143 determines the bleed down rate of the diaphragmatic servoing pressure and determines how long the oscillator cartridge gate valve remains closed.

Oscillator stall (open oscillator cartridge without cycling) is eliminated by the ambient venting of servo gases through the metering valve 143 during the period when the interrupter cartridge is closed. This in effect creates a "pneumatic clock" during idle with the rate of oscillator cartridge opening and closing (oscillation) being determined by the position of the inspiratory and expiratory metering valves 139 and 143.

The oscillator control isolation check valve 137 in conjunction with the oscillator loading circuit venting it through the metering valve 143 stabilizes the oscillatory frequency and enhances oscillator stroke volume. The oscillator control isolation check valve 137 has an opening pressure of approximately 3 psi providing a positive initial opening pressure and directing diaphragmatic bleed down through the metering valve 143.

During the time that the diaphragm on the oscillator cartridge 123 is being loaded, the servoing gases which are passing through the oscillation control or isolation check valve 137 pass through the valve 139 and overwhelm the metering orifice of the inspiratory metering valve 143 while at the same time loading the diaphragm with metered gas through the inspiratory metering valve 139. In this connection, it should be appreciated that the diaphragmatic loading pressure gradient is substantially higher than the bleed down gradient. This characteristic limits high oscillatory rates. By overwhelming the metering orifice of the valve 143 during the diaphragmatic loading of the oscillator cartridge 123, the effective loading pressure required is reduced, thereby lengthening the inspiratory time. However, with the adjustable valves 139 and 143 which are provided, mandatory positive inspiratory/expiratory ratio is mandated during all expiratory flow. Metering valve 143 can be of a smaller adjustable caliber valve than the inspiratory flow on metering valve 139 to create a more positive inspiratory/expiratory ratio to reduce a physiological constant positive airway pressure (CPAP) by lengthening the period of oscillator flow off time.

As oscillatory frequencies are reduced below 100 cycles per minute to volumetric ventilation, positive inspiratory/expiratory ratios are increased as the metering orifice caliber becomes smaller than the expiratory metering orifice. For example, the expiratory orifice provided by the valve 143 becomes ineffective and the inspiratory/expiratory ratio is under the control of the inspiratory metering orifice. As the phasic frequency is reduced, the inspiratory/expiratory ratio becomes more positive, e.g.: 1.4 to 1.5 at slow rates with ever-increasing stroke volumes. Thus, it can be seen that the oscillatory timing circuit associated with the oscillator cartridge 123 provides a means for stabilizing oscillatory function as well as to prevent the clinician or operator from establishing a conflicting clinical program beyond normal physiological limits of the patient over a wide range of oscillatory frequencies.

The oscillator timing circuit associated with the oscillator cartridge 123 in conjunction with an opening and closing differential enables a wide range of oscillatory frequencies. As the regulated gases enter the normally open oscillator cartridge 123, they are delivered into the normally open interrupter cartridge 88 and then caused to flow against a downstream resistance with oscillatory operational pressures averaging five to fifteen psi which is in comparison to the 35 to 50 psi operational pressures in conventional timing circuits. The oscillator reservoir 121 increases stroke volume by creating a more positive valve opening with a larger metering orifice at a given frequency. The inspiratory/expiratory ratio control which is provided allows for a more controlled bleeddown of the oscillator timing circuit affecting both rate and stroke volume. During loading, the mean servoing pressure is higher. During (depressurization) unloading gases flow through both metering valves 139 and 143 creating a depressurization under lower mean pressure gradients, thus decreasing oscillatory frequency and modifying residual systemic pressures.

Thus, it can be seen that the oscillator 123 with its timing circuit will deliver regulated gases at a pulse rate determined by the oscillator preprogrammed frequency. The outflow from the interrupter cartridge 88 from the outlet port 87 is delivered to the inlet port 86 of the normally open failsafe cartridge 79. Oscillatory gases are delivered from the outlet port 81 of the failsafe cartridge 79 to the venturi service socket 82 and through the nozzle 84 into the main venturi-like passageway into the patient's airway 226.

The interrupter cartridge 88 provides a means for controlling the diffusion interval and allows volumetric diffusion respiration to occur by programming periodic oscillation.

Locating the interrupter cartridge 88 downstream from the oscillator cartridge 123 provides antisurge protection which would not be present if the interrupter cartridge were located upstream of the oscillator cartridge 123.

It has been found that if interrupter cartridge 88 is opened too rapidly, an oscillator stall can occur because the loading pressures at the inlet port 134 will drop below critical oscillator diaphragm servoing levels. The ramping circuit which has been provided for the interrupter cartridge 88 prevents oscillator stall and creates a soft start of oscillation and causing a gradual oscillatory increase in stroke volume at the physiological airway of the patient.

As pointed out previously, timing gases are delivered to a ramping isolation check valve 132 and to the metering valve 178. During the time that the diaphragm of the interrupter cartridge 88 is being loaded through the servo port 133, timing gases are allowed to surge into the circuit for rapid closing of the interrupter cartridge 88. During opening of the interrupter cartridge 88, bleed down of gases from the diaphragm is metered through the adjustable ramping metering valve 178 to retard the opening of the interrupter cartridge 88 and to provide a "gentle" opening which obtunds oscillatory amplitude during the transitional opening.

The interrupter cartridge 88 can be servoed closed by gases from the autoload cartridge 126 as hereinbefore described. It also can be servoed closed by pressurization from the interrupter (master) timing circuit.

Thus, it can be seen that when the master on/off switch 92 is turned on the interrupter cartridge 88 will be servoed into a closed position by the autoload cartridge 126 and will open softly to permit regulated oscillatory gases to be supplied by the oscillator cartridge 123 through the interrupter cartridge which is opened gently under the control of the timing circuitry hereinbefore described to deliver gases to the patient airway which during the inspiratory phase will supply pulses of gas under pressure to provide an oscillatory ramping pressure rise as depicted in the curves shown in FIG. 2 and as hereinafter described more in detail.

The oscillatory diffusion module 12 supplies gases to three sockets, the venturi power socket 82, the nebulizer power socket 54, and the reservoir power socket 64. All of the programmed inspiratory gases are delivered through the venturi socket 82. The nebulizer power socket 56 delivers automatic regulated gases and manually controlled non-regulated gases.

The automatic nebulization cartridge 117 receives regulated gas downstream from the timing isolation check valve 94 from which it is supplied to the input port 116. The nebulizer cartridge 117 is servoed to an open position just immediately prior to the time the ventilator enters the inspiratory phase or diffusion interval and delivers source gas from the outlet port 193 to the inlet of the fixed nebulizer orifice 194. The fixed nebulizer orifice 194 meters gas for driving the nebulizer/humidifier 58 by supplying such gases to the nebulizer socket 54 and supplying the same to the nebulizer/humidifier 58. The automatic nebulization can be overridden by a supplemental or manually adjusted circuit.

Regulated source gas is supplied from the inlet 44 to the regulator 46 where it is supplied to the inlet port 51 of the adjustable nebulizer control valve 52. Metered gas is supplied at the outlet port 53 from the valve 52 and is supplied to the nebulizer socket 54. In this way it can be seen that a nebulizer flow leading the inspiratory flow of oscillatory gases during automatic operation of the ventilator is provided. In addition, a common circuit is provided for automatic and manual continuance of sources of nebulizer/humidifier drive gases.

The reservoir power socket 64 delivers ventilatory and timing gases from the scavenger circuit. Scavenged gases are delivered from the outlet 147 of the valve 143 from the port 192 of the timing reset cartridge 183 and from the outlets of the metering valves 209 and 218 of the oscillatory volumetric ventilator module 14. Gases are also scavenged from the outlet 164 of the failsafe alarm calibration metering valve 163. The automatic reservoir refill orifice 179 delivers gas into the scavenge circuit during the volumetric exchange interval. A manually adjustable source of the reservoir refill gases are delivered from the regulator 46 to the inlet port 61 of the reservoir control metering valve 62. Metered gases are delivered through the output port 63 of the reservoir control valve 62 for delivery to the reservoir power socket 64.

From the reservoir refill circuit hereinbefore described it can be seen that means is provided for automatic refilling of the reservoir during the volumetric diffusion interval or inspiratory phase. Timing gases are delivered during this time through the timing/reservoir refill orifice 179 with the rate of delivery being determined by the size of the orifice 179.

Operation of the oscillatory volumetric ventilator module 14 may now be described. Gas is received from the input 44 of the regulator 46 which is supplied to the input port 48 of the demand CPAP cartridge 49. It is also delivered through the source isolation check valve 196 and through the stabilization reservoir 197 to the inlet 198 of the time cycled master switch 199. Gas is delivered from the outlet 201 of the switch 199 and is supplied to the inlet port 202 of the normally closed inspiratory time control cartridge 203 and also to the inlet port 204 of the normally open expiratory time control cartridge 206. Since the expiratory time control cartridge 206 is open, gas flows from the inlet port 204 through the outlet port 207 and passes through the inspiratory isolation check valve 208 through the manifold of the metering valve 209. Gas then enters the servo port 211 of the normally closed inspiratory time control cartridge 203. As the pressure against the diaphragm of the inspiratory control cartridge 203 increases, the cartridge 203 is moved to the open position and an inspiratory flow of gas commences with flow through the inlet port 202 to the outlet port 213. It will be noted that the gas flow through the cartridge 203 is reverse to that which is conventional, that is, gas from the source enters to the rear of the gate valve and applies a constant pressure against the diaphragm to provide a sine wave opening of the gate valve. The opening pressures can be adjusted by the springloading provided by the spring 205. Gas flowing from the outlet 213 of the inspiratory time control cartridge 203 enters the manifold of the flow pressure control metering valve 214. Gas then flows through the expiratory isolation check valve 216 into the inlet port 217 of the manifold of the expiratory time control and metering valve 218. Gas from the manifold of the expiratory time control metering valve 218 enters the servo port 219 of the expiratory time control cartridge 206. When a sufficient pressure rise has been created against the diaphragm, the normally open expiratory time control cartridge 206 is moved to a closed position and the inspiratory time circuit is terminated. With gas flow into the inspiratory circuit cutoff, inspiratory time has started. As gas is bled from the inspiratory circuit through the metered outlet from the metering valve 209, within a certain period of time, as determined by the rate of bleeddown, the inspiratory time control cartridge 203 moves to its normally closed position to terminate the inspiratory interval. Upon termination of the inspiratory interval, pressurization of the inspiratory circuit ceases. The length of the expiratory interval is controlled by the bleeding of servoing gas from the metered outlet of the metering valve 218. As soon as sufficient bleeddown has occurred, the normally open expiratory control cartridge 206 opens and the expiratory time is terminated. Gas purged from both the inspiratory and expiratory timing circuits from the metered outlets of the metering valves 209 and 218 is delivered to the entrainment reservoir 69.

From the foregoing, it can be seen that an oscillatory volumetric circuit 14 with an infinite inspiratory/expiratory ratio has been provided. The frequency of oscillation increases with flow through rates in the metering valves 209 and 218.

The flow pressure metering valve 214 receives inspiratory gas from the inspiratory time control cartridge 203 and delivers a metered flow through a low pressure check valve 215 into the inlet port 78 of the failsafe cartridge 79. Also during inspiration, gas is supplied from the flow pressure metering valve 214 through a fixed metering orifice (not shown) through the servo isolation check valve 135 to the ramping circuit of the interrupter cartridge 88 by supplying gases to one side of the check valve 132 and to the servo port 133 of the interrupter cartridge 88.

Whenever both the diffusion master switch 92 and the volumetric master switch 199 are "on", the volumetric ventilator will command by loading the diffusion ventilator timing circuit into an expiratory or volumetric exchange interval. When integrated operation between the diffusion and volumetric ventilators is functioning, the delay between tidal delivery from the volumetric ventilator and start of oscillatory stroke volumes by the diffusion ventilator is controlled by the interrupter ramping circuit. The longer it takes servoing gases from the volumetric ventilator to bleed out of the oscillator ramping circuit, the longer the post-inspiratory pause before oscillatory stroke volumes commence. The ramping orifice provides a means for adjusting the post-inspiratory pause.

The volumetric ventilator provides a controlled oscillation at frequencies to well above 100 cycles per minute. This is mechanically accomplished by a timing circuit which controls a reverse flow normally closed spring balanced inspiratory time control cartridge 203.

The oscillatory volumetric ventilator module with CPAP and fail-safe alarm includes the demand CPAP cartridge 49. The demand CPAP cartridge 49 is provided with a control knob 244 which can be utilized for adjusting the pressure applied to the diaphragm of the cartridge 49 through a spring 242. The servo port 109 of the demand CPAP cartridge 49 is connected to the airway pressure socket 104 of the patient so that the patient on demand can cause opening of the cartridge to permit gases to flow from the inlet 48 through the outlet 112 and through the CPAP output low pressure check valve 113 and through the fail-safe cartridge 79 to the main venturi socket 82 and to the nozzle 84 and into the airway of the patient. A further drop in airway pressure accelerates the flow while a pressure rise in airway to the patient retards the flow through the CPAP cartridge 49 and as the airway of the patient is filled, the pressure rises to supply gas under pressure to the servo port 109 to cause the demand CPAP cartridge 49 to retard and close. The check valve 113 prevents backflow from oscillations when CPAP is not employed. The demand CPAP cartridge 49 provides a means for rapid inspiratory physiological response to minimize the work of breathing while maintaining a reliable constant positive pressure without excessive expiratory flow resistance. The pneumatic clutching action of the venturi which is controlled by the pressure drop across the venturi jet 84 is used to establish a positive end expiratory pressure against the physiological airway. The graded expiratory resistance within the throat of the proximal venturi-like passageway 122 provides a pressure rise above the selection made with the demand CPAP cartridge to terminate demand flow during passive physiological exhalation. Any oscillatory pressure rise at the proximal airway above the selected CPAP value automatically retards flow from the CPAP cartridge 49 and superimposes the oscillatory pattern provided by the oscillatory diffusion module 12.

In order to control oscillation against physiological structures with low compliance, the CPAP dampening circuit is provided in which gas flow from the outlet port 112 delivers gas to the adjustable dampening orifice 111. Flow from the dampening orifice 111 is delivered to the sensing or servo port of the CPAP cartridge 49. By introducing an accelerated metered flow of gas from the demand CPAP cartridge 49 through the CPAP dampening orifice 111 during dynamic demand inspiration, any constant or lesser flow of gas during the maintenance of a positive end expiratory pressure creates a snubbing action lessening tendencies to oscillate against the physiological resistance of the patient.

The demand CPAP cartridge 49 provides a means for accommodating spontaneous inspiratory demand. Two distinct oscillatory patterns can be employed independently or serially upon the basic flow provided by the CPAP demand cartridge 49. Volumetric diffusion respiration can be superimposed upon the flow provided by the CPAP cartridge 49 allowing spontaneous demand breathing during an extended volumetric exchange interval. Additionally, the oscillatory diffusion module 12 can establish a continuous rapid oscillation with or without CPAP to control the partial pressure of oxygen in the arterial blood. This stroke volume can be periodically topped with a tidal volume delivered by the oscillatory volumetric ventilator to control the partial pressure of carbon dioxide in the arterial blood and the pH by providing a mass pulmonary exchange. This is accomplished by selecting a constant diffusion interval on the diffusion module 12 and by programming a desired tidal volume and delivery time on the volumetric module 14. This is made possible by servoing of the diffusion module ramping circuit with the volumetric module during delivery of a tidal volume.

Combination and serialized programming can be obtained by interlocking and sequencing of the three timing circuits, the oscillatory, periodic and volumetric respirator timing circuits hereinbefore described.

The ventilator of the present invention includes a pneumatic alert/fail-safe system to avert trauma should a mechanical or human failure occur. The alert/fail-safe servo cartridge 154 is provided with a control knob 173 for adjusting the loading for the cartridge. A source of the gas is normally delivered to the inlet port 151 of the main pressurized calibration metering valve 152 and to one side of the alarm or reset check valve 156. This source gas is metered through the valve 152 into the servo port 153 of the failsafe servo cartridge 154. The source of gas for the servoing of the fail-safe servo cartridge 154 is taken internally from the main source of ventilatory gases being delivered to the venturi nozzle 84. This source of gas is taken from the port 86 which is connected to the port 81 connected to the venturi socket 82. The opening pressure and the alarming time of the fail-safe servo cartridge 154 are dependent upon the pressure of the source servoing gas, the spring load against the valve gate and the back pressure in the scavenge circuit. Actuation of the alert/fail-safe servo cartridge 154 occurs when there is a sustained pressure rise in the gas being delivered to the patient's proximal airway. A transient pressure rise associated with an oscillation is dampened out by the orifice in the metering valve 152. When a sustained pressure rise occurs, the failsafe servo cartridge will be moved to an open position and gas will be supplied through the port 158 to operate the fail-safe indicator 159 and the alarm 167.

The demand CPAP servo 49 accelerates the gas flow as essential pressures fall below programmed values to satisfy physiological inspiratory demand. The same type of pressure drop will be manifested if a proximal airway disconnect occurs with respect to the patient or if the CPAP/monitoring sensing line becomes disconnected at any point. As the CPAP flow accelerates, pressures in the venturi service circuit are increased with an associated in the source pressures delivered to the alert/fail-safe servo cartridge 154.

When the source gas pressure rise is sustained above the programmed opening pressure for the fail-safe servo cartridge 154, the fail-safe servo cartridge 154 is opened by servoing gases behind the diaphragm. Gas flow within the fail-safe servo cartridge and to the fail-safe circuit is metered through the metering valve 152, the failsafe servo cartridge inlet port 157 and outlet port 158 to the pneumatic fail-safe indicator 159 and also to the servo port 161 of the fail-safe cartridge 79 and also to the inlet port of the fail-safe alarm calibration orifice 163. From the outlet port 164 of the calibration orifice 163 servoing gas enters the inlet of the alarm isolation and check valve 166 to activate a pneumatic alarm 167. In addition, servoing gas from the outlet of the metering valve 163 is directed through the alarm balance orifice 168 into the scavenging circuit emptying into the entrainment reservoir 69. Thus it can be seen that the alert/fail-safe system is activated whenever the pressure of breathing gases flowing to the venturi jet 84 reaches and sustains a pressure above that programmed by the failsafe servo cartridge 154. The failsafe cartridge 79 is a normally open reverse flow pneumatic cartridge. Dual inlets 78 and 86 provide collateral inlet flow from all ventilatory sources. A "lock up" of the plunger or by the valve poppet is prevented by employing an orifice (not shown) through the poppet stem. Inspiratory gases are delivered from the outlet 81 of the fail-safe servo to the venturi socket 82.

Should the pressure of respiratory gases be sustained beyond programmed limits, the fail-safe cartridge 79 will be moved to a closed position at the same time visible and audible alerts are given by the indicators 159 and 167. When the fail-safe cartridge 79 is moved to a closed position as in the case of a major failure and in turn inducing the high pressure in the respiratory gas circuits, the pressure of gases through the fail-safe servo 79 increases causing the alarm to be sounding with increasing amplitude.

Whenever pressure is higher at the outlet of the reset check valve 156 and inlet port 151, a flow through the adjustable orifice of the mean pressure metering valve 152 occurs causing a pressure rise against the servoing diaphragm and in the antisurge pressure balance reservoir 155. If the pressure rises above the servoing pressure, the fail-safe servo cartridge 154 opens and the alert/fail-safe system hereinbefore described becomes dynamic. The mean servoing pressure can be controlled by adjusting the mean pressure rise orifice in the valve 152. The smaller the orifice, the more time is required to servo open at pressures above programmed levels.

During oscillatory diffusion or volume delivery in the ventilator, it is possible for a mechanical failure to occur such as the opening of the flow cartridges well beyond programmed limits. A failure of a flow cartridge would cause a precipitous rise in flow and pressure of gases in the venturi-like passageway 122. This could produce proximal airway pressures beyond physiological limits. Should such an event occur, the alert/fail-safe system would alarm and would reduce pressures in the airway below traumatic levels. Therefore, any mechanical failure producing a runaway flow condition will alarm and be automatically locked out. The fail-safe pressure rise produces a unique means of pressure limiting if limits are exceeded.

Once a lockout has occurred, all programming will remain interrupted until the cause of the lockout has been corrected. In most cases, servoing gas locked up within the failsafe servo cartridge 154 will have to be manually released to reestablish functioning of the ventilator. This is accomplished by dumping the servo circuit through the outlet port 172 of the valve 152 by operation of the normally closed manually actuated reset push button 171 to ambient. Should the cause of the lockout not be corrected before reset, an immediate lockout will be repeated.

The alert/lockout system used in the present ventilator utilizes source gas pressures for causing servoing of the failsafe servo cartridge 154 rather than using traditional breathing circuit pressures. In addition, the alert-lockout system utilizes mean pressures rather than relying on a pressure rise or a time constant.

The universal breathing circuit 16 includes an encapsulated venturi as hereinbefore described which provides a means of rapid pressure rise and drop at the physiological airway during rapid oscillation. During exhalation from the patient's airway, gases flow around the distal end of the venturi assembly and reach ambient through the exhalation valve 228. The exhalation valve 228 is normally open and is kept in phase with the stroke volume delivery by the adjustable phasing orifice 231 connected to the servo port 229.

The use of the normally open exhalation valve reduces the work of breathing in case of total failure of gas delivery by acting as a fail-safe device for satisfying physiological demand. The exhalation valve cannot mechanically lock up the physiological airway because it parallels the venturi passageway which is in communication with the expiratory gate 227.

The universal breathing circuit 16 in the present invention has numerous advantages. It prevents rebreathing of exhaled gases. It permits monitoring of the proximal airway pressure. It eliminates the potential for the lockup of an exhalation valve.

In FIG. 2 there are shown the curves resulting from a theoretical stabilized patient on intermittent percussive ventilation (I.P.V.) with demand constant positive airway pressure (CPAP). The curves in particular show the oscillatory ramping up of pressure during the diffusion interval (inspiratory phase) and the percussive clutching which occurs in the venturi-like passageway as the patient's airway is filled. The functional residual capacity (F.R.C.) increases and decreases as indicated during the inspiratory and expiratory phases. A CPAP of 5 cm $H_2O$ is shown.

In FIG. 3 there is shown another embodiment of the invention which is substantially simpler in construction than the embodiment of the invention shown in FIG. 1. It consists of a power control module 261, a transport service module 262, an alarm control module 263, a volumetric diffusion respirator module 264 and a breathing circuit 266. The power control module 261 is substantially identical to the power control module 11 disclosed in the previous embodiment and therefore it will not be described in detail. As can be seen, the various components of the power control module are identical to the components disclosed in the previous embodiment. In addition, the mode of operation is the same.

The transport service module 262 consists of two regulators 271 and 272 in which regulator 271 can be characterized as an oscillator pressure regulator and the regulator 272 can be characterized as a time cycle regulator. Gas is supplied from the outlet 24 of the oxygen blender 21 of the power control module to an aspirator power socket 273 of the transport service module 262. In addition, unregulated gas is supplied through the inlet 274 of the master on/off switch 276. The master on/off switch 276 is provided with a control knob 277 so that the master on/off switch can be switched manually "on" or "off" by use of the knob 277. When the master on/off switch 276 is turned, on, regulated gas is supplied from the inlet 274 to the outlets 278 and 279. Gas is supplied from, outlet 278 to the inlets 281 and 282 of the regulators 271 and 272. When the switch 276 is in the off position gas is supplied from the inlet 274 through an outlet 279 and through a check valve assembly 280 for a purpose hereinafter described.

The oscillator pressure regulator can be set for a predetermined pressure and from a range of 0 to 100 psi; for example, 50 psi for adults and 25 psi for babies. Regulated gas is supplied at the desired pressure from the oscillator pressure regulator 271 through its outlet 283. Gas from the outlet 283 is supplied through an adjustable gauge orifice 284 to a gauge 286 which supplies a visual reading of the oscillator operating pressure. Regulated gas is also supplied to the inlet 287 of a pneumatically-controlled flow oscillator cartridge 288. The flow oscillator cartridge 288 forms a part of the alarm/control module 264. The flow oscillator cartridge 288 is provided with an outlet 289 which is connected through an oscillator inspiratory isolation check valve assembly 291 to the inlet 292 of an oscillator inspiratory time on needle valve 293 which is carried by the flow oscillator cartridge 288. The adjustable needle valve 293 is provided with an outlet 294. Gas which is metered through the needle valve 293 is supplied to a servo port 296. Gas supplied to the servo port 296 servoes the flow oscillator cartridge 336 into the closed position to interrupt the flow of gas from the inlet port 287 to the outlet port 289. This interrupts the flow of servoing gas to the servo port 296. Gas behind the diaphragm of the flow oscillator will then flow out of the servo port 296 to the inlet 297 to the oscillator expiratory time off needle valve 298 and then through its outlet 299. The outlet 299 is connected to an inlet 301 of an oscillator timing reset cartridge 302. The oscillator timing reset cartridge 302 carries the oscillator expiratory time off needle valve 298. The inlet 301 in the oscillator timing reset cartridge is in the open position and is in communication with an outlet 303 which is connected to an inlet 304 of an interval phasing cartridge 306. The inlet 304, when the interval phasing cartridge is in the open position, is in communication with an outlet 307. The outlet 307 is connected through a frequency band adjustment needle valve 308 which is connected to a servo port 309 of the oscillator timing reset cartridge 302. At the same time that the gas is delivered to the frequency band adjustable needle valve 308, gas is also supplied to a service socket 311. A fitting 312 is mounted in the service socket 311 and is connected to an entrainment gate 313. The socket 313 is connected into an entrainment reservoir 314. Regulated gas in addition to flowing through the oscillator inspiratory isolation check valve 291 flows to the right to an inlet 316 of an oscillatory amplitude needle valve 317 which is carried by the interval phasing cartridge 306. The metered gas is supplied to the outlet 318 of the oscillatory amplitude needle valve assembly 317 which is connected to an service socket 319. An inlet fitting 321 is mounted in the service socket 319 and is connected to the venturi jet 322 of a venturi assembly 323. Thus it can be seen that by adjustment of the oscillatory amplitude needle valve assembly 317 it is possible to adjust the amplitude of the oscillations in the metered gas. Even though gas is being supplied to the venturi jet 322, sufficient back pressure is developed so that gas is also supplied through the oscillator inspiratory isolation check valve assembly 291 for metering the gas. This metered gas is supplied through the isolation inspiratory time off needle valve assembly 298 but the gas can go no further because the oscillator timing reset cartridge 302 is now in a closed position because of the gas previously supplied to the servo port 309 to servo it into the closed position. Since this is the case, gas pressure will build up in the servo port 296 until sufficient pressure has been built up behind the diaphragm to move the flow oscillator cartridge 288 to a closed position. As soon as this occurs, flow of gas is interrupted through the flow oscillator cartridge 288. As soon as this occurs, the gas which is behind the diaphragm in the oscillator timing reset cartridge 302 is bled down to permit it to move to its normally open position. This bleed down occurs through the oscillatory amplitude needle valve assembly 317 and through the venturi jet 322. It also occurs through the frequency band adjustment needle valve assembly 308 and dumps into the reservoir 314. There is then a controlled flow of the gas from behind the diaphragm in the flow oscillator cartridge 288. This flow passes from the servo port 296 through the oscillator expiratory time off needle valve assembly 298 through inlet 301 and the outlet 303 of the oscillator timing reset cartridge 302, since it is now in its normally open position, and through the normally open interval phasing cartridge 306 and into the entrainment reservoir 314. As soon as there has been sufficient dumping of gas from behind the diaphragm of the flow oscillator cartridge 288, the flow oscillator cartridge 288 moves to its normally open position and the gas begins to flow into the servoing port 309 of the oscillator timing reset cartridge 302 to move it to a closed position to complete the sequence.

As hereinbefore pointed out, gas is supplied to the time cycle regulator 272 of the transport service module 262 at the time that the master on/off switch 276 is turned on. The outlet 326 of the regulator 272 is connected to the inlet 327 of a flow cartridge 328 which forms a part of the volumetric diffusion respiration module 264. The flow cartridge 328 is in a normally open position and therefore gas supplied to an inlet 327 normally flows through an outlet 329 and then through a servoing isolation check valve 331 to the servo port 332 of the interval phasing cartridge 306 to servo it into the closed position. The interval phasing cartridge 306 can provide a variable delay. For example, a delay from one to six seconds can be provided as determined by the position of the adjustable oscillatory delay needle valve assembly 333 which is in communication with the entrainment reservoir 314.

At the time that gas is supplied to the flow cartridge 328, when in its normally open position, gas is also supplied to a servo port 334 of the timing reset cartridge 336 to move it to a closed position from its normally open position. At the same time, gas is also supplied from the outlet 329 through an inspiratory isolation check valve 337 to the inlet 338 of an inspiratory time needle valve assembly 339. The outlet 341 of the needle valve assembly 339 is connected to the servo port 342 of the flow cartridge 328 to servo it to a closed position after sufficient gas has flowed through the needle valve assembly 339.

As soon as gas is no longer supplied to the servo port 309, the gas is bled down through the servo isolation check valve 331 through the oscillatory delay needle valve assembly 333 to the entrainment reservoir 314. This permits the timing reset cartridge 336 to move to its normally open position. Also as soon as flow is interrupted through the flow cartridge 328, gas behind the servoing diaphragm of the cartridge 328 is bled out of the servo port 342 through the inlet 343 of an expiratory time needle valve assembly 344 which is carried by the timing reset cartridge 336. Gas flows through the outlet 346 of the needle valve assembly 344 to the inlet 347 of the timing reset cartridge 336 which is now in its open position and gas flows through the outlet 348 which is connected into the entrainment reservoir 314. As soon as sufficient bleed down of gases from behind the diaphragm of the flow cartridge 328 has occurred the flow cartridge 328 will move to its normally open position to again permit gas from the time cycle regulator 272 to flow out of the outlet port 329 to start the cycle anew.

In order to prevent the timing reset cartridge 336 from locking up and also to provide range compensation, an orifice 351 is provided which is connected to the servo port 334 and is also connected to the entrainment reservoir 314. This orifice 351 can be of a suitable size such as 0.013 inch. Gas from the servo port 334 also can flow through a flow pressure needle valve assembly 352 and then through a ventilator output low pressure check valve assembly 353 into the venturi jet 322.

Means is provided for providing manually controlled inspiration and includes a manually operated inspiration valve 356 having a manually operable push button 357 Regulated gas is supplied from the outlet 326 of the time cycled regulator 272 and is supplied to the inlet 358 of the manual inspiration valve 356. The outlet 359 of the manual inspiration valve 356 is connected into the pneumatic circuitry so that gas supplied through the manual inspiration valve 356 is supplied through the flow pressure needle valve assembly 352 and to the ventilator output low pressure check valve assembly 353 directly into the venturi jet 322.

A demand CPAP (constant positive airway pressure) cartridge 361 is provided as part of the alarm/control module 263. The cartridge 361 is provided with a control knob 362 which is provided for adjusting the pressure that is supplied to the diaphragm as hereinbefore described in conjunction with the demand CPAP cartridge 49 in the previous embodiment.

The demand CPAP cartridge 361 is provided with regulated gas from the time cycle regulator 272 which is supplied to the input 363 of the cartridge 361. When the cartridge 361 is in an open position, gas is supplied through an outlet 364 through a low pressure check valve assembly 366 and to the venturi jet 322. Means is provided for connecting the demand CPAP cartridge to the patient airway, and consists of a sensing port 367 which is connected to an outlet 368. An inlet 369 is connected to the outlet 368 and is in communication with the patient airway through an inlet 371 provided in the venturi assembly 323. Thus it can be seen that in the event the patient requires breathing gases to be supplied the patient will cause reduced pressure to be provided behind the diaphragm of the CPAP cartridge 361 to cause it to move to an open position and to permit breathing gases to be supplied directly to the venturi jet 322. Means is provided for dampening movement of the diaphragm of the demand CPAP cartridge 361 and consists of a dampening orifice 372 which is connected between the outlet 364 and the sensing port 367. This prevents undesirable oscillation in the demand CPAP cartridge.

The alarm/control module 263 also includes a fail-safe servo cartridge 376 which is provided with a control knob 377 for adjusting the pressure under which the fail-safe servo will move from its normally closed position to an open position. Gas is supplied from the venturi socket 319 to the inlet 378 by means of a pressure calibration needle valve assembly 379 having an outlet which is connected to the servo port 381 of the fail-safe servo cartridge 376. At the same time, gas is supplied from an outlet 382 of the needle valve assembly 379 and is in communication with an anti-surge pressure balance reservoir 383 through an alarm reset check valve assembly 384 to the inlet 378. The reservoir 383 is also connected to an alarm reset check valve assembly 384 which is connected to the fitting 319 connected to the venturi jet 322. The venturi jet 322 is also connected to the inlet 378 of the fail-safe servo cartridge 376. The fail-safe servo cartridge 376 is provided with an outlet 386 which is connected to the inlet 387 of a fail-safe cartridge 388. The outlet 386 is also connected to a fail-safe bleed orifice 389 of a suitable size such as 0.013 inches which is connected to the entrainment reservoir 314.

When gas is supplied through the inlet 387 of the fail-safe cartridge 388, the fail-safe cartridge is servoed from its normally closed position to an open position. As soon as this occurs, gas is supplied from the venturi jet 322 through an inlet 391 through an outlet 392. Gas passing through the outlet 392 passes through an alarm orifice 393 of a suitable size such as 0.024 inches which gives an audible alarm. In addition, gas is supplied to an alarm pressure relief governor 396 which dumps gas to the atmosphere and will also give an audible alarm. Also pressure is supplied to a fail-safe indicator 397 to indicate that the fail-safe circuitry has been called into action. In this way it can be seen that the gas which would normally be delivered to the patient is released into the atmosphere to drop the pressure substantially while at the same time giving alarms without locking out the ventilator. Manually operated reset means for resetting the fail-safe servo cartridge 76 is provided and consists of a manually operated switch 398 having its input 399 connected to an output 400 of the needle valve assembly 379.

The breathing circuit 266 is substantially identical to the breathing circuit 16 disclosed in the embodiment shown in FIG. 1 and for that reason will not be described in detail. The alarm/control module 263 has means for supplying gas to the nebulizer 58 of the breathing circuit 266 which includes a nebulizer control needle valve assembly 401 which has its inlet 402 connected to the outlet 24 of the blender 21 and has its outlet 403 connected to an outlet socket 404. An inlet 406 is connected to the outlet 406 which is connected to the nebulizer 58.

Means is provided for presenting a numerical readout to the clinician and consists of a cartridge 413 which has an inlet 414 connected to an outlet 415 of the oscillatory amplitude needle valve 317. The cartridge 413 carries a paddle 416 carried by a spring loaded shaft 17. The shaft is driven by a diaphragm 418. Thus it can be seen that when the diaphragm 418 is loaded when gas is supplied through the inlet port 414, the paddle 416 is moved outwardly against the force of a spring 419 carried by the shaft 417. As soon as the pressure behind the diaphragm 418 is relieved, the paddle 416 will be returned under the force of the spring 419.

The paddle 416 is used for breaking a beam from a source of energy to initiate a signal which can be utilized to provide a numerical presentation for each movement of the paddle. By way of example, a source of infrared energy can be positioned on one side of the paddle and means for sensing infrared energy can be positioned on the other side of the paddle. The paddle 416 is positioned in such a manner so that with each pressurization of the cartridge 413 the paddle 416 will only interrupt the beam of energy at the end of travel to prevent a double interruption during each oscillatory cycle of the ventilator.

Operation of the embodiment of the invention shown in FIG. 3 may now be briefly described as follows. Let it be assumed that it is desired to ventilate a patient and that the breathing circuit 266 has been connected to the patient. The blender 21 is adjusted to supply an appropriate mixture of gases such as a mixture of 60 percent oxygen and 40 percent air. Let it be assumed that the master on/off switch 76 has been turned on to supply gas to both of the regulators 271 and 272. With the master on/off switch 276 in an off position, source gas is directed through the manual on/off switch 276 through the inlet port 274 and through the outlet port 279 into the auto load isolation check valve 280 to deliver gas into the servo port 342 of the cartridge 328 and into the servo port 334 of the cartridge 336 to hold the ventilator in an expiratory phase. With the expiratory time metering valve 344 in the full clockwise off position leakage from the timing circuit is zero. Now let it be assumed that the master on/off switch 276 has been turned to the "on" position to supply gas to both of the regulators 271 and 272. Gas is supplied from the regulator 271 to the flow oscillator cartridge 288. Gas flow through the flow oscillator cartridge 288 initiates closing of the oscillator timing reset cartridge 302. Gas from the flow oscillator cartridge 288 also is supplied to the oscillatory amplitude needle valve assembly 317 which is utilized to control the pressure at the physiological airway of the patient and supplies the gas to the venturi jet 322 and also to the exhalation valve assembly 228 to close the same. This commences the pulsation of gas which will hereinafter be described. The duration of the pulse of gas is determined by the length of time required to servo the flow oscillator cartridge 288 closed. Gas flows through the oscillator inspiratory isolation check valve assembly 291 through the oscillator inspiratory time on needle valve assembly 293 to the servo port 296 of the flow oscillator cartridge 288. Concomitantly, gas is supplied to the oscillator inspiratory time off needle valve assembly 298 where it comes into contact with the now closed oscillator timing reset cartridge 302. Gas thus builds up under pressure in the flow oscillator cartridge 288 to servo the same to a closed position within a period of time determined by the adjustment of the needle valve assembly 293. As soon as the flow oscillator cartridge 288 is moved to a closed position, the flow of gas to the venturi 322 and to the exhalation valve assembly 228 is interrupted, permitting the exhalation valve assembly 228 to open to permit the pressure in the physiological airway to drop towards atmospheric pressure.

The length of time which is taken for dropping to or above atmospheric pressure is determined by the adjustment of the oscillator inspiratory time off needle valve assembly 298. The routing of bleed off gases is from behind the diaphragm of the flow oscillator cartridge 288 through this oscillator expiratory time off needle valve assembly 298 to the oscillator timing reset cartridge 302 which is now in an open position through the interval phasing cartridge 306 to the entrainment reservoir 314. As soon as the pressure has been reduced sufficiently, the flow oscillator cartridge 288 will move to its normally open position which then permits the gas to flow to the patient. The oscillator timing reset cartridge 302 is again moved to a closed position and the cycle is repeated.

Thus as shown in FIG. 4, there is provided a plurality of generally triangular shaped oscillations 416. The time interval which is utilized for the diffusive portion of the ventilatory cycle is determined by the timing provided by the flow cartridge 328 provided in combination with the timing reset cartridge 336. Gas is delivered through the flow cartridge 328 and then through the flow pressure needle valve assembly 352 through the ventilator output low pressure check valve assembly 353 to the venturi jet 322. At the same time, gas is also supplied through the servoing isolation check valve 331 to the servo port 332 of the interval phasing cartridge 306 to move it to a closed position. As soon as this occurs, the source of oscillatory pulses to the patient's airway is interrupted. As gas is supplied to the flow cartridge 328, gas is also supplied through the inspiratory isolation check valve assembly 337 to the inspiratory time needle valve assembly 339 to supply gas to the servo port 342. Gas at the same time is supplied to the inspiratory time needle valve assembly 344 and to the timing reset cartridge 336 which is in a closed position.

Therefore, gas builds up in the flow cartridge 328 to servo it to a closed position after a predetermined length of time determined by the positioning of the inspiratory time needle valve assembly 339. Because a longer period of time is desired, the inspiratory needle time needle valve assembly is provided with a finer adjustment and with a corresponding oscillator inspiratory time on needle valve assembly 293. As soon as the flow cartridge 328 has been moved to a closed position, the flow of gases in the interval phasing cartridge 306 is interrupted and the gas behind the servo diaphragm is bled down through the oscillatory delay needle valve assembly 333 to the entrainment reservoir 314. The delay provided by the needle valve assembly 333 determines the post volumetric delivery pause. The period of time which is taken for delivering the tidal volume to the patient is shown by the curve 417 in FIG. 4. As soon as the flow of gases is interrupted by the flow cartridge 328, the exhalation valve assembly 228 is allowed to open permitting the patient to exhale. The length of time during which the patient exhales is determined by the adjustment of the expiratory time needle valve assembly 344.

As soon as the flow of gases through the flow cartridge 328 is interrupted, the gas which is holding the timing reset cartridge 336 closed is bled out and passes through the flow pressure needle valve assembly 352 through the ventilator output low pressure check valve assembly 353 and into the venturi jet 322. Bleed down continues until the timing reset cartridge 336 moves to its normally open position which is represented by the curve 423 in FIG. 4. At the same time, gas is also bled out from behind the diaphragm in the flow cartridge 328 through the expiratory time needle valve assembly 344 through the timing reset cartridge 336 to the entrainment reservoir 314.

In the event that the flow pressure needle valve assembly 352 is in a fully closed position, oscillation will still be brought about because the gases under pressure behind the diaphragm of the timing reset cartridge 336 can bleed down through the range compensator orifice 351 into the entrainment reservoir 314. This ensures that the volumetric timing circuit cannot be locked up accidentally.

In the embodiment of the invention shown in FIG. 3, even when manual inspiration is provided by use of the manual inspiration valve 356, the gas under pressure supplied to the patient is controlled by the flow pressure needle valve assembly 352.

As soon as the flow cartridge 328 moves to an open position, the cycle hereinbefore described will be repeated in which the diffusive oscillation will first take place followed by the volumetric exchange. As shown in FIG. 4 it is possible to provide a pause after the volumetric exchange which can be utilized to introduce CPAP if desired. CPAP can be provided by turning the CPAP control knob 362 to the "on" position and to provide a desired level of CPAP by adjusting the pressure on the diaphragm. The CPAP cartridge provides a floor or base line against which the patient must exhale. If desired, a pause can be provided without CPAP followed by diffusive oscillation.

It should be appreciated that if desired, the interval phasing cartridge 306 can be omitted, in which event, the oscillatory pattern provided by the flow oscillator cartridge and the oscillator timing reset cartridge 288 and 302 respectively, would provide an oscillatory pattern superimposed on the volumetric exchange pattern provided in FIG. 4.

In utilization of the embodiment of the invention shown in FIG. 3 it is also possible to provide oscillatory demand CPAP. This can be accomplished by establishing the desired constant positive airway pressure by appropriate adjustment of the knob 362 ranging typically from five to ten centimeters of water and thereafter closing the expiratory time valve assembly 344. This will establish a diffusive oscillatory pattern on top of the CPAP. The frequency of pulsation is controllable by adjustment of the oscillator inspiratory time on needle valve assembly 293 and adjustment of the oscillator expiratory time off needle valve assembly 298 with the amplitude of the pulses being controlled by the adjustment of the oscillatory amplitude needle valve assembly 317. The advantage of such a procedure is that it effectively closes the right to left pulmonary shunt providing an oscillatory blood gas interface on top of the CPAP.

The frequency band adjustment needle valve assembly 308 is utilized for adjusting the frequency band. This is accomplished by controlling the rate of bleeding from the expiratory circuit for the flow oscillator and oscillator timing reset cartridges 288 and 302. By increasing the rate of bleedoff, a higher frequency can be obtained. Conversely, by decreasing the rate of bleedoff of gases from the expiratory circuit, a lower frequency can be obtained.

It should be appreciated that each time a pulse is produced by the ventilator shown in FIG. 3 the failsafe circuitry is reset. This is accomplished because each time gas is accumulated in the reservoir 383 it is bled off through the alarm reset check valve 384 into the breathing circuit 266. It is only when there is an accumulated mean pressure which is greater than that determined by the adjustment of the knob 377 on the fail-safe servo cartridge 376 that an alarm is initiated. The fail-safe servo cartridge 376 activates the fail-safe cartridge 388. As soon as the fail-safe cartridge 388 opens, gas is bled directly from the venturi jet 322 through the alarm pressure relief governor 396 to the atmosphere. At the same time, the fail-safe indicator alarm 397 is actuated, as hereinbefore explained, a parallel alarm is also actuated by activation of the alarm 394 through the alarm orifice 393. The alarm orifice 393 prevents overwhelming of the reeds in the audible alarm 394. The governor 396 provides a backup alarm to the sound which is created by the alarm 394 during the time that the gas is being released into the atmosphere. The amount of noise created by the governor 396 is determined by the rate of flow of gas through the same.

The manner in which the timing circuit for the ventilator in FIG. 3 is loaded by the use of the master on/off switch and the check valve 280 prevents a potentially large initial tidal volume delivery to the patient when the master on/off switch 276 is turned to the "on" position and when the inspiratory time selection is near maximum. The circuit utilized in the present invention virtually eliminates any possibility of malfunction of the automatic phasing as, for example, could occur on and off through the master on/off switch 276 without sufficient time for the auto load system to reset.

An improved breathing circuit 429 is shown in FIG. 5 which can be utilized with the embodiments of the invention shown in FIGS. 1 and 3. As shown in FIG. 5, the breathing circuit includes a breathing head assembly 431 which has mounted thereon a nebulizer assembly 432. The breathing head assembly 431 consists of a patient adapter 433 which can be of any suitable type such as a mouthpiece, a mask, or endotracheal tube, which is connected to the lungs of the patient which are represented by the balloon 434. The breathing head assembly 431 also consists of a shrouded venturi assembly 436. A venturi manifold assembly 437 also forms a part of the breathing head assembly 431 and is mounted upon the shrouded venturi assembly 436. An exhalation valve assembly 438 is also mounted upon the shrouded venturi assembly 436.

The shrouded venturi assembly 436 consists of an outer cylindrical member 441 and an inner cylindrical member 442 as well as cylindrical extensions 443 and 444 extending diametrically of the member 441. Suitable means is provided for supporting the inner cylindrical member 442 within the outer cylindrical member 441 while at the same time retaining freedom of flow of gases between the cylindrical members 441 and 442 and through the cylindrical extensions 443 and 444. Thus there can be provided an annular flange 446 formed integral with one of the cylindrical members 441 and 442 as for example on the inner cylindrical member 442 which frictionally engages the other cylindrical member. The inner cylindrical member 442 is provided with a venturi-like passageway 447.

The venturi manifold assembly 437 consists of a cylindrical member 448 which is carried by the inner cylindrical member 442. It carries a venturi jet 449 which is positioned in such a manner so that a jet of gas passing therefrom is axially aligned with the venturi-like passageway 447 provided in the inner cylindrical member 442. Gas is supplied to the venturi jet through a line 451 which is connected to a fitting 452. The line 451 is also connected to the inlet 453 of the exhalation valve assembly 431 so that during the time that gas is being supplied to the venturi jet 449, gas is supplied to a diaphragm 454 of the exhalation valve assembly 438 to hold the exhalation valve 456 in a closed position.

The venturi manifold assembly 437 has diametrically opposed cylindrical extensions 458 and 459 formed thereon. The cylindrical extension 458 has an expiratory gate valve 461 mounted therein through which gases can escape to the atmosphere. The cylindrical extension 459 is connected by a large tube 462 to an inlet fitting 463 formed on the cap 464 of a nebulizer 466. The cap is provided with another fitting 467 which is connected by a large tube 468 to the exhalation valve assembly 431. A tube 468 is also connected to an inlet 469 which has an entrainment reservoir 471 mounted thereon. The inlet 469 is provided with an ambient entrainment gate 472 to permit entrainment of ambient air when required. The entrainment reservoir 471 is provided with a flexible overfill gate 473.

The shrouded venturi assembly 436 is provided with a fitting 476 which is connected by a line 477 to an inlet fitting 478 to make it possible to monitor the patient airway pressure. The fitting 469 is provided with an adapter 479 which is connected by a line 481 to a fitting 482 so that auxiliary gas can be bled into the reservoir 471. The nebulizer cap 464 is provided with an inlet fitting 483 which is connected by a line 484 to a fitting 486 to permit gas to be supplied to operate the nebulizer 466 in a manner well known to those skilled in the art.

The nebulizer assembly 432 consists of a generally cylindrical body 491 which is mounted by a slip fit onto the cylindrical extension 444 provided on the shrouded venturi assembly 436. A bottom reservoir cup 492 is adapted to be mounted by a slip fit onto the bottom end of the body 491 and is adapted to contain a suitable medication such as ten millimeters of a solution that could be utilized in connection with the nebulizer. The body 491 is provided with means for preventing the medication solution from spilling from the nebulizer once the reservoir cup 492 has been placed on the body. This consists of a baffle 493 which is formed of a hollow cylindrical member 494 disposed concentrically within the body 491 and having a diameter substantially less than the inner diameter of the body 491. The cylindrical member 494 is carried by a circular disc-shaped member 496 formed integral with the body 491 and integral with the upper extremity of the cylindrical member 494. A member 497 is mounted in the cylindrical body 491 and above the disc-shaped member 496. It is provided with a venturi-like flow passage 498 and is also provided with a nozzle or jet 499 in axial alignment with the passage 498. The jet 499 is connected to a line 501 which is adapted to be connected to the nebulizer fitting 486. The jet or nozzle 499 is disposed in such a manner so that gases jetting therefrom will pass through the venturi-like flow passage and will impinge upon a ball 502 mounted on the interior surface of the body 491. The venturi-like flow passage is also in communication with a capillary tube 503 which extends downwardly through the hollow cylindrical member 494 a sufficient distance so that it extends into the liquid 504 provided within the reservoir cup 492.

Means is provided for manually cycling the nebulizer 432 and consists of a cylindrical member 506 which is mounted exterior of the body 491. A valve member 507 is mounted within the cylindrical member and is adapted to be moved into and out of engagement with a valve seat 508. Operating button 509 is provided for moving the valve member 507 to an open position against the force of a spring 511. Gas from a suitable source of pressure is supplied to a line 512 connected to the cylindrical member 506. The interior of the cylindrical member 506 is connected by a passage 513 into the interior of the body 491.

Operation of the breathing circuit 429 shown in FIG. 5 can now be briefly described as follows. Let it be assumed that it is desired to use the same in an intensive care situation in which the shrouded venturi assembly would be connected by an endotracheal tube to the patient. Let it be assumed that the exhalation valve 456 has just opened. When this occurs, the exhaled gas passes through the large tube 468 into the entrainment reservoir and into the nebulizer 456 and then to the tube 462 and into the venturi manifold assembly 437. The exhaled gas is released to the atmosphere through the gate valve 461 provided in the venturi manifold assembly. In addition, surplus gas is also discharged to the atmosphere through the overfill gate 473 provided as a part of the entrainment reservoir 471. It should be pointed out that normally there is a slight delay in the opening of the exhalation valve and that prior to this time, the venturi jet will be depressurized and the initial exhalation gases will pass through the expiratory gate valve 461. Within a short period of time thereafter, the exhalation valve 456 opens to provide a parallel path for the escape of exhalation gases from the airway of the patient. The exhalation circuitry cannot become pressurized because the flap 473 on the bottom of the entrainment reservoir opens as hereinbefore explained.

The amount of rebreathing of gases can be readily controlled by the flow of additional gases through the nebulizer and into the reservoir. These fresh gases entering the breathing circuit serve to reduce the $CO_2$ content of the rebreathed gases thereby making it possible to precisely control the $CO_2$ content of the rebreathed gases and to keep the same to an acceptable level so as to prevent hyperventilation. The large nebulizer 466 can be utilized to provide the desired humidification for the gases supplied to the patient. The small nebulizer 432 can be utilized for supplying certain desired drugs to the humidified gases being supplied to the patient. The drugs are introduced in liquid form into the reservoir cup 492. When gas is supplied to the jet 492, it will pass through the like passage 498 to cause the liquid drug 504 to brought up from the reservoir cup 492 to the venturi passage and will cause the drug droplets to impinge upon the ball 502 and cause the same to be broken up into a fine mist. This fine mist of particles is carried upwardly into the shrouded venturi assembly 436 by gases which are introduced into the body 491 by operating the pushbutton 509 to move the valve member 507 to an open position to permit gases to be supplied from the line 12 into the cylindrical area provided between the outer cylindrical member 441 and the inner cylindrical member 42 and to cause the same to be moved into the airway of the patient. Many large particles carried into the shrouded venturi assembly may impinge upon the inner cylindrical member 442 and eventually fall off and rain into the body 491 of the venturi assembly 432. The droplets will collect onto the disc-shaped member 496 and will pass downwardly into the cup reservoir in the cylindrical space provided between the inner surface of the cylindrical member 494 and the outer surface of the capillary tube 503.

In addition to the use of the nebulizer 432 shown in FIG. 5, typically, the patient adapter would be in the form of a mouthpiece. Also in such an arrangement, the tube 468 could be omitted so that the exhalation valve will empty directly to the atmosphere. In addition, the tube 462 can be removed and the cylindrical extension 459 can be plugged. The nebulizer 432 is designed as a hand-held unit and in such a manner so that the drug contained in the reservoir cup is non-spillable. It is non-spillable because in the event the hand-held unit is tipped on its side, there is sufficient volume within the interior of the body 491 to accommodate the liquid drug 504 within the reservoir cup 492 so that it will not rise to a level at which the liquid could pass through the interior of the cylindrical member 494. The disc-shaped member 496 prevents the escape of the liquid from the reservoir cup 492. Thus the nebulizer 432 can be readily used as a hand-held unit without any danger of spilling the drug contained therein.

During the time that gases are being delivered from the shrouded circumferential area into the airway of the patient, gases are also being supplied through the venturi passage 447 driven by the gases from the jet 449 also into the airway of the patient in a direction parallel to the path of the flow of gases through the circumferential shrouded area of the venturi assembly to thereby create an effective mixing of the gases delivered to the airway of the patient.

In summary, it can be seen that the jet 499 in combination with the capillary 503 produces a spray of large particles which extends across the body 491 where they impinge upon the hemisphere or ball 502 to form a fractured aerosol. This fractured aerosol is delivered into the circular plenum area of the encapsulated or shrouded venturi assembly 436 to cause a whirling mixing action to occur. The aerosol is then supplied to the patient airway and at the same time is mixed with gases delivered through the venturi-like passageway 447. In this way concentric flows of gases are delivered to the airway of the patient.

When the breathing circuit shown in FIG. 5 is used in conjunction with the embodiment of the invention shown in FIG. 3 pulsatile stroke volumes are precisely delivered onto the hemisphere to provide a pulsatile volume of vehicular gas for the transport of an aerosol upward into the shrouded area. The rate of oscillatory stroke volume increases with higher oscillatory frequencies and the rate of aerosol transport is concomitantly upgraded. A pulse of discharged gas from the oscillator timing circuit occurs prior to the actual stroke volume delivery causing a bolus of aerosol to reach the distal venturi at almost the precise time the oscillatory volume of therapeutic gas is injected. The dual pathways provided for the gases supplied to the airway of the patient play a major role in maximizing oscillatory stroke volume and minimizing mechanical dead space. At the moment of expiratory phasing between oscillations or a pause, gas flow through the venturi reverses to ambient through the flapper valve 461 which is followed by opening of the exhalation valve 456. This provides for a larger proximal airway pressure differential during successive oscillations, thereby making possible a larger stroke volume delivery into the pulmonary structures enhancing mechanical mixing of the gases.

In the breathing circuit shown in FIG. 5, a controlled partial rebreathing circuit is provided by the use of the large tube 468 which connects the exhalation valve assembly 431 to the manifold 469 connected to the distensible bag 471. The distensible bag, or reservoir 471 which is provided with the overfill gate 473 provides a low pressure ambient valve and accommodates ambient venting when large physiological volumes are rapidly expelled into the breathing circuit. During inspiration, gas may be entrained from the distensible reservoir 471 or from ambient through the ambient inlet valve 472 should the gas supply in the reservoir 471 be depleted. Expiratory stroke volumes are delivered preferentially through the exhalation valve port 443 through the large tube 468 into the distensible reservoir 471 to ambient through the cap 464 of the large nebulizer 466 and through the tube 462 through the exhalation gate 461 provided on the venturi manifold assembly 437.

With the breathing circuit 429 shown in FIG. 5 pulsatile pressures can be regulated to provide substantially constant values within the breathing circuit while at the same time accommodating many ventilatory techniques. Carbon dioxide concentrations in the circuit can be maintained at optimal levels minimizing hyperventilatory tendencies. By controlling the washout (decrease) of carbon dioxide by controlling the amount of new gases supplied into the breathing circuit, the carbon dioxide level can be precisely controlled and metered gases can be delivered on a constant flow basis into the breathing circuit.

In FIG. 6 there is disclosed an embodiment of a ventilator incorporating the present invention which can be characterized as an intermittent percussive ventilator. A source of gas is provided of a conventional type such as an appropriate mixture of air and oxygen from a blender 21 of the type hereinbefore described in the previous embodiments. This air/oxygen source is supplied through a filter 521 to the inlet 522 of a rotary pneumatic on/off switch 523. The rotary on/off switch 523 is provided with a control knob 524 for operating the same and first and second outlets 526 and 527. When the knob 524 is turned to the "on" position, gas is supplied through the outlet 526 to the inlet 528 of a manually operated normally closed valve 529 which is provided with a pushbutton 531. At the same time, gas is supplied from the outlet 526 to the inlet 532 of a normally open flow oscillator cartridge 533. Gas is supplied from the outlet 534 of the cartridge 533 to the inlet 536 of a normally open timing oscillator reset cartridge 537. Gas is also supplied from the outlet 534 through an oscillator inspiratory isolation check valve 538 to an inlet 539 of an oscillator inspiratory time on the needle valve assembly 541. Gas flows through the valve assembly 541 at a controlled rate through the outlet 542 to the inlet 543 an expiratory time off needle valve assembly 544. Gas is also supplied to the servo port 546 of the flow oscillator cartridge 533. Gas is also supplied from the outlet 534 to the inlet 547 of an oscillatory amplitude needle valve assembly 548. Gas is supplied at a controlled rate through the outlet 549. The outlet 549 is connected to an outlet fitting 551. The outlet fitting 551 has mounted therein an inlet fitting 552. The inlet fitting 552 is connected to the venturi jet 553 of a venturi manifold assembly 554 that forms a part of the breathing circuit 556 of the type generally described in conjunction with FIG. 5. As disclosed therein, the breathing circuit 556 also includes a shrouded venturi assembly 557. The venturi assembly 557 has a venturi like passageway 558 through which the jet of gases from the venturi jet 553 passes. The shrouded venturi assembly 557 is adapted to be connected by a patient adapter 559 to the patient airway 561. The breathing circuit 556 also includes an exhalation valve assembly 562 of the type hereinbefore described. At the same time gas is also supplied to the exhalation valve assembly to move the same to a closed position.

Operation of the flow oscillator cartridge 533 is regulated by the oscillator timing circuit as hereinafter described. Gas flowing from the normally open flow oscillator cartridge 533 servoes the diaphragm of the timing oscillator reset cartridge 537 to move it to a closed position. At the same time, gas is being supplied to the servo port 536 of the flow oscillator cartridge 533 to the oscillator inspiratory time on needle valve assembly 541 at a controlled rate as determined by adjustment of the oscillator inspiratory time on needle valve assembly 541. As soon as the flow oscillator cartridge 533 is servoed to a closed position, the flow of gas to the flow oscillator cartridge 533 is terminated. This interrupts the flow of gas to the venturi jet 553 and into the airway of the patient. The termination of flow through the flow oscillator cartridge 533 permits the timing oscillator reset cartridge 537 to return to its normally open position. As soon as this occurs, gas behind the diaphragm of the flow oscillator cartridge 533 is bled off through the oscillator inspiratory time off needle valve assembly 544 through an outlet 563 to an inlet 564 of the timing oscillator reset cartridge 537 and through an outlet 566 since the cartridge 537 is now in its normally open position to an inlet 567 of a normally open interval phasing cartridge 568. Gas passes through the outlet 469 to an outlet fitting 571. An inlet fitting 572 is mounted in the outlet fitting 571 and is connected to the inlet 573 of a manually operated remote cycling valve 574. The valve 574 is provided with a pushbutton 576 for manual operation of the same. The valve 574 is provided with an outlet 577 which is open to ambient when the pushbutton 576 is depressed. The valve 574 is also connected to a large tube 578 which is connected to the venturi manifold assembly 554. Thus it can be seen that when the flow oscillator cartridge 533 is closed and interrupts the flow of gas to the venturi jet 553, the exhalation valve 562 is permitted to open and gas from behind the diaphragm of the flow oscillator 533 is emptied to atmosphere through the venturi manifold assembly 554 through the expiratory gate 579 or alternatively through the exhalation valve assembly 562. As soon as sufficient gases have been bled out from behind the diaphragm of the flow oscillator 533, the flow oscillator 533 moves to its normally open position to permit the flow of gas through the flow oscillator 533 in the manner hereinbefore described to again cause gases to flow through the venturi jet 553 and to cause closing of the exhalation valve assembly 562.

The rate of oscillation (opening and closing) of the oscillator flow cartridge 533 is determined by adjustment of the oscillator inspiratory time on and the oscillator expiratory needle valve assemblies 541 and 544. Inspiratory/expiratory ratios of various proportions in either direction can be established to provide the desired type of diffusive or volumetric exchange in the delivery of gas to the patient airway. The amplitude of oscillatory gases delivered to the patient airway is controlled by metering gas at the desired rate through the oscillatory amplitude needle valve assembly 548. Oscillatory rates of over 25 Hertz can be programmed with stroke volumes decreasing with rate. Reciprocally, volumetric oscillation rates of one oscillation per minute or less can be set up with unlimited optional stroke volumes. During diffusive ventilatory protocols at rates of over 100 cycles per minute, mechanical mixing and diffusion serve to homogenize intrapulmonary gases to more effectively 20 control partial pressures of oxygen and $CO_2$ in the arterial blood.

The proximal airway pressure rise for each oscillation is under the control of the oscillatory amplitude metering valve 548 that determines the rate of flow to the downstream venturi jet 553. The peak pressure which will be encountered by the physiological structures, i.e. the patient airway, is determined by the gross resistance to flow downstream of the shrouded venturi assembly 557, the pressure drop across the venturi jet 553 and the resistance to entrainment of air by the shrouded venturi assembly 557. The pressure will rise until a full stall (pneumatic clutching) occurs within the ungated venturi assembly 557. Therefore, the peak successive oscillation pressure buildup is controlled by pneumatic clutching with the ungated shrouded venturi assembly 557 being referenced to ambient.

With this embodiment of the ventilator, an oscillatory demand CPAP can be established for a patient at a selected frequency between 3 to 15 centimeters of $H_2O$. This can be readily accomplished by establishing the ratio between the inspiratory and expiratory times. By decreasing the expiratory time, the CPAP is increased and conversely by decreasing the expiratory time the CPAP is decreased so that in effect there is provided an oscillatory pattern of pulses at a selected CPAP which is provided by the pneumatic clutching of the shrouded venturi assembly 557. In this way, the patient must exhale against the established oscillatory pressure. When the patient wishes to breathe on demand, the patient can inhale gases in the manner hereinbefore described. In this manner, the patient receives a controlled mean intrathoracic pressure rise increasing the patient's functional residual capacity. The frequency of oscillation and the amplitude of oscillatory stroke volume provides the desired mechanical mixing and diffusion of gases within the patient's lungs.

At the time that gas is supplied from the outlet 534 to the inlet 536 the diaphragm of the timing oscillator reset cartridge 537 is moved to a closed position to again permit servoing of the diaphragm of the flow oscillator cartridge 533 to a closed position.

Mechanical means of frequency band control beyond mechanical metering of the flow oscillator cartridge 533 can be accomplished by connecting a metering orifice of a suitable size such as 0.024 inches between the point F in FIG. 6 connected to the outlet 536 of the timing reset cartridge 537 and the point G connected to the outlet 581 of the oscillatory amplitude needle valve assembly 548 and also connected to an outlet fitting 582. The outlet fitting 582 has mounted therein an inlet fitting 583 which is connected to a venturi jet 584 of a nebulizer 586. The nebulizer 586 can be of the type described in U.S. Pat. No. 3,172,406. The nebulizer 586 is connected by a tube 587 into the tube 578 connected to the venturi manifold assembly 554. An entrainment gate 584 is mounted on the nebulizer 586 to permit ambient air to be entrained into the nebulizer when necessary. By providing the orifice between points F and G, it can be seen that gas is purged from behind the diaphragm of the timing oscillator reset cartridge 537 which as shown is through the nebulizer 586 and then to ambient. If desired the connections can be omitted and the orifice can bleed directly to ambient. This bleed down of the space behind the diaphragm of the timing oscillator reset cartridge 537 is occurring during the time that the diaphragm of the flow oscillator cartridge 533 is being unloaded for movement towards a closed position. An increased rate of diaphragm unloading of the timing oscillator reset cartridge 537 increases the opening rate of the reset cartridge providing for a more rapid cycling or oscillation. Oscillatory rates approaching 30 Hertz can be obtained with a large orifice.

Interval phasing (oscillation on/off) is accomplished by manual means. A remote cycling valve 574 is operated by the patient. The valve 574 is in its normally closed position and timing gases cannot be purged from the outlet 566 of the timing oscillator reset cartridge 537 and therefore timing gases are effectively locked up in the flow oscillator cartridge 533 of the timing circuit. This causes the oscillator flow cartridge 533 to remain closed (non oscillating).

When the patient pushes in the pushbutton 576 of the manual cycling valve 574, gases are purged to ambient from the oscillator flow cartridge 533 through the interval phasing cartridge 568 starting oscillation of the flow oscillator 533 and delivery of gases to the venturi jet 553 and to the nebulizer 586. When the lungs are sufficiently ventilated with repetitive oscillatory aerosolized stroke volumes and associated pressure rise, the patient releases the manual pushbutton 576 and exhales to the ambient through the exhalation valve assembly 562. A gradual decrease in oscillatory rate and amplitude occurs when the pushbutton 576 is released which causes a gradual reversal of mass air flow from the patient pulmonary structure minimizing tendencies for diffuse physiological airway collapse. This delay can be varied by controlling the rate of bleed down through the needle valve assembly 544 and through the interval phasing cartridge 568.

As hereinbefore described, the outlet 526 of the manual on/off switch 524 is connected to the manual inspiration valve 529. The manual inspiration valve 529 is provided with the pushbutton 531 which makes it possible for the clinician to totally override and pace all phasic respiratory functions with the ventilator. Source gas is supplied from the outlet 526 through the outlet 591 which is connected to the outlet fitting 551 and which in turn is connected to the venturi jet 553. Continued holding in of the pushbutton 531 delivers nonmetered flow to the venturi jet 553 to cause flow into the patient airway to occur until the pushbutton 531 is released. The patient can then exhale with the inspiration beginning again when the pushbutton 531 is depressed.

Phasic cycling of the ventilator below 100 cycles per minute can be established by the addition of a reservoir (not shown) capable of containing gas installed between the point D which is connected to the outlet 543 and point E which is connected to the outlet 542. By the addition of this optional reservoir, the volume which must be filled to cause the diaphragm of the flow oscillator 533 to be servoed closed will be lengthened to provide the lower frequency of oscillation desired.

Means is provided for automatic phasing of the ventilator shown in FIG. 6. For this purpose, gas is supplied from the outlet 521 of the master on/off switch 523 through timing isolation check valve to an inlet 597 of a normally open timing cartridge 598. The outlet 599 of the timing cartridge 598 is connected to an inlet 601 of a timing manifold 602. Gas from the timing manifold 602 is distributed through an outlet 603 to a servo port of the interval phasing cartridge 568. Gas is also supplied to the outlet of the servo isolation check valve 606. Gas is supplied from the manifold 602 to the outlet 607 through the servo port 608 on a normally open timing reset cartridge 609. Gas is supplied from the outlet 611 to the master timing isolation check valve 612. Outlet 613 is connected to a fixed reservoir refill orifice 614 or a predetermined size such as 0.024 inches. Gas supplied to the timing isolation check valve assembly 612 passes through the same, and into the inlet 616 of the volumetric exchange (closed exhalation) needle valve assembly 617. Gas at a controlled rate is supplied at the outlet 618 of the needle valve assembly 617 to the inlet 619 of the diffusion interval (open inspiration) needle valve assembly 621 where the gas is again metered and supplied through an outlet 622 to an inlet 623 on the open timing reset cartridge 609. Gas is supplied from an outlet 624 into an outlet fitting at 626 which is adapted to be connected to an entrainment reservoir (not shown) of the type hereinbefore described. Gas from the outlet 618 also flows into a low frequency timing reservoir 627. The entrainment reservoir is connected to the servo port 628 of the timing cartridge 598.

Patient airway pressure is measured by a gauge 631 which is connected through an adjustable gauge orifice 632 to an outlet fitting 633. An inlet fitting 634 is mounted in the fitting 633 and is connected to the shrouded venturi assembly 557 so as to be open to the patient airway pressure.

Operation of the embodiment of the ventilator shown in FIG. 6 which utilizes automatic phasing may now be briefly described as follows. Source gas from the master on/off control, switch 523 passes through the timing cartridge 598 and charges the timing manifold 602. Gas is metered through the volumetric exchange (closed isolation) needle valve assembly 617. Gas entering the timing cartridge cannot exit through the diffusion interval metering valve 621 because the timing reset cartridge has been servoed to a closed position. Therefore the timing circuit is pressurized at a rate controlled by the volumetric exchange (exhalation) metering valve 617 until the pressure acting through the servo inlet 628 of the timing cartridge 598 is sufficient to servo the diaphragm off closing the normally open cartridge 598 and interrupting the flow of gas through the cartridge 598. During the time that there is gas flow through the timing cartridge 598, the interval phasing cartridge 568 is servoed into the closed position. The interval phasing cartridge 568 receives at its inlet 567 a pulsatile flow from the outlet of the timing oscillator reset cartridge 537. When the out flow from the timing oscillator reset cartridge 537 is obstructed by closing of the interval phasing cartridge 568, oscillation ceases because of a locked up oscillator timing circuit.

When the timing cartridge 598 closes, gas flow to the timing manifold 602 ceases. The manifold 602 is depressurized through the reservoir refill orifice 614 causing opening of the interval phasing cartridge 568 and the timing reset cartridge 609 to again initiate diffusion (inspiratory) level. When the timing reset cartridge opens, the diffusion interval (inspiratory) metering valve 621 starts a bleed down through the now open timing reset cartridge 609 of the timing gases behind the manifold of the timing cartridge 598 and in the reservoir 627 until the timing cartridge 598 moves to its normally open position at which time a repetitive cycle commences. From the foregoing it can be seen that the oscillation timing circuit is a slave to the master phasic (interval) timing circuit hereinbefore described.

An overriding function can be initiated by terminating the diffusion interval by loading the timing circuit into the expiratory phase by charging the timing circuit through the servo isolation check valve 606 by connecting it into which an input would be supplied from the inspiratory phase of the ventilator shown in FIG. 3 in which the servo isolation check valve 606 would receive the same pneumatic signal which is received from the isolation check valve 331 shown in FIG. 3. This additional or overriding function can be a volumetric stroke volume or a diffusive oscillation delivered through the same or a parallel venturi jet into the patient airway. This alternative could be used to accommodate partial pressures of oxygen and carbon dioxide in the arterial blood in the maintenance of the respiratory function of the patient.

Manual cycling as an override of automatic programmed cycling can be accomplished by closing the diffusion interval (inspiratory) metering valve 621 and opening the volumetric exchange (expiratory) metering valve 617. This causes constant oscillation by keeping the interval phasing cartridge 568 in a continuously open position. During the time that automatic cycling is being utilized in the ventilator, the fitting 572 should be removed from the fitting 571 so that the fitting 571 exhausts to the atmosphere.

When it is desired to utilize the remote cycling valve 574, the fitting 572 is mounted in the fitting 571. The valve 574 is normally closed and when the pushbutton 576 is depressed, the pulsatile timing gases supplied through the timing oscillator reset cartridge 537 are supplied through the interval phasing cartridge 568 and are released to ambient through the valve 574 to cause the onset of oscillation as programmed. Release of the button 576 stops the oscillation.

From the foregoing, it can be seen that with the ventilator disclosed in FIG. 6, three different types of diffusive ventilation of the patient airway can be accomplished at rates of over 100 cycles per minute. In summary, the operation of the ventilator shown in FIG. 6 can be described as follows. Let it be assumed that it is desired to operate the ventilator manually. When this is the case, the fitting 572 is inserted into the fitting 571. In addition, the diffusion interval metering valve 621 should be moved to the totally closed position and the volumetric exchange metering valve 617 should be moved to the totally open position. This serves to move the timing cartridge 598 to a closed position which prevents servoing the interval phasing cartridge 568 to its closed position and thus ensures that the oscillator timing circuit is under the control of the remote cycling valve 574. When this is the case it can be seen that by depressing the pushbutton 576 of the remote cycling valve 574, the oscillator timing gases will bleed off to ambient and will permit the flow oscillator cartridge 533 to oscillate under the control of the metering valves 541 and 544 as hereinbefore described. This causes gases to be supplied to the venturi jet 553 to the patient airway to supply gas at a predetermined frequency and pressure as determined by the setting of the metering valves 541 and 544 and the oscillatory amplitude metering valve 548 to thereby provide pulsatile gases at a predetermined pressure in the patient airway. During the time this is occurring, the patient can still exhale at a predetermined pressure through the shrouded venturi 557 and through the expiratory gate provided on the venturi manifold assembly 554. It is possible that some of the exhaled gases may pass through the oscillation valve assembly 562 during the negative phase of the pulsatile air flow from the flow oscillator 533. As soon as the pushbutton 576 of the cycling valve 574 is released, pressure will build up because the gases cannot exhaust to the atmosphere through the cycling valve from the timing oscillator reset cartridge 537 and gases will build up to servo the flow oscillator cartridge 533 to move it to the closed position to prevent further flow of gases into the patient airway. The patient then can exhale through the exhalation valve assembly 562 as well as through the expiratory gate provided in the venturi jet manifold 554. Pulsatile gases can be again introduced into the breathing circuit of the patient by depressing of the button 576.

Now let it be assumed that instead of manual phasing of the gases to the patient airway it is desired to have this accomplished automatically. This can be done by opening the volumetric exchange metering valve 617 to the desired position and closing the diffusion interval needle valve 621 to the desired position to provide the desired phasic cycling. The metering valve 617 determines the time "off" whereas the metering valve 621 determines the time "on". In addition the fitting 572 should be disconnected from the fitting 571 so that the oscillator timing gases are exact to the atmosphere through the fitting 571. Gases supplied to the patient will be pulsatile gases in the same manner as under manual operation. The patient will still be able to exhale any time even though pulsatile gases are being delivered to the patient and during the time that pulsatile gases are not being delivered to the patient in the manner hereinbefore described.

In FIG. 6A there is shown an oscillator circuit which can be utilized to replace the oscillator circuit in FIG. 6 which would include the flow oscillator cartridge 533, the timing oscillator reset cartridge 537, the interval phasing cartridge 568, the oscillator inspiratory metering valve 541, the oscillatory amplitude metering valve 548, the oscillator inspiratory isolation valve 538 and the oscillator expiratory metering valve 544. In their place would be substituted the circuitry shown in FIG. 6A which would be connected between point A which is connected to the outlet 603 of the timing manifold 602, and point B which would be connected to the outlet 526 of the master on/off switch 523 to provide source gas under pressure and point C which is connected to the outlet 549 of the oscillatory amplitude metering valve 548 and another terminal D which is connected to the outlet fitting 626. Source gas is supplied from the master on/off switch to the outlet 526 to the terminal B and to the inlet 641 to a normally open expiratory differential oscillator cartridge 642. The gas is supplied to an outlet 643 to an inlet 644 of an oscillation frequency rate metering valve 646. The metered flow of gas passes through an outlet 647 to a servo port 648 of the expiratory differential oscillator cartridge 642. At the same time, gas flow from the outlet 643 is supplied to the inlet 649 of a normally open inspiratory interrupter cartridge 651. Gas is supplied to an outlet 652 to an inlet 653 of an oscillator flow and secondary rate control metering valve 654. The metering valve 654 is provided with an outlet 656 for the main flow of gas to the venturi socket 551 and into the venturi jet 553 to the patient airway. Gas is also supplied by the metering valve 654 through an outlet 657 which is connected to the outlet fitting 626 that is connected into the reservoir (not shown). This commences the buildup of the pressure pulse. As soon as there has been sufficient pressure buildup behind the diaphragm of the expiratory differential oscillator cartridge 642, it is moved to a closed position to terminate the flow of source gas through the cartridge 642. As soon as this occurs, gas behind the diaphragm of the expiratory differential oscillator 642 will bleed in a reverse direction through the oscillation frequency rate metering valve 646 which will be supplied to the inlet 649 through the normally open inspiratory interrupter cartridge 651 through the outlet 652 through the metering valve 654 and through the venturi socket 651 to the patient airway which is open to ambient through the exhalation valve assembly 562. As soon as there has been sufficient bleed down of gases, the expiratory differential oscillator 642 moves to its normally open position to permit source gas again to flow through the same to restart the cycle for the next pulse.

Now let it be assumed that it is desired to utilize the ventilator circuitry shown in FIG. 6 and 6A in conjunction junction with a conventional respirator of the type described in the U.S. Pat. No. 4,060,078 which is provided with an inspiratory phase and an expiratory phase in its operative cycle. The terminal A of the circuit shown as FIG. 6A would be tied into a point in the conventional respirator in which it would sense the inspiratory flow of gases to the patient. When this occurs, the inspiratory flow would pass through a servo isolation check valve which is connected to the servo port 662 of the inspiratory interrupter cartridge 651. As soon as the diaphragm is pressurized, the inspiratory interrupter cartridge is moved to a closed position to terminate the flow of timing gases from the expiratory differential oscillator 642. The amount of time in which the inspiratory interrupter cartridge is maintained in a closed position is determined by the flow of gases through an oscillator delay and anti-surge metering valve 663 which has its inlet 664 connected to the servo inlet 662. It has an outlet 666 which is connected to the reservoir socket 626. Thus it can be seen that as soon as the pressure behind the diaphragm of the inspiratory interrupter cartridge 651 is bled down sufficiently, it will move to an open position to again permit the flow of oscillatory gases from the expiratory differential oscillator 642. In this way, it is possible to impose oscillatory pulsatile gas flow on to the main gas flow provided by the conventional respirator. By appropriate adjustment of the valve 664 it is possible to ascertain the positioning of the pulsatile gases onto the main, gas flow from the conventional respirator.

Now let it be assumed that the circuitry shown in FIG. 6A has been connected to point A shown in FIG. 6 in which the timing circuit of FIG. 6 is utilized in conjunction with the oscillator shown in FIG. 6A. When this is the case, as soon as a gas is supplied from the timing manifold 602 through the servo isolation check valve 661, the inspiratory interrupter cartridge 651 will be moved to a closed position to terminate the pulsatile flow of gases and also the pulsatile flow is terminated for a period of time which is determined by the time required to load the diaphragm of the timing cartridge 598 by gases passing through the volumetric exchange metering valve 617. As soon as the timing cartridge 598 moves to a closed position, the pressure in the timing manifold will drop to atmospheric through the reservoir refill orifice 614 by unloading the diaphragm in the timing reset cartridge 609 to permit it to move to an open position. As this occurs, the diaphragm of the timing cartridge 598 can be unloaded by gas bleeding through the diffusion interval metering valve 621 through the timing reset cartridge 609 into the reservoir socket 626.

While the space behind the diaphragm of the timing cartridge 598 was bleeding down, there was no flow of gas through the servo isolation check valve 661 but the gases behind the diaphragm of the inspiratory interrupter cartridge 651 will be bled down through the oscillator delay and anti-surge metering valve 663. As soon as this occurs, pulsatile gases will again be delivered to the patient airway. The desired mode of operation would be for the oscillator delay and anti-surge metering valve 663 to time out prior to timing out of the diffusion interval metering valve 621 to prevent the delay provided by the metering valve 663 to be more than the delay provided by the diffusion interval metering valve 621 and thereby ensure that oscillation will always take place.

In FIG. 6B there is shown an optional breathing circuit which can be utilized in place of the breathing circuit shown in FIG. 6. It consists of a nebulizer 586 of the type hereinbefore described. It also includes a tri-jet venturi assembly 671. The tri-jet venturi manifold 671 includes a central jet 673 surrounded by two additional jets 674 and 676. The central jet 674 would be supplied with the pulsatile gas flow supplied from the outlet socket or fitting 551. The other jets 674 and 676 could be supplied with inspiratory flow from a conventional respirator or in addition could be provided with a constant flow of gas from CPAP flow from a conventional respirator. The breathing circuit shown in FIG. 6B also includes an exhalation valve assembly 678 of a conventional type. The exhalation valve assembly 678 is provided with an inlet 679 which is supplied oscillatory gases from the venturi socket 551 so that it is moved to a closed position during the initiation of a pulse of gas. The inlet 679 is also connected to a metering valve 681 which opens to the atmosphere. This bleed off of gases provides a slight delay in the closing of the exhalation valve so as to partially delay the buildup of pressure within the patient airway at the commencement of a pulse of gas being supplied to the patient airway.

The breathing circuit shown in FIG. 6B also includes a subambient venturi assembly 683. This subambient venturi assembly 683 consists of a cylindrical body 684 which has a venturi-like passage 686 formed therein. One end of the body 684 is open to ambient whereas the other end has mounted therein a venturi jet 687 disposed in such a manner so that gases exiting from the jet will pass through the venturi passage 686. The venturi jet 687 is connected to a suitable source of gas such as a constant flow of gas or an intermittant flow of gas to provide the pressure drop within the venturi which is communicated by a tube 688 to the exhalation valve outlet port to supply a negative pressure to the underside of the diaphragm of the exhalation valve and to apply a negative pressure to the patient airway during the time that the exhalation valve is in an open position. The shrouded venturi 672 is provided with a fitting 689 which can be connected to the airway pressure gauge 631 to permit monitoring of the pressure in the patient airway.

Still another embodiment of the ventilator of the present invention is shown in FIG. 7. This also can be characterized as an intermittent percussive ventilator which is particularly adapted for home respiratory use. As will be seen as hereinafter described, it includes an oscillator circuit very similar to that described in the embodiment shown in FIG. 3.

A source of gas 701 is provided which is supplied to an outlet 702. The source of gas 701 can be a source of air or alternatively a source of air mixed with oxygen as supplied by a blender of the type hereinbefore described. Gas supplied to the outlet 702 is connected to the inlet 703 of a rotary master on/off switch 704 which is provided with a control knob 706. The switch 704 is provided with an outlet 707 which is connected to the inlet 708 of a normally closed manual inspiration valve 708. The valve 708 is provided with a pushbutton 709 for moving the same to an open position to supply gas through an outlet 711 which is connected to a venturi socket 712. A fitting 713 is provided for mounting in the socket 712 and is connected to a nozzle or a jet 714 carried by a manifold 716. The manifold 716 is part of a breathing circuit 717 and is mounted on a shrouded venturi assembly 718 of the type hereinbefore described in connection with previous embodiments. The shrouded venturi assembly 718 is adapted to be connected to the patient airway 719 in the manner hereinbefore described. An exhalation valve assembly 721 is mounted on the shrouded venturi assembly and has an inlet 722 which is connected to the fitting 713 so that when gas is supplied to the nozzle 714, gas is also supplied to the inlet 722.

Source gas is also supplied from the outlet 706 to an inlet 724 of a normally open flow oscillator cartridge 726. Gases are supplied from the outlet 727 through an inspiratory isolation check valve assembly 728 to an inlet 729 of the oscillator inspiratory time on metering valve 731. Metered gas flow is supplied through an outlet 732 to a servo port 733 for the flow oscillator cartridge 726. Gas is also supplied from the outlet 732 to an inlet 734 of an oscillator expiratory time off metering valve 736 which is provided with an outlet 737. The outlet 737 is connected to an inlet 738 of a normally open oscillator timing reset cartridge 739 and to an outlet 741. The outlet 741 is connected to a manual cycling socket 742. A fitting 743 is adapted to fit within the socket 742 and is connected to the inlet 744 of a manual cycling aerosol control switch 746 of the type hereinbefore described in conjunction with FIG. 5. It is maintained in a normally closed position and is provided with a pushbutton 747. The switch 746 forms a part of a nebulizer 748 of the type hereinbefore described in conjunction with FIG. 5. The switch 746 is mounted on the shrouded venturi assembly 718 in such a manner so that when the pushbutton 747 is depressed, the outlet 741 is in communication with the patient airway which periodically is open to ambient through the exhalation valve assembly 721.

Gas is also supplied from the outlet port 728 of the oscillator inspiratory time on cartridge 727 to the inlet 751 of an oscillatory amplitude metering valve assembly 752. Metered gases from the metering valve 752 are supplied through an outlet 753 which is connected to the venturi socket 712. Gas from the outlet 728 is also supplied to the servo port 754 of the oscillator time reset cartridge 739. The servo port 754 is also connected to the range compensator orifice 756 which is connected to a nebulizer socket 757. A fitting 758 is mounted in the nebulizer socket 757 and is connected to the venturi jet or nozzle 758 of the nebulizer 748.

Means is provided for sensing the airway pressure of the patient and consists of a gauge 761 which is connected through an adjustable gauge orifice 762 to a socket 763. A fitting 764 is provided for the socket 763 and is connected to a fitting 766 provided on the shrouded venturi assembly 718.

The valve 708A is provided with an outlet 710 which is connected through an orifice 711 of a suitable size such as 0.035 inches to a venturi socket or fitting 712. The orifice 711 is provided to ensure that a maximum pressure of approximately 40 centimeters of water is supplied to the airway of the patient from a 50 psi source.

Operation of the oscillator 699 in combination with the breathing circuit 717 may now be briefly described as follows. Let us assume that a patient at his home desires to utilize the same in connection with administering a certain drug which is placed within the nebulizer assembly 748. When the patient is ready to use the same, the breathing head can be connected to the airway of the patient in a suitable manner such as by the use of a mouthpiece. The knob 706 is turned on and then the pushbutton 747 is depressed. As soon as the pushbutton 747 is depressed oscillation of the oscillator circuit 699 commences to provide pulsatile gases through the fitting 712 to the venturi nozzle 714 into the airway of the patient while at the same time delivering gas to the nebulizer 748 through the socket 757 so that an aerosol containing the drug carried by the nebulizer is brought into the circumferential areas in the shrouded venturi assembly 718 so that it is also delivered to the airway of the patient and mixed with gas which is introduced through the central venturi.

Oscillation occurs in the same manner as described in conjunction with the embodiment shown in FIG. 3. As source gas is delivered to the flow oscillator 727 gas is supplied at the output 728 and gas passes into the range compensator orifice 756 and also through the oscillatory amplitude metering valve 752 into the venturi socket 712 into the venturi jet 714 into the airway of the patient. As soon as the flow passages have been overwhelmed pressure builds up in the servo port 754 of the oscillator timing reset cartridge 739 to move to a closed position. In addition, gas is supplied from the outlet 728 into the timing circuit through the expiratory isolation check valve 728 to the oscillator inspiratory time on metering valve 731 into the servo port 733 of the flow oscillator cartridge 727. This servos that diaphragm to move the cartridge to a closed position to interrupt the flow of gas from the outlet 728. As soon as the source gas is interrupted to the servo port 754, gas behind the diaphragm in the oscillator timing reset cartridge is bled down through the oscillator amplitude metering valve 752 into the airway of the patient to ambient through the exhalation valve assembly 721. At this time, air also bleeds out of the servo port 733 for the flow oscillator cartridge 727 through the outlet 734 of the oscillator expiratory time off metering valve 736 through the outlet 737 and into the inlet 738 of the oscillator timing reset cartridge 739 which is now in the open position through the outlet 741 through the manual cycling socket 742. If there has been inadequate buildup of pressure in the lines leading to the manual valve 746, the flow oscillator cartridge 727 will move to an open position permitting gas to flow from its outlet 728 to again cause source gas to flow through the venturi socket 712 to the airway of the patient. The same cyclic action takes place until there has been a sufficient buildup of gas in the lines leading to the manual cycling aerosol control valve 746 so that the diaphragm of the flow oscillator 727 will not move to an open position. When this occurs then further oscillation will cease.

It generally has been found that approximately two oscillations will occur before there has been a sufficient buildup in the lines leading to the manual cycling aerosol control valve assembly 746. Thereafter, oscillatory action can only be commenced by depressing the button 747 of the control switch 746 which empties the gases from the lines leading from the oscillator timing reset cartridge 739 into the venturi assembly 718 and into the patient airway. As soon as this occurs, the gas, pressure behind the diaphragm in the flow oscillator 727 will be bled out through the oscillator expiratory time off metering valve 736 through the oscillator timing reset cartridge and through the manual cycling aerosol control valve 746 to start the oscillatory action hereinbefore described causing pulses of gases to be continued to be supplied to the airway of the patient as long as the pushbutton 747 of the manual cycling aerosol control valve is depressed. An aerosol will be dispensed into the airway of the patient during the time the pushbutton 747 is depressed. There is supplied to the patient airway gas under pressure upon which there is superimposed pulses of gases with the oscillation of the flow oscillator cartridge 727. When the pushbutton 747 is released approximately two additional oscillations will occur until there has been a sufficient buildup of pressure within the lines leading to the control valve 746 to stop the oscillation of the oscillator circuit 699 hereinbefore described. These additional pulses after the pushbutton 747 is released cause a gradual decrease in the airway pressure and prevent against possible airway collapse which could possibly occur in the event of a sharp pressure drop in the proximal airway.

In FIG. 7A there is disclosed a schematic diagram of an optional circuit which can be utilized in conjunction with the ventilator shown in FIG. 7 to permit the ventilator in FIG. 7 to be selectively employed as either a volumetric or a diffusive device. This optional circuit consists of an oscillator-type cycle selector switch 767. This switch 767 is provided with an inlet port 767a which is adapted to be connected to the ports 732 and 733 in FIG. 7. It is also provided with a slidable valve member 768 which can be manually positioned in either of two positions to permit flow either through an outlet port 767b or through an outlet port 767c. Gas flow through the outlet port 767b flows into a rate reduction isolation check valve 770 to the port 734 in FIG. 7. The outlet port 767c is adapted to be connected directly to the port 734.

When the slidable valve 768 is moved to the left as viewed in FIG. 7A, gas will flow from the inlet port 767a through the outlet port 767c directly into the port 734 to permit operation of the ventilator as shown in FIG. 7 in the manner hereinbefore described. However, when the selector valve 768 is moved to the right as viewed in FIG. 7A, gas will no longer flow through the port 767c but will flow through the port 767b through the rate reduction reservoir 769 and through the reduction isolation check valve 770 to the port 734. This converts the device shown in FIG. 7 from a diffusive device to a volumetric respirator or ventilator. By connecting the reservoir 769 into the servo port 733, the servoing bleed down times are substantially increased so that the ventilator shown in FIG. 7 no longer acts as a diffusive respirator or ventilator but acts as a volumetric ventilator with cyclic rates below 100 cycles per minute.

From the circuitry shown in FIG. 7A it can be seen that the relatively simple ventilator which is shown in FIG. 7 can be programmed for either volumetric or diffusive ventilation manually by operation of the selector switch 767. This makes it possible for a ventilator such as shown in FIG. 7 as modified with the circuitry shown in 7A to permit the patient to be stabilized on diffusive ventilation and thereafter switched over to volumetric ventilation to conserve oxygen supplies during transport where the oxygen supply may be minimal. Thus, it can be seen that the modification shown in FIG. 7A can be utilized in conjunction with the ventilator of FIG. 7 to provide percussive therapy, diffusive and/or volumetric ventilation for critical care as well as for other conventional uses for ventilators.

In FIG. 8 there is shown a decompression expiratory oscillation module which can be utilized with the ventilator which is shown in FIG. 3. It is provided with terminals A and B which are adapted to be connected into the points A and B shown n FIG. 3. As can be seen, point A is connected into the source of oxygen for the ventilator shown in FIG. 3 whereas connection B is connected into the outlet 24 from the oxygen blender 21.

The decompression and expirator module 771 consists of a body 772 which has an aneroid 773 mounted therein which is exposed to ambient through an opening 774 and which is referenced to sea level. The aneroid 773 is connected to a valve stem 776. The valve stem 776 carries a valve member 777 which is adapted to be moved between open and closed positions with respect to a valve seat 778 formed in the body 772. The valve member 777 is yieldably urged towards a normally closed position by a spring 779 carried by the body 772. The body 772 is provided with an inlet 781 which is connected to the terminal A and as hereinbefore explained is connected to the oxygen source. The body 772 is also provided with an outlet 782 which is connected to the outlet 24 of the oxygen blender 21.

Let it be assumed that the ventilator with the decompression and expiratory oscillation module 771 is carried by a transport vehicle such as an aircraft flying at an elevation of 35,000 feet. Let it also be assumed that there has occurred on the aircraft an explosive decompression bringing about a pressure differential which can be as great as 9 psi. This pressure differential is immediately sensed by the aneroid 774 which expands and moves the valve member 777 to an open position to immediately permit oxygen to enter from the oxygen source into the outlet line connected to the outlet 24 of the oxygen blender so that there is a supply of 100 percent oxygen through the ventilator for use by the patient who has encountered this explosive decompression.

In FIG. 9 there is disclosed an automatic aneroid decompression relief valve assembly 786. It consists of a cylindrical body 787 which have an aneroid 788 mounted in one end of the same which is exposed to ambient through an opening 789 provided in the body 787. The aneroid 788 is referenced to sea level. The aneroid 788 is connected to a valve stem 791 which carries a valve member 792 that is adapted to be moved between open and closed positions with respect to a valve seat 793 carried by the valve body 787. The body 787 is provided with a fitting 794 which is connected to a large tube 796 that is adapted to be connected to the shrouded venturi assembly 323 shown in FIG. 3 in such a manner so that the tube 796 is connected at the head of the venturi-like passageway provided in the venturi assembly. The body 787 is provided with an additional annular valve seat 798 which is adapted to be engaged by a valve member 799. The valve member 799 is carried by valve stem 801. An armature 802 is mounted on the end of the valve stem and is adapted to be attracted by magnets 803 carried by the body 787. The body 787 is provided with an opening 804 which is open to the atmosphere.

Again assuming that the ventilator is being carried by a transport vehicle such as an aircraft flying at 30,000 feet and also assuming that an explosive decompression is encountered, it can be seen that the aneroid 788 will sense this decompression in the manner hereinbefore described and will move the valve member 792 towards an open position. This will vent the gases from the airway of the patient towards the gate valve member 799 to move it towards an open position against the force of the magnets attracting the armature 802 to vent the tube 796 to ambient through the opening 804. The gate valve member 799 serves to retain a governed pressure determined by the magnetic forces which are applied to the magnet 802 as for example a pressure of 20 centimeters of water. As flow increases through the gate valve 799 and through the opening 804, the magnetic forces attracting the armature 802 are reduced permitting an explosive flow of gas from the lung to thereby prevent pneumothoracy. Thus it can be seen that with the decompression and expiratory oscillation module provided in FIG. 7A and the automatic aneroid decompression relief valve assembly 86 there is provided means for accommodating an explosive decompression on an aircraft without endangering the life of the patient on which the ventilator is being utilized.

In FIG. 10 there is disclosed a pneumatic exhalation valve assembly which can be utilized with the various embodiments of the ventilators hereinbefore described. By way of example, it could be utilized in the ventilator shown in FIG. 7 in which it would be substituted for the venturi manifold 716, the shrouded venturi 718 and the exhalation valve assembly 721.

The exhalation valve assembly 816 shown in FIG. 10 consists of a generally cylindrical hollow body 817 which has a cylindrical passage 818 extending therethrough. An expiratory outlet 819 is mounted in the body 817 and is in communication with the passage 818. An additional outlet 821 is in communication with the passage 818 and is mounted n the body to extend diametrically therefrom and is utilized for sampling the airway pressure within the passage 818. The outlet 821 as shown is threaded into the body 817 and an O-ring 822 is provided to form an air-tight seal with the body. The passage 818 terminates in a proximal airway port 823 which is adapted to receive a suitable patient adapter such as a mouthpiece or endotracheal tube to be connected into the patient airway. A generally cylindrical venturi body 826 is provided and is sized in such a manner so that it can be slidably mounted within the passage 818 of the body 817. The body 817 is mounted within a cylindrical venturi bushing 827 in such a manner so that the bushing 827 moves with the venturi body 826. The venturi body 826 is provided with an annular flange 828 at its forward extremity which engages the forward extremity of the bushing 827. It is also provided with a centrally disposed annular flange 829 which also frictionally engages the bushing 827. At its rearmost extremity, the body 826 is provided with another annular flange 831 which engages a lip 832 that is L-shaped in cross section provided on the rear extremity of the bushing 827. The venturi body 826 is provided with a venturi-like passageway 833 which extends axially of the venturi body and opens through both ends of the venturi body 826. The forward extremity of the venturi body is provided with a chamber 834 in which a main inner groove 836 is provided and in which there is seated an O-ring 837. The O-ring 837 serves as a valve member and is adapted to engage a conical valve seat 838 which is formed in the body 817 immediately ahead of the expiratory outlet 819.

Means is provided for yieldably urging the venturi body 826 with its associated bushing 827 to a position so that the O-ring valve member 837 is moved out of engagement with the valve seat 838 and consists of a helical spring 841 which has one end seated against the lip 832 provided on the bushing 827 and has the other end engaging an annular abutment 842 formed in the venturi body 826.

The venturi body 826 is provided with a cylindrical threaded end 844 which has threaded thereon a cylindrical cap 846 which has portions of the same cut away to provide openings 847 which are in communication with an inlet 848 mounted in the body 817 and also in communication with the passage 818. The remaining portions of the cap 846 form L-shaped legs 849 which serve to support a nozzle 851 in a position so that a centrally disposed passage 852 extending therethrough is in axial alignment with the axis of the venturi-like passageway 833 provided in the venturi body 826. A nozzle or jet 851 is provided within the larger cylindrical bore 853 in axial alignment with the passage 852. An annular recess 854 is formed in the bore 853 and carries an O-ring 856. An end cap 858 is threaded into the outermost rear extremity of the body 817. An annular recess 859 is provided in the body 817 and receives the outer annular margin of diaphragm 861 formed of a suitable material such as neoprene. The diaphragm 861 extends across the inner face of the end cap 858 and carries a hollow diaphragm stem 862 having a flow passage 863 therein. The stem is adapted to be inserted into the bore 853 of the nozzle 851 and is adapted to establish a sealing engagement with the O-ring 856 so that an airtight seal is formed between the stem 862 and the nozzle 851. Passage 863 is in alignment and in communication with a flow passage 864 provided in the end cap 858. The end cap is provided with an inlet fitting 866 which is adapted to receive pulsatile air flow from a ventilator of the type hereinbefore described.

Operation of the exhalation valve assembly 816 in ventilators of the type hereinbefore described may now be briefly described as follows. Let it be assumed that the appropriate connections have been made to the exhalation valve assembly 816 from the ventilator as for example the ventilator shown in FIG. 7. Thus the fitting 713 would be connected to the fitting 866 provided on the end cap 858. The fitting 764 would be connected to the fitting 821 to provide the patient airway pressure. Now let it be assumed that pulsatile gases are being supplied to the venturi outlet 712 of the ventilator shown in FIG. 7. These pulsatile gases are supplied through the passage 864, through the passage 863, through the nozzle 851, through the bore 846 into the venturi-like passage 833 and thence into the patient airway. As the pressure introduced through the passage 864 overwhelms the orifice 852 provided in the nozzle 851, pressure is built up behind the diaphragm 861 to move the diaphragm with the hollow diaphragm stem 862 forwardly carrying with it the venturi body 826 with its associated bushing 827 forwardly in the body 817 until the O-ring valve member 837 engages the valve seat 838 provided in the body to close off the expiratory port or outlet 819. In this manner, the expiratory port is closed off in the same manner in which the exhalation valve assembly 721 is moved to a closed position by the application of air under pressure to the exhalation valve assembly. The advantage of the arrangement shown in FIG. 10 is that as soon as gas is no longer supplied to the exhalation valve assembly 816, the spring 841 returns the sliding venturi body 826 to its rearmost position determined by the rearmost position of the valve stem carried by the diaphragm 861.

It has been found that the combination venturi jet and exhalation valve assembly 816 has numerous advantages over the combination of the shrouded venturi assembly and the exhalation valve assemblies provided in the ventilators hereinbefore described. These advantages include rapid opening and closing of the expiratory port 819 which is accomplished in view of the fact that the sliding venturi body reacts very rapidly to the changes in gas pressure behind the diaphragm 861. Thus immediately upon receipt of gas in the nozzle 851, the diaphragm is actuated to move the sliding venturi body forward to close the expiratory port 819. Conversely, as soon as gas is no longer being introduced through the nozzle 851, the spring 841 rapidly returns the sliding venturi body to its original position. This makes possible a much higher frequency of oscillation with maximum stroke volume with a minimal oscillatory CPAP. An additional advantage is that there is very little dead space in the device ahead of the exhalation gate formed by the O-ring seal 837. This minimizes rebreathing. The device shown in FIG. 10 also has the advantage that only one power source is required for operation of the device whereas in previous embodiments two power sources were required. Another advantage of the device is that in the event of failure of the ventilator driving the device, the device assumes a fail-safe position which permits free breathing to ambient through the expiratory port 819. Even if the sliding venturi body 826 for some reason should happen to lock up in the closed position, the patient can still breathe through the venturi-like passageway 833 because of the clutching provided by the device. In addition, the exhalation valve assembly shown in FIG. 10 has the advantage in that it automatically remains in phase with inspiration. In addition, it is found that he construction of the present exhalation valve assembly also serves as a muffler to provide quiet operation of the venturi which is provided in the device.

Because there is low inertia in the parts forming the exhalation valve assembly shown in FIG. 10, it has been found that frequencies as high as 30 Hertz can be accomplished without getting out of phase.

In making a comparison between the volumetric ventilation which has been provided with ventilators used in the past and the diffusive ventilation which is accomplished with the ventilators of the present invention it should be appreciated that the volumetric ventilators delivered a tidal volume to the patient which was greater than the sum of the anatomical dead space in the airway of the patient and the mechanical dead space in the ventilator. With such volumetric ventilation, a cyclical rate of below 100 cycles per minute was utilized for neonates and cyclical rates below 100 were utilized for children with the rates for adults going down to as low as 10 cycles per minute. By way of example the typical lung capacity for an adult ranges from 3500 to 5000 milliliters. The tidal volume delivered to the patient by a volumetric ventilator will typically be in the range of 500 to 1000 milliliters.

On the other hand, utilizing diffusive ventilation with the ventilators of the present invention, successive volumes or stroke volumes or boluses of gas are delivered to the airway of the patient which are only a small fraction of the sum of the anatomical and mechanical dead space and which is only a small fraction of the total lung capacity of the patient. Thus by way of example for an adult human being having a lung capacity of 3500 to 5000 milliliters, the stroke volume or boluses of gas delivered to the airway of the patient under diffusive ventilation would range from 10 to 75 milliliters for each volume of gas. In addition, as a further comparison, the frequency rate of introduction of the successive stroke volumes or boluses of gas into the airway of the patient would always typically be in excess of 100 cycles per minute whereas with the diffuse ventilation ranging from two to seven Hertz, the equivalent cycles per minute rate is 120 to 420 cycles per minute. Thus it can be seen that the cyclic rate for diffusive ventilation is only a small fraction of the cyclic rate for volumetric ventilation. In the ventilators of the present invention, in addition to providing diffusive ventilation, it is possible either manually or automatically to superimpose upon diffusive ventilation, volumetric ventilation by supplying tidal volumes of gas to the airway of the patient. Alternatively, the diffusive ventilation can be terminated during the time that the tidal volumes are being delivered to the airway of the patient.

The ventilators hereinbefore described permit the use of advanced ventilatory concepts which allow most patients requiring ventilatory support to breathe spontaneously during long term cardiopulmonary management. Current routine volumetric ventilation with such ventilators with volume oriented type delivery frequently requires sedation or relaxation of the patient to prevent physiological/mechanical conflict. In the ventilators hereinbefore described no provision is made for fail-safe protection to cover the spontaneously breathing patient in the event of total ventilator failure. The breathing circuit which is shown in FIG. 11 is provided to give fail-safe protection in the event of such a ventilator failure. The breathing circuit 871 which is shown in FIG. 11 can be substituted by way of example for the breathing circuit 266 provided in the ventilator shown in FIG. 3.

As shown in FIG. 11, the connections to the breathing circuit 871 are through fittings 369, 406, 321 and 312 which are shown in FIG. 3. The breathing circuit includes an exhalation valve assembly 872 of the type which is shown in FIG. 10. A proximal airway swivel 873 is mounted on the forward extremity of the exhalation valve assembly 872 and is in communication with the port 822 provided in the body 817. The proximal airway swivel can be provided with the patient adapter (not shown) which can be connected to the patient airway represented symbolically by the balloon 876. The proximal airway swivel 873 is provided with an aspiration port 877 which is normally closed by a plug 878. The outlet 821 of the exhalation valve assembly 872 is connected to the fitting 369 which is used for monitoring the patient airway pressure. The inlet 848 of the exhalation valve assembly has mounted thereon an overpressure fail-safe relief valve 881. The valve 848 of the exhalation valve assembly has mounted thereon an overpressure fail-safe relief valve 881. The valve 881 provides pressure relief at a suitable pressure such as 10 centimeters of $H_2O$. The relief valve is provided with an outlet 882 which is mounted by a slip fit on the inlet 848. The relief valve 811 is provided with an inlet 883 which is connected to a large tube 884 which forms a part of the inspiratory side of the breathing circuit. The other end of the tube 884 is connected to an outlet 886 of a conventional 500 cc nebulizer 887. The nebulizer 887 is provided with an inlet 888 which is connected to an entrainment gate 889 that is mounted on the inlet 888. The gate 889 is connected to a cross 892. The cross 892 has an entrainment reservoir 893 mounted thereon as well as a volume regulator 894. The cross is also connected to a large tube 896 forming the expiratory side of the breathing circuit. The tube 896 is connected to the outlet 897, of a failsafe pulse regulator 898 which has its inlet 899 mounted on the outlet 819. The regulator 898 is provided with a servo port 901 which is connected into the venturi jet port 866 that is connected to the venturi fitting 321. Nebulizer fittings 312 and 406 are connected to the nebulizer port 902 and the auxiliary port 903 respectively of the nebulizer 887.

The fail-safe pulse regulator 898 is provided with an exhalation port 907 which is adapted to be closed by a diaphragm 906 pressurized from the servo port 901. The overpressure fail-safe relief valve 883 is provided with an exhalation port 909 which is normally closed by a diaphragm 908 which is adapted to be moved to an open position by a predetermined pressure at the port 909 as, for example, a pressure of 10 centimeters of $H_2O$.

The volume regulator 894 is provided with an underfill valve 911 through which ambient air can be entrained and is also provided with an overfill valve 912 which will open to ambient in the event excess gas is being supplied to the reservoir 893.

A slight graded retard in the opening of the pulse regulator 898 can be provided by installing an orifice (not shown) in the tubing connected to the servo port 901.

Operation of the breathing circuit shown in FIG. 11 may now be briefly described as follows for providing diffusion respiration. Auxiliary gas for entrainment is delivered from the ventilator shown in FIG. 3 through the fitting 406 to the auxiliary port 903 provided on the nebulizer 887. Venturi servoing gas is supplied from the fitting 321 to the venturi jet 866 of the exhalation valve assembly 872 into the servoing port 901 of the fail-safe pulse regulator 898. Nebulizer gas is delivered from the fitting 312 to the nebulizer port 902 of the nebulizer 887. Monitoring of patient airway pressures is provided by monitoring the gas at the port 821 and supplying the same to the fitting 369.

During the time that there is a dynamic flow of gas from the venturi jet 851, this flow of gas causes entrainment of additional gas from the large bore inspirator tubing 884, from the nebulizer 887 and from the entrainment reservoir 893. If more gas is required than that which is available in the reservoir 893, additional ambient air is supplied from the volume regulator 894 through the underfill 911.

As soon as the inspiratory phase has been completed and the gases are no longer being supplied to the venturi jet port 866, the exhalation valve assembly 872 moves to an open position and the first flow of expiratory gases will flow through the expiratory port 819 through the outlet 897 and through the large tubing 896 into the reservoir 893. The failsafe pulse regulator 898 has an opening delay causing part of the physiological expiratory flow to vent to ambient with the balance being delivered into the reservoir. Should the reservoir 893 become overfilled, gas is vented to ambient through the overfill valve 912 of the volume regulator 894. Since there is a slight delay in opening of the pulse regulator 898, the exhalation gases are released to ambient and are the gases having the highest carbon dioxide concentration.

During the exhalation phase exhalation gases cannot regress through the venturi into the inspiratory tubing 884 because of the directional check 889 downstream of the nebulizer 887. The entrainment isolation valve 889 is located downstream of the nebulizer 887 to prevent rain out of aerosol secondary to an upstream location.

During operation of the ventilator, a constant flow of aerosol is generated by the nebulizer/humidifier 887 which is supplied through the large tube 884 to the entrainment port 848 of the exhalation valve assembly 872. Flow through the nebulizer is increased by the introduction of gas through the auxiliary port 903. This fresh gas which is supplied through the tube 884 is the first gas which is entrained by gases leaving the venturi jet 851. The slower the oscillation drain by volumetric ventilation, the longer the expiratory phase and the greater the washout of the inspiratory circuit through the open orifice 907 of the pulse regulator 898 which is in very close proximity to the proximal airway of the patient. Therefore the first gas into the lung of the patient has the lowest carbon dioxide. As the oscillatory rates increase as during diffusion respiration, the flow around the breathing circuit increases with the associated increase in minute volumes. Because of the higher oscillatory rates and delay in opening of the pulse regulator 898, the majority of ambient flow occurs through the overfill valve 912 of the volume regulator 894.

The partial rebreathing circuit provided in the breathing circuit shown in FIG. 11 makes it possible to conserve breathing gases but at the same time allows control over hyperventilation, and gives better humidification of inspired gases and less temperature drop within the breathing circuit.

In the event that the expiratory circuit is overwhelmed by a massive early high pressure expiratory flow, the overpressure fail-safe relief valve 883 may purge a small initial volume of expiratory gases to ambient through the port 909 by causing opening of the diaphragm 908 until the pressure drops below 10 centimeters of $H_2O$. The overpressure fail-safe relief valve 883 prevents an overpressure as, for example, those above 10 centimeters of water in the inspiratory circuit.

During many diffusive ventilatory procedures, the patient will breathe spontaneously through a low level oscillatory CPAP. This is provided for by the rebreathing circuit shown in FIG. 11. During spontaneous inspiration entrainment is accelerated as proximal airway pressures rise causing less entrainment with flow of gas through the expiratory circuit being increased. Outlet flow to ambient is predominantly through the overfill valve 912 of the volume regulator 894.

During spontaneous demand by the patient, venturi flow is accelerated with entrainment of additional gases peaking with the demand of the patient. During expiration, the pulse regulator 898 clutches the flow to ambient breathing creating a CPAP sine wave. The failsafe pulse regulator 898 serves to vent the proximal airway to ambient with minimal mechanical dead space in the event of total mechanical ventilator failure permitting the patient to breathe spontaneously with little effort. If an occasion arises in which it is desired to wean the patient from the ventilator, the ventilator can be turned off while maintaining an aerosol delivery while the patient breathes essentially ambient air.

In the event there is any disconnect of any of the tubing in the ventilator, the breathing circuit in FIG. 11 still permits spontaneous breathing of the patient through the fail-safe pulse regulator orifice 907. A disconnect of the nebulizer and/or auxiliary tubing will cause entrainment of ambient air through the ambient access valve 912 of the volume regulator 894. An obstruction in the inspiratory tubing will reduce tidal volume by eliminating entrainment. However, in such event, the cap on the nebulizer may blow off or a large bore tubing will blow off to release trapped nebulizer and auxiliary flow of gases. An alarm will sound with a sustained rise in auxiliary gas pressure. A total obstruction in the expiratory tubing will only serve to reduce the oxygen concentration and slightly increase expiratory resistance. This result occurs because of entrainment of gas from ambient through the valve 894 of the volume regulator and the total exhalation of the exhalation gases through the orifice 907 of the failsafe pulse regulator 898.

In FIGS. 12 and 13, there is shown a quick disconnect assembly which is particularly adapted for use in the ventilators hereinbefore described. As shown, such a quick disconnect assembly 916 consists of female fitting 917 and a male fitting 918. The female fitting consists of a body 921. The body 921 is provided with a threaded cylindrical extension 922 which can be threaded into a panel or body to which gas is being supplied. The extension is provided with a bore 923 which opens into a cylindrical socket 924 in the body 921 and that is open at the other end of the body. The body 921 is provided with a plurality of flats 926 which are spaced circumferentially and are adapted to be engaged by a suitable wrench for screwing the fitting 917 into the body into which it is mounted. The body 921 is provided with an annular recess 927 adjacent the forward extremity of the same and carries a retainer 928. The retainer 928 is cylindrical in form and is provided with an inwardly extending annular flange 929 which is adapted to seat in the recess 927. The other extremity of the retainer is provided with an inwardly extending annular shoulder 931. The retainer 932 is provided with a plurality of axially extending slots 932 which are spaced circumferentially around the retainer to provide segmental lips on the clamping end of the retainer.

The male fitting 918 consists of a body 936 which is provided with a cylindrical hose extension 937 that is provided with spaced annular ribs 938. The extension 937 is adapted to receive the end of a tubular hose which frictionally engages the ribs 938. The body 936 is provided with a radially extending flange 941 and a forwardly extending straight bayonet 942. The body 936 is provided with a flow passage 943 which extends through the extension 937 and through the bayonet 942. The bayonet 942 is provided with a chamfer 944 on its outer extremity. The bayonet 942 is provided with an annular recess 946 which carries an O-ring 947. The bayonet 942 is also provided with an annular shoulder 948 which is provided with a tapered ramping surface 949. An annular recess 951 is formed between the shoulder 948 and the flange 941.

Operation of the quick disconnect assembly 916 may now be briefly described as follows. Let it be assumed that the female and male fittings 917, and 918 are separated and it is desired to connect the same. Let it be assumed that the female fitting 917 has been mounted in a body which is in a fixed position. The male fitting can then be inserted into the socket 924 by advancing the bayonet 942 forwardly into the retainer and so that the bayonet 942 enters the socket 924. As this occurs, the O-ring 947 will engage the wall of the socket 924 to form an airtight fit. As the advance of the male fitting into the female fitting continues, the inclined surface 949 on the shoulder 948 engages the rounded shoulder 931 provided on the retainer to circumferentially expand or cam outwardly the segmental lips so that the annular shoulder 948 can enter the retainer 928. As soon as the shoulder 931 clears the shoulder 948, the shoulder 931 will snap behind the shoulder 948 to seat within the annular recess 951 to thereby retain the male fitting 918 within the female fitting 917.

In the event it is desired to separate the male fitting from the female fitting, it is only necessary to apply a pulling force to the male fitting 918 which will engage the shoulders to cause the shoulders to expand outwardly the segmental lips of the retainer and to permit the bayonet 942 to be withdrawn from the socket 924.

When the male fitting 918 is mounted in the female fitting 917, the assembly is such that the male fitting 918 can rotate within the female fitting 917. The retainer 928 prevents a piston effect rejection of the bayonet during pressurization. Use of the retainer with the clamping retainer which is slotted to provide segmental lips provides adequate retention capabilities while at the same time facilitating the insertion and removal of the male fitting 918 from the female fitting 917. By way of example one design of the quick disconnect fitting assembly accommodated a static pull release of eight pounds. Under dynamic conditions with 50 pound piston effect, five pounds was the average release force.

The quick disconnect fitting assembly 916 as shown in FIGS. 12 and 13 can be utilized for interior and exterior fittings. Even though the assembly 916 has quick disconnect capabilities it can withstand high frequency use without showing wear.

Another embodiment of a quick disconnect assembly is shown in FIGS. 14 and 15. The disconnect assembly 956 shown therein is very similar to the disconnect assembly 916 shown in FIGS. 12 and 13. It consists of a female fitting or socket 957 and a male fitting or bayonet 958 and a retainer 959. Most portions of the quick disconnect assembly 956 are very similar to the corresponding portions in the previous embodiment with certain changes. Thus, the female fitting or socket 957 is provided with an annular surface 961 which extends substantially at right angles to the longitudinal axis of the quick disconnect assembly. Similarly, the male fitting or bayonet 958 is provided with a surface 962 which also extends substantially at right angles to the longitudinal axis of the quick disconnect assembly. The retainer 959 is provided with the annular flange 921 and an annular shoulder 931 as was the retainer 928. However in place of the narrowly generally U-shaped slots 932 provided in the retainer 928 V-shaped slots 963 are provided in the retainer 959. These V-shaped slots 963 extend longitudinally of the retainer and open through one end of the retainer carrying the inwardly extending annular flange 929 to provide a plurality of longitudinally extending flexible fingers 964. In the quick disconnect assembly 956, the retainer 951 is carried by the male fitting 958 and the female fitting 957 is provided with an annular camming surface 966 so that the flanged fingers 964 will engage the flange 966 and be cammed outwardly until they clear the forward extremity of the body 921 and drop into the recess 927 to latch the female and male fittings into a unitary assembly.

It has been found that by changing the conformation of the quick disconnect assembly as shown in the present embodiment with respect to the embodiment shown in FIGS. 12 and 13 and by utilizing various materials, the releasing force can be relatively precisely predetermined. Thus it has been found that by providing the V-shaped slots 963 in place of the U-shaped narrow slots 932, greater flexibility is provided in the fingers 964 to thereby lower the releasing force for the quick disconnect assembly. In addition it has been found that by providing the V-shaped slots, the number of times in which the assemblies can be connected and disconnected can be greatly increased before there is a possibility of failure. Thus it has been found that by using the V-shaped slots, connections and disconnections in excess of 5,000 repeat operations can be performed without any danger of failure. In addition the pull apart force can still be retained at desired valves even with the more flexible fingers by providing sharper angled surfaces as for example, the right angle surface engaged by the retainer 959 in the embodiment shown in FIGS. 14 and 15.

In determining the number of operations which can be readily assimilated by the quick disconnect assembly, the yield properties of the plastics utilized must be taken into consideration. For example where it is desired to provide a quick disconnect assembly which can withstand numerous connections and disconnections as for example, in excess of 5,000, materials shown as Nylon ST can be utilized for the bayonet whereas as polyethysulfone can be utilized for the retainer. Thus it can be seen that in constructing ventilators of the present invention utilizing quick disconnect assemblies of the type hereinbefore described the type of disconnect assemblies can be selected for the particular application. For example, where the quick disconnect assemblies are utilized for external fittings provided on the ventilator where there will be many repeated connect and disconnect operations during the lifetime of a ventilator, a quick disconnect assembly 15 of the type shown in FIGS. 14 and 15 can be utilized with the materials herein disclosed. On the other hand where the quick disconnect assemblies would be infrequently disconnected and connected during the lifetime of the instrument, the construction of the quick disconnect assembly shown in FIGS. 12 and 13 would be more appropriate.

It should be appreciated that the retainer 959 can be carried by either the female or male fitting. Since typically in the present embodiments of the quick disconnect assemblies the female fitting would be formed of metal and the male fitting of plastic, it generally would be preferable to have the retainer carried by the plastic male fitting rather than the longer lasting metal female fitting. However if desired, the retainer can be carried by the female fitting and still operate in generally the same manner.

The quick disconnect assemblies disclosed in the previous embodiments in addition to having the quick disconnect and connect features hereinbefore described also are immune to leaks. The O-ring 947 provides a positive seal in the quick disconnect assembly to prevent such leaks.

In FIGS. 16 through 21, there is disclosed a ventilator 971 incorporating the present invention. As shown in FIG. 16, the ventilator 971 is mounted upon a table 972 and is shown being utilized by a seated patient 973. The ventilator 971 consists of a console 974 which is connected to a breathing circuit 976. The console 974 consists of a case 977 which is formed of a suitable durable plastic such as Lexan. The case 977 is formed from a front bezel 978. The case also includes spaced parallel side walls 979 and 981, spaced parallel top and bottom walls 982 and 983 and a rear wall 984, all of which may be injection molded parts ultrasonically bonded together to form the case.

The bezel 978 is provided with an inwardly extending flange 986 which is disposed rearwardly from the front surface. Screws 985 are utilized for securing the bezel 978 to the sidewalls 979 and 981 of the case 977. The console 974 includes a front panel 987 that is secured to the flange 986 by suitable means such as screws 988. As can be seen from FIGS. 16 and 17, the front panel 987 is mounted on the left hand side of the bezel 978. The console 974 also includes a door 989 which is secured by a hinge 991 to a vertically extending strip 992. The strip 992 is secured to the flange 986 by screws 993. The door is provided with a knob 994 which is provided for rotating a latch member 996 carried by the door and adapted to engage the front panel 987 to hold the door in a closed position. The door when closed, encloses a compartment 997 in which the breathing circuit 976 can be stored when it is not in use.

U-shaped lips 998 and 999 are secured to the top and bottom walls respectively. The outside surface of the bottom U-shaped lip 999 is generally flush with the exterior surfaces of the side walls 979 and 981 and the rear wall 984 of the case 997 whereas the outside surface of the top of the U-shaped lip 998 is recessed from the same outer surfaces in such a manner so that one case can be stacked one above the other with the U-shaped lip 999 on the bottom of a case above nesting outside of the U-shaped lip 998 provided on the top of the case below.

A U-shaped handle 1001 is provided as a part of the case 977 and is secured to the side walls 979 and 981 of the case. The U-shaped handle 1001 has a size such and is rotatably mounted so that it can be swung 360° round the case. This makes it possible for the handle to assume various positions as hereinafter described. Suitable means is provided for securing the U-shaped handle 1001 to the side walls so that the handle can be rotated about the case. Such means consists of a serrated bushing 1002 which has serrations provided on one surface which are adapted to engage the plastic of the side wall. The serrated bushing 102 is provided with a threaded extension which extends through the side wall and which is retained in engagement with the side wall by a nut 103 threaded onto the threaded extension. A threaded shaft 104 is provided which extends through the end of the U-shaped handle 1001 and through an antifriction washer 1006 formed of a suitable material such as Nylatron and then through the bushing 1002 and is retained therein by a C-shaped clamp 1007.

A knob 1008 is secured to the other end of the threaded shaft 1004 and is provided for rotating the shaft. Since the shaft 1004 is threaded into the bushing 1002 it can be seen that by rotating the shaft relative to the bushing that the knob 108 can be used for clamping the ends of the U-shaped handle 1001 in the desired angular position. Thus as shown in FIGS. 16 and 17, the handle can be moved to a position that extends downwardly and slightly forwardly to cant the front panel in a slightly upward direction when the console is resting on the table 972. By loosening the knobs 1008 provided on the two sides of the case, it can be seen that the handle 1001 can be moved to other desired positions as for example, on top of the case to serve as a carrying handle or to the rear where it is in an out-of-the-way position. Since the handle 1001 can be rotated through 360°, the handle also can be utilized as a bracket for supporting the instrument on a stand or on a wall or on other pieces of equipment.

As can be seen from FIG. 16, the outside surface of the door 989 carries an illustration showing the manner in which the breathing circuits should be connected to use the ventilator. The front panel 987 carries a plurality of controls, sockets and the like as hereinafter described for operation of the ventilator. It will be noted that these controls on the front panel are recessed behind the front extremity of the bezel 978. This helps to insure that the controls provided on the front panel cannot be accidentally bumped to disturb their settings during the time that the ventilator is in operation.

As hereinbefore explained the case 977 can be formed of a suitable plastic such as Lexan. Also, the case can be made in such a manner so that it is substantially transparent so that the interior of the case can be inspected without the necessity of removing the front panel. The Lexon plastic which is utilized in the case can be given a suitable tint to approve the appearance as for example, it can be given a bronze tint. If desired, a dividing panel (not shown) may be placed inside the case to separate the storage compartment 999 from the compartment containing the equipment associated with the front panel 987. The case 977 can be provided with a plurality of knockouts if desired to make it possible to utilize the case for other types of ventilators as hereinafter described. In addition, the case is provided with a plurality as for example, two conical shaped recesses 1009 provided in the rear wall of the case which have recessed fittings mounted therein.

A schematic diagram of the pneumatic circuitry provided in the ventilator 971 is shown in FIG. 18. As shown therein, the ventilator 971 includes an inlet socket 1011 which is mounted in the upper rear recess (not shown) in the case. The inlet socket is connected to a conventional filter 1012. The inlet socket 1011 is adapted to be connected to a conventional source of air under pressure as for example, air having a pressure of approximately 55 psi. The filter 1012 serves to remove foreign material from the air and also condenses the water vapor therein. The water condensed out of the air is supplied through a pressure relief regulator 1014 to an outlet 1015. The pressure regulator 1014 is set to open in the event of a pressure in excess of a predetermined pressure as for example, 50 psi to exhaust the air to the atmosphere to prevent an overpressure condition from occurring. The outlet port 1015 is mounted in the lower recess (not shown) and if there is no water in the line as for example, in a hospital supply it can be capped. If there is water in the air as for example, in a home application in which the ventilator is being supplied with air from a small air compressor, a tube can be connected to the outlet 1015 and drained into a container which can be emptied after use of the ventilator.

The output from the filter 1012 is supplied through a pressure reduction regulator 1016. The pressure reduction regulator 1016 can be mounted on an inner wall of the case and is provided with a knob 1017 which is accessible from the compartment 997 so that it can be adjusted to the desired pressure, as for example, 40 psi. The gas under the reduced pressure from the regulator 1016 is supplied through a line 1018 to an adjustable orifice 1019 connected by a line 1021 to a manometer 1022. The manometer 1022 is typically mounted in the top wall 982 of the case 977. The manometer gives a direct reading of the pressure in psi of the gas or air which is supplied from the pressure reducing regulator 1016. The adjustable orifice 1019 serves to reduce the fluctuations in the gas on the manometer 1022 and serves to ensure that the manometer provides a mean pressure reading.

The output from the pressure reducing regulator 1016 is also supplied to a nebulizer limiting orifice 1026 which can be of a suitable size such as 0.040 of an inch. The orifice 1026 is connected to a socket 1027 mounted on the front panel 987 and typically can be color coded yellow. The socket 1027 is connected to a flexible plastic line 1028 also color coded yellow which is connected to a nebulizer 1029 hereinafter described in detail. As can be seen, a constant flow of gas is supplied to the nebulizer 1029 from the socket 1027. This provides a constant aerosolization to the patient.

Gas from the output of the regulator 1016 is also supplied to a manual inspiration limiting orifice 1031 of a suitable size such as 0.024 inches. The orifice 1031 is connected to a manually operated push button 1032. The manual push button 1032 is spring loaded to a normally closed position and can be moved manually to an open position against the force of the spring therein.

When the manual push button 1032 is depressed, it supplies gas to a socket 1033 provided on the front panel. The socket 1033 is connected to a flexible plastic line 1034 color coded white. The line 1034 is connected to a combination venturi jet and exhalation valve assembly 1036 of the type hereinbefore described. Thus it can be seen that the manual push button 1032 provides an override which makes it possible to cause the ventilator to act as a resuscitation device.

Gas is also supplied from the pressure reduction regulator 1016 to the inlet 1037 of an oscillator cartridge 1038. As shown, the oscillator cartridge 1038 is a normally open cartridge and is provided with a valve member 1039 movable between open and closed positions by a diaphragm 1041. When the cartridge 1038 is in its normally open position gas will flow from the inlet 1037 through an outlet port 1042 to a servo port 1043 of a reset cartridge 1044. The application of gas to the inlet 1043 causes pressure to be applied to a diaphragm 1046 which moves a valve member 1047 from its normally open position to a closed position to occlude the flow of gas from an inlet port 1048 to an outlet port 1049. At the same time that the flow of gas from the oscillator cartridge 1038 moves the reset cartridge 1044 from a normally open to a closed position gas is also supplied to an initial flow obtunder 1051.

The flow obtunder 1051 is shown in detail in FIG. 19 and as shown therein consists of a cylindrical body 1052 which is provided with a cylindrical extension 1053 that is adapted to have a hose or plastic line secured thereto. The body is provided with a cylindrical cavity or chamber 1054 which is in communication with a flow passage 1056 extending through the extension 1053. The flow obtunder 1051 also includes another body 1057 which is provided with a flange 1058 that is adapted to be ultrasonically bonded to the body 1052 to form an enclosed chamber or cavity 1054. The body 1057 is provided with an extension 1059 which is adapted to be connected to a hose or line. The body 1057 is provided with a cylindrical extension or protrusion 1061 which extends into the cavity or chamber 1054. A flow passage 1062 is formed in the extension 1059. Flow passages 1059 and 1062 are in communication with the chamber 1054 and in communication with passages 1063 extending diametrically from the cylindrical extension and protrusion 1061. A sleeve 1064 formed of a suitable flexible material such as plastic is slidably mounted on the cylindrical extension or protrusion 1061 and is disposed in an annular recess 1066 formed in the protrusion 1061 and is adapted to occlude the passages 1063. When gas is supplied to the passage 1062, the gas comes into engagement with the sleeve 1064 and gradually expands the same so as to permit air to flow around the sleeve and out to the passage 1056. In this way it can be seen that there is provided a gradual opening of the flow obtunder so that physiological structures in the patient are not abruptly struck with a burst of gas while at the same time the flow obtunder does provide a good peak flow after it has been gradually opened. Gas flowing from the flow obtunder 1051 is supplied to the socket 1033 which is connected to the combination venturi jet and exhalation valve assembly 1036.

Gas supplied from the outlet 1042 of the oscillator cartridge 1036 is also supplied through a check valve 1067 to the adjustable inlet 1068 of an impact metering cartridge 1069. The impact metering cartridge 1069 can be adjusted to control the flow of gas and this gas is supplied to an outlet 1071. The gas from the outlet 1071 is supplied to the inlet 1072 of a frequency metering cartridge 1073. The rate of flow through the frequency metering cartridge 1073 which also can be termed a rate metering cartridge can be adjusted as shown. This adjusted flow rate of gas is supplied through an outlet 1074 to the inlet 1048 of the reset cartridge 1044 which at this time is closed because of gas supplied to the servo port 1043. Because gas cannot flow through the reset cartridge 1044 there is a pressure build up and this gas under pressure is supplied to the servo port 1076 of the oscillator cartridge 1069 which applies pressure to the diaphragm 1041. The rate at which the diaphragm 1041 of the oscillator cartridge moves the valve member 1039 from an open to a closed position is determined by the rate of metered flow by the frequency metering cartridge. As soon as there has been sufficient build up of pressure against the diaphragm 1041, the diaphragm 1041 moves the valve member 1039 to a closed position to occlude the flow of gas from the inlet 1037 to the outlet 1042. As soon as the valve member 1039 oscillator cartridge 1038 is moved from an open to a closed position the flow of gas through the combination venturi jet and exhalation valve assembly 1036 which also can be termed a "phasitron" is stopped. The remaining gas in the lines is dumped very rapidly through the phasitron 1036 which reduces the pressure behind the diaphragm 1046 of the reset cartridge 1044 so that it rapidly moves from a closed position to its normally open position. As soon as this occurs, the gas which is trapped behind the diaphragm 1041 of the oscillator cartridge is bled out through the frequency metering valve or cartridge 1073 through the inlet 1048 through the outlet 1049 which is connected to a socket 1077 mounted on the front panel 987 and which can be characterized as a remote socket. The remote socket 1077 in certain applications of the ventilator 971 can be vented to ambient and therefore as soon as the gas pressure behind the diaphragm 1041 has been reduced sufficiently, the diaphragm 1041 will move the valve member 1042 to an open position to open the oscillator cartridge to again start the cycle hereinbefore described.

In certain applications of the ventilator 971 it may be desired to control the frequency of oscillation of the ventilator remotely. This is accomplished by connecting the remote socket 1077 by a line 1078 with both the socket and the line 1078 being color coded in an appropriate color, as for example, green. The line 1078 is connected to an inlet fitting 1080 of a manually operated push button assembly 1079 mounted on the tee 1141. Operation of the push button assembly 1079 by the user vents the line 1078 to ambient.

Means is provided for controlling the pressure of the gases in the airway of the patient and consists of an impact knob 1081 and having the letter "A" thereon. The knob 1081 is mounted on the front panel 987 and is used for adjusting the impact metering valve 1069. Similarly, a knob 1082 having the letter "B" thereon is provided on the front panel 987. It is used for adjusting the frequency metering valve 1073. The impact knob 1081 determines the inspiratory time and the frequency knob 1082 determines the expiratory time. The inspiratory time is the time that the oscillator cartridge 1038 is open and the expiratory time is the time that the oscillator cartridge 1038 is closed. As the impact metering knob 1081 is turned towards a closed position, the slower the rate of flow of gas through the same and the longer the oscillator cartridge 1069 will remain open or in the inspiratory phase to thereby lengthen the inspiratory time. The slower the rate of flow through the impact metering valve 1069, the longer it will take to load the diaphragm 1046 of the reset cartridge 1044 and thus the longer it will take the timing circuit to fill up. Conversely, the more that the knob 1081 is moved to an open position, the shorter the inspiratory time or the impact pulse to the patient.

With respect to the frequency knob 1082, the position of this knob determines the length of time that the oscillator cartridge 1069 will remain in a closed position. It therefore determines how much gas will flow out of the lung of the patient before the next inspiratory flow is started into the lung. Thus it can be seen that by adjustment of the knobs 1081 and 1082, an IE or inspiratory expiratory time ratio can be established.

Means is provided for monitoring the pressure of gases in the airway of the patient and consists of a line 1086 which is connected to the outlet of the phasitron 1036. The line 1086 is connected to a gauge socket 1087. The socket 1087 is connected to an orifice 1088 and the orifice 1088 is connected to a manometer 1089 mounted in the front panel 987 which gives a reading of the proximal airway pressure. The orifice 1088 serves to snub out pressure variations so that the manometer provides a mean reading of the patient's proximal airway pressure. The line 1086 and the socket 1087 also can be color coded in an appropriate color, as for example, red. As can be seen from FIG. 16, the proximal airway pressure is measured immediately behind the fitting 1091 which is secured to the phasitron 1036. The fitting 1091 is adapted to be connected to a patient adapter (not shown).

The nebulizer which is used in conjunction with the present ventilator 971 is shown in more detail in FIGS. 20 and 21. As shown therein it consists of a cup-like member 1096 which is provided with a cylindrical sidewall 1097 and a dished bottom wall 1098. The cup-like member 1096 is formed with a depending rim 1099 which is provided with a lower planar surface 1101 which is adapted to rest upon a flat surface to facilitate filling of the cup-like member 1096. The rim 1099 is provided with a cutout 1102 through which the yellow line 1028 can extend and is connected to an elbow 1103. The elbow 1103 is bonded by suitable means such as ultrasonic welding to a protrusion 1006 formed integral with bottom wall 1098. A central hollow post 1107 formed integral with the dished bottom wall 1098 extends vertically upward from the dished bottom wall 1098. A flow passage 1108 is provided in the protrusion 1106 and the post 1107. The top of the post 1107 is provided with a small orifice 1109 which is communication with the passage 1108. The top of the post 1107 is provided with a convex surface 1111.

The cup-like member 1096 is provided with an enlarged cylindrical portion 1112 adjacent to the dished bottom wall 1098 which is provided. A sleeve 1114 is mounted over the post 1107 and is ultrasonically bonded onto the cylindrical portion 1112. The sleeve has an inner cylindrical passage 1116 which is of greater diameter than the outer diameter of the post 1107 and is in communication with a plurality of passages 1113, as for example, four which are circumferentially spaced 90° apart around the raised portion of 1112. The sleeve 1114 is provided with an upper wall 1117 which extends across the cylindrical passage 1116 in a position slightly above the top of the post 1107. The wall 1117 is provided with a dished recess 1118 concave in form in communication with a venturi-like flow passage 1119 in vertical alignment with orifice 1109 and which is of a slightly greater diameter than the orifice 1109. By way of example, the orifice 1109 can have a diameter such as 0.030 whereas the orifice or passage 1119 can have a diameter such as 0.050. The sleeve 1114 is provided with cutouts 1121 on opposite sides above the wall 1117. The sleeve is also provided with another top wall 1122 which has a bore 1123 therein. The bore 1123 is adapted to receive a diffractor plug 1124. The lower extremity of the diffractor plug is provided with a convex surface 1126 which overlies the orifice 1119. The upper extremity is in the form of a knurled cap 1127 to facilitate placement and removal of the plug 1124.

The nebulizer 1029 also includes a quick disconnect cap 1131 which is adapted to be secured to the top of the cup-like member 1096. The cup-like member 1096 is provided with outwardly extending segmented lips 1132. The upper extremity of the cup-like member 1096 is provided with an annular recess 1133 with is adapted to receive an O-ring 1134 formed of a suitable material such as Silastic. The cap 1131 is provided with segmented U-shaped portions 1136 which are adapted to frictionally engage the segmented lips 1132 provided on the cup-like member 1096 so that the cap can be cammed down on top of the O-ring 1134 to form a liquid-tight seal.

The cap 1131 is provided with a cylindrical depending extension 1138 which is disposed over the top of the sleeve 1114 as shown in FIG. 20. The cylindrical extension 1138 is provided with a flow passage 1139 which opens into a tee 1141 formed integral with the cap. In one leg 1142 of the tee 1141, a flapper valve 1143 is provided which normally rests against a spider-like retainer 1144 which ensures that the flapper valve can only open in an inward direction. The other leg 1146 of the tee 1141 is adapted to be connected to the inlet port of the phasitron 1036. As can be seen, a manually operated push button valve 1079 is secured to the lower portion of the leg 1146 and opens into the tee. When the push button 1079 is operated, the line 1078 connected to the inlet 1080 is vented into the interior of the leg 1146.

With the construction shown, it can be seen that the gases which exit from the sleeve 1114 are introduced upwardly into the flow passage 1139 provided in the cylindrical extension 1138 and will exit into the tee 1141 where they will be carried into the phasitron 1036. As hereinbefore described, the phasitron is a device which provides a negative ambient pressure at the outlet from the tee 1141 so as to enhance the travel of the humidified gases from the nebulizer 1096 to the airway of the patient. The cylindrical extension 1138 depending down into the cup-like member 1096 serves as an anti-spill device. For example, with the present nebulizer, it is be possible to have as much as 20 ccs of liquid in the nebulizer without spilling it in the event that the nebulizer is tipped.

The outlet from the combination venturi jet and exhalation valve assembly 1036 is connected to a hose 1148 which is provided with straight corrugations. The hose 1148 is a suitable length, as for example, 18 to 24 inches and serves to collect water which may be contained within the exhaled gases passing through the exhalation outlet. It has been found that the corrugations in such a length of hose are adequate to retain any moisture which may precipitate out of the exhaled gases during a treatment. After the treatment, the hose can be removed and stretched and cleaned to remove the water therefrom so it can be ready for the next use. In this way, water is prevented from dripping onto the patient during use of the ventilator.

In operation of the nebulizer 1029 shown in FIGS. 20 and 21, a constant flow of source gases is supplied to the nebulizer at a pressure of, for example, 40 psi which in the nebulizer fractionates the liquid into particles having a mean average size of approximately six microns. Typically a nebulizer of this size can put out approximately 120 milliliters an hour. It can be seen that when gas is introduced into the elbow 1103 and passes through the orifice 1109 that any liquid within the cup-shaped member 1096 will be drawn up by a capillary attraction through the passage 1113 through the passage 1116 and then be introduced with the air through the orifice 1119 against the diffractor 1129. The diffractor causes the liquid entrained in the air to be broken up into very small droplets and to be discharged through the cutouts 1121 in the sleeve 1114. By providing a plurality of passages 1113 at different angular positions and by providing the concave or dish-shaped bottom wall 1098 for the cup-like member 1096, the nebulizer can be held in various orientations and still remain operative. The large surface areas provided by the outer surface of the center post 1107 and the inner surface of the sleeve 1114 facilitate adhesion of the liquid as it is drawn up by capillary attraction in the nebulizer. The orifice or passage 1119 serves in effect as a throat of a venturi to cause a pressure drop across the top of the post 1107 to facilitate movement of liquid by capillary attraction. It is also believed that this particular nebulizer particularly efficacious in causing the water particles to be charged with positive ions which inhibits coalescing of the water particles into a liquid before the water particles enter the patient airway.

Also in operation of the nebulizer 1029, the flapper valve 1143 is operated inwardly as soon as a pressure differential of approximately 1 to 2 centimeters of water occurs which allows additional ambient air to be entrained into the phasitron and delivered to the patient's airway. When humidified gases are delivered from the nebulizer 1029 to the phasitron or combination venturi jet and exhalation valve assembly 1036, the gases will overwhelm the orifice and the servo diaphragm 61 will cause the venturi body 826 of the combination venturi jet and exhalation valve assembly 1036 to move forward to close the exhalation valve. The gases introduced into the venturi jet assembly 1038 create a subambient condition which causes the flapper valve 1143 to open additional ambient air entrained. The ambient air moves across the top of the outlet of the nebulizer creating an additional vacuum and causing additional humidified gases to be delivered into the airway of the patient. The remainder of the operation of the combination venturi jet and exhalation valve assembly 1036 is in the manner hereinbefore described.

Another embodiment of a ventilator incorporating the present invention is shown in FIGS. 22 through 23. The ventilator 1151 shown therein is mounted upon a floor stand 1152. The floor stand 1152 consists of a five legged pedestal 1153 which is provided with locking casters 1154. A center post 1156 is mounted in the pedestal 1153. A bracket 1157 is mounted on top of the center post 1156 and engages the U-shaped handle 1011 carried by the case 977. Another bracket 1158 is secured to the arm 1011 and has clamped thereto an arm assembly 1159. The arm assembly 1159 includes a L-shaped arm 1161 and a telescoping L-shaped arm 1162 which telescopes into the arm 1161 through a coupling 1163. A flexible extension 1164 is carried by the end of the arm 1162 and carries a breathing head assembly 1166. A ring 1167 is secured to the bracket 1158 and carries a nebulizer 1029 of the type hereinbefore described. [A line 1168 is provided which is connected to the rear of the case of the ventilator and is adapted to be connected to a suitable source of gas under pressure as for example a source of gas under pressure in a hospital.]

A schematic diagram of the ventilator shown in FIG. 22 is shown in FIG. 23. As shown in FIG. 23, the pneumatic circuitry is very similar to that utilized in connection with the ventilator 971 hereinbefore described in conjunction with FIGS. 16 through 21.

All of the elements in FIG. 23 which correspond to those in FIG. 18 have been designated with the same identifying numerals. The additional components provided in FIG. 23 include a master on/off switch 1171 which is provided with a control knob 1172 accessible from a front panel 1173 mounted in the case 977. The two control knobs 1081 and 1082 provided in the previous embodiment have been moved up on the control panel so that all of the three knobs 1081, 1082 and 1172 are in vertical alignment. The manual on/off switch 1171 turns the ventilator on and off from the front panel when the ventilator is connected to a supply of gas.

Ventilator 1151 also includes a constant positive airway pressure cartridge 1174 which has an inlet 1176 that is connected to the outlet of the pressure adjusting regulator 1016. The cartridge 1174 is also provided with a servo port 1177 which is connected by a line 1086 to the combination venturi jet and exhalation valve assembly 1036 to sense the patient airway pressure. The cartridge 1174 is also provided with an outlet 1178 which is connected to the socket 1033. An adjustable metering valve 1181 is placed in pneumatic circuitry just ahead of the flow obtunder 1051. The adjustable metering valve 1181 is provided with a knob 1182 which is accessible from the front panel 1173 and immediately below the meter 1089.

It should be appreciated that although in the schematic diagram shown in FIG. 23 that both the adjustable metering valve 1181 and the flow of obtunder 1051 have been provided in series in the same circuit, that the typical application would utilize either one or the other because the two in series would provide too great a pressure drop. Thus in one embodiment of this ventilator, the flow obtunder 1051 would be used without the adjustable metering valve 1181 and conversely in another embodiment the adjustable metering valve 1181 would be used in place of the flow obtunder 1051.

The ventilator 1151 also includes an additional check valve 1183 which is placed in series with the servo port 1043 of the reset cartridge 1044 and a fixed orifice 1185 of a suitable size such as 0.018 inches and in series with either the adjustable metering valve 1181 or the initial flow obtunder 1051 depending which is present. The orifice 1185 serves a timing circuit dump orifice. In a typical ventilator only one of two, the metering valve 1081 or the flow obtunder 1051 would be used.

The sockets 1027, 1077, 1033 and 1087 provided on the front panel 1173 are shifted from below the manometer 1089 as shown in FIG. 17 to the right hand side of the panel 1173 and are arranged in the same order from the top to the bottom. In addition, the pushbutton 1032 has also been moved to the upper right hand side of the panel 1173 so it is positioned above the sockets hereinbefore described.

The breathing circuit 1193 shown in FIG. 22 is provided as a part of the ventilator 1151 and consists of the nebulizer 1029 which is connected to a tee assembly 1194. The tee assembly is connected to a rebreathing bag 1196 of the type hereinbefore described. The tee is connected to a breathing tube 1197 which is connected to a combination venturi jet and exhalation valve assembly 1036. Another breathing tube 1198 is also connected to the exhaust side of the combination assembly 1036 and is connected into the tee assembly 1194 which is connected to the rebreathing bag 1196. A water trap 1199 is connected into the breathing tube 1198 and is used for collecting water which precipitates out of the exhaled gases.

An illustration 1184 is provided on the outside of the door 989 to indicate to the user how the ventilator is to be connected.

The operation of the ventilator shown in FIG. 23 is very similar to that described in conjunction with the ventilator shown in FIGS. 16 through 21. The ventilator is turned on and off by the use of the knob 1172 of the master on/off switch 1171. When it is turned on, gas flows in the manner hereinbefore with the previous embodiment. Gas is supplied through the line 1034 to the combination venturi jet and exhalation valve assembly or phasitron 1036 through the fitting 1091 into the airway of the patient. Humidified gases from the nebulizer 1029 are also supplied to the phasitron 1036. In the present embodiment of the ventilator, the constant positive airway pressure cartridge 1174 is always being supplied with the pressure of gases in the patient's airway. When the pressure in the airway drops below a predetermined value as determined by the setting on the cartridge 1174, additional source gas is supplied to the socket 1033 through the outlet 1178 of the cartridge 1174.

Any pressure build up in the passages leading to the socket 1033 normally would affect the operation of the reset cartridge 1044. This however is prevented by the isolation check valve 1183 which isolates the reset cartridge 1044 from any pressure created by the CPAP cartridge 1174. By providing this isolation check valve 1183 it is possible to provide a constant positive airway pressure for the patient while at the same time retaining cyclic operation of the ventilator. Thus with the present ventilator it is possible to provide a base constant positive airway pressure to the patient while at the same time scheduling cycling in the desired manner with the desired IE ratio by adjustment of the knobs 1081 and 1082.

The rate of inspiratory flow during the inspiratory phase can be adjusted by adjustment of the knob 1182 to increase or decrease the flow as desired while still retaining the capability of varying the inspiratory expiratory ratio in the desired manner. In this way it is possible to take care of a great variety of patients. By cutting down on the flow of gas by use of the adjustable metering valve 1181 it is possible to gradually wean a patient from use of the ventilator. Great variations in timing can be obtained. For example oscillations varying from 400 to 800 cycles per minute can be readily obtained. Because of these capabilities, the ventilator is particularly useful in treating obstructive pulmonary disease as well as cardiovascular and cardiopulmonary diseases. It also can be utilized for weaning or for acute heart failure and a multitude of other therapeutic activities.

In FIG. 24 there is shown a wave form diagram showing the manner in which the ventilator 1151 operates. Thus, there is provided a wave form 1186 which shows active or percussive phases 1187 and pause or resting phases 1188. Each percussive phase includes a plurality of inspiratory peaks or phases and a plurality of expiratory phases or peaks with the inspiratory peaks being represented by the upwardly pointing peaks 1189 and the expiratory peaks being represented by the downwardly extending peaks 1191. It will be noted that during the time these measurements were being made that near the right hand end of the wave form 1186, the amplitude was increased substantially by adjustment of the knob 1182 without increasing or decreasing the IE ratio or appreciably changing the length of the inspiratory expiratory periods.

Still another embodiment of a ventilator incorporating the present invention is shown in FIGS. 25 through 31. The ventilator 1201 shown in FIG. 25 is in many respects similar to the ventilators hereinbefore described. It includes a stand 1152 which has mounted thereon a ventilator module 1202, an accessory module and a monitor module 1204. All three of the modules are provided with a case 977 and a handle 1011 of the type hereinbefore described. The cases 977 are provided with lips which can seat or nest within each other so that the modules can be stacked one above the other as shown in FIG. 25 and be supported on a single stand 1152.

Figure 26:
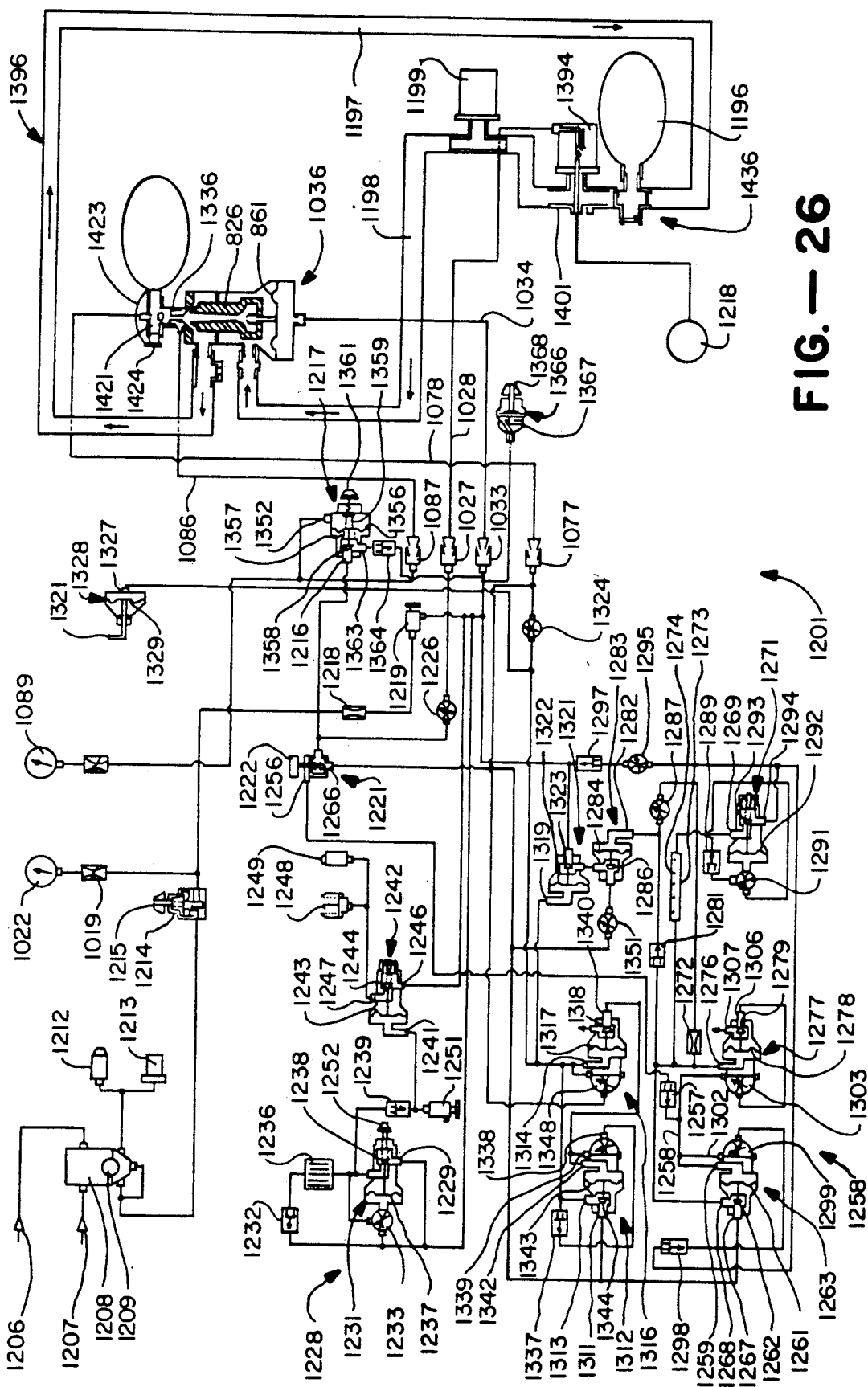
FIG. 26 is a schematic diagram of the pneumatic circuitry utilized in the ventilator shown in FIG. 25.

The schematic circuitry for the ventilator 1201 is shown in FIG. 26. As shown therein, sockets 1206 and 1207 are provided on the rear of the accessory module 1203. The socket 1206 is adapted to be connected to a suitable source of oxygen under pressure as for example approximately 50 psi and similarly, the socket 1207 is adapted to be connected to a suitable source of air under pressure, as for example a source having an approximate pressure of 50 psi. The sockets 1206 and 1207 are connected to a conventional oxygen blender 1208 which is mounted in the accessory module 1203 and which is provided with a control knob 1209 accessible from the front panel 1211 of the accessory module 1203. By adjustment of the knob 1209, the ratio of oxygen to air can be adjusted to suit the needs of the patient.

The output of the blender 1208 is connected to an alarm light 1212 and an audible alarm 1213, both of which are mounted on the front panel 1211 to give an alarm in the event that gas of inadequate pressure is supplied by the blender 1208.

Gas is supplied from the output of the blender 1208 to an operating pressure regulator 1214. The output of the regulator 1214 is supplied through an orifice 1019 of the type hereinbefore described to a manometer 1022 which measures the outlet pressure of the gas from the regulator 1214. The regulator 1214 is adjusted to provide the desired output pressure, as for example approximately 40 to 50 psi for an adult and ranging from 20 to 30 psi for a neonate. The regulator 1214 serves a dual function in that it stabilizes the inlet pressure to the patient and in addition it tailors the pressure to the size of the patient.

Gas from the regulator 1214 is supplied to an inlet 1216 of a demand constant positive airway pressure regulator 1217 hereinafter called demand CPAP regulator. Gas from the regulator 1214 is also supplied through a limiting orifice 1218 to a manual pushbutton valve 1219 on the front panel 1223 to the socket 1033. Socket 1033 is connected by line 1034 to a combination venturi jet and exhalation valve assembly or phasitron 1036. As pointed out with respect to the previous embodiments, the operation of the pushbutton 1219 overrides all of the other functions in the ventilator and provides manual resuscitation for the patient.

Gas is also supplied from the regulator 1214 through a master on/off switch 1221 which is provided with a control knob 1222 accessible on the front panel 1223 of the ventilator module 1202. Gas in addition to being supplied to the master on/off switch 1221 is also supplied to a nebulizer metering valve 1226 which is connected to the nebulizer socket 1027 and which is connected by the line 1028 to a nebulizer 1225. The nebulizer metering valve 1226 is provided in place of an adjustable orifice provided in the previous embodiments of this invention and has a knob 1227 on the front panel 1223.

From the foregoing pneumatic circuitry, it can be seen that a number of the components of the ventilator bypass the master on/off switch 1221 which makes certain functions obligatory as soon as source gas is connected to the ventilator. Thus, the demand CPAP regulator 1217, the manual inspiration valve 1219, as well as the nebulization provided through the nebulization metering valve 1226 bypass the master on/off switch 1221. In addition, the failsafe alarm system 1228 bypasses the switch 1221.

Gas is delivered from the outlet of the manual inspiratory valve 1219 to the inlet 1229 of a normally closed failsafe sensitivity cartridge 1231. Gas is also delivered to one side of the one-way check valve 1232. Since gas cannot flow through the check valve 1232, gas pressure will build up and enter the mean pressure rise calibration valve 1233 which is adjusted internally to provide a predetermined rate of flow of gas into a mean pressurized reservoir 1236. This rate of flow can be adjusted to any suitable predetermined value, as for example, one which will cause a sufficient pressure rise within one to two seconds to move the diaphragm 1237 of the failsafe sensitivity cartridge 1231 to move the valve member 1238 to an open position. This permits gas to flow from the inlet 1229 of the cartridge 1231 through a failsafe loading check valve 1239 to a servo port 1241 of a failsafe cartridge 1242. The gas pressurizes the diaphragm 1233 to move the valve member 1244 to an open position. This locks the failsafe cartridge 1231 in the open position so that gas supplied through the manual inspiration valve 1219 is supplied to an inlet 1246 through an outlet 1247 which is connected to a failsafe governor alert 1248 and also to a visual alert 1249.

It can be seen that this failsafe circuitry prevents an overpressure from being applied to the patient airway either through the manual inspiration valve 1219 or through the demand CPAP regulator 1217. The failsafe alarm circuit 1228 remains in a locked out position until the gas behind the diaphragm 1243 of the fail-safe cartridge 1242 is relieved as for example via the alert reset manually operated pushbutton 1251. As soon as this occurs, the failsafe cartridge 1242 returns to its normally closed position. In addition to the adjustment provided on the calibration valve 1233, the failsafe cartridge is provided with a knob 1252 on the front panel 1223 which can be utilized for adjusting the spring pressure applied to the diaphragm 1237 to thereby adjust the opening and closing pressure for the valve member 1238 operated by the diaphragm 1237. The fail-safe governor alert 1248 acts as a purge for the gases supplied to it in addition to reacting as an audible alarm. From the foregoing description it can be seen that the failsafe alarm circuit 1228 is always effective even though the master on/off switch 1221 is not turned on.

When the master on/off switch 1221 is in the off position, gas is supplied from the regulator 1214 through an outlet port 1256 of the master on/off switch 1221 which can be called the autophase port and is supplied to an autophase isolation check valve 1257 and then the gas is supplied to a phasing segment 1258 of a conventional ventilation circuit. This circuit supplies gas to a servo port 1259 to actuate a diaphragm 1261 to move a valve member 1262 from its normally open position to a closed position of an inspiratory cartridge 1263. Thus it can be seen that the inspiratory cartridge 1263 is moved to a closed position by the auto phase circuit of the master on/off switch 1221 at the time source gas is connected to the ventilator 1201 prior to the master on/off switch being turned on to prevent a sudden rush of inspiratory air gas to the airway of the patient represented by the schematic pulmonary structure 1264 through the inspiratory cartridge 1263. Thus it can be seen that before the master on/off switch 1221 is turned on demand CPAP is functioning, the manual override is functioning and the nebulization apparatus is functioning. In addition, the failsafe systems are functioning and the autophase system is functioning. With the master on/off switch turned off, the ventilator serves as an excellent weaning system. In addition, the CPAP cartridge which is in operation provides excellent ventilation to a patient if the patient had a left-sided heart failure to thereby provide effortless inspiratory breath while at the same time providing a positive airway pressure. In addition, manual override is provided if it is needed.

The conventional ventilatory system which is a time cycled ventilator and the diffusive high frequency ventilatory system can now be described. The master on/off switch 1221 is turned on and gas is supplied from its outlet port 1266 to the inlet 1267 of the inspiratory cartridge 1263. This inspiratory cartridge 1263 which can be called a monopulse cartridge or in other words a time cycled ventilator is normally open but is closed because of operation of the autophase circuit hereinbefore described when source gas pressure is applied to the ventilator 1201.

Let it be assumed that the inspiratory cartridge 1263 opens in a manner hereinafter described. When the cartridge 1263 opens, the valve member 1262 will open to permit flow of gas from the inlet 1267 through the outlet 1268. The gas is supplied to an inlet 1269 of a normally closed transition delay cartridge 1271 and therefore the gas can flow no further. Gas from the outlet 1268 is also supplied through a range compensator orifice 1272 of a suitable size such as 0.013 inches. The range compensation orifice 1292 bleeds into a perforated ambient muffler in the form of tubing 1273 which is provided with a plurality of holes or perforations 1274 which slowly leak gas out of the system to ambient. This prevents a lockout of the system and ensures that the system will keep on cycling.

Gas from the outlet 1268 is also supplied to the servo port 1276 of a normally open inspiratory reset cartridge 1277. Gas is supplied to a diaphragm 1278 which moves the valve member 1279 to a closed position. Gas is also supplied from the outlet 1268 of the inspiratory cartridge 1263 through a base line isolation check valve 1281 to a servo port 1282 of an interruption interval cartridge 1283. The application of gas to the servo port 1282 acts upon the diaphragm 1284 to move the valve member 1286 to a closed position. This servo port 1282 is connected to a base line pause needle valve 1287 which is provided with a knob 1288 accessible on the front panel 1223. The needle valve 1287 is used to bleed the circuit which pressurized the diaphragm 1284. The base line pause needle valve 1287 is connected to the perforated ambient muffler or tubing 1273.

As hereinbefore described gas is supplied from the outlet 1268 of the inspiratory cartridge 1263 to the inlet port 1269 of the transition delay cartridge 1271. At the same time gas is supplied to the outlet of a transition reset check valve 1289 to ensure that no gas can flow through the check valve 1289. Gas is also supplied to a transition delay time needle valve 1291 which is adjustable internally of the case 977 and supplies gas at a controlled rate to a diaphragm 1292. When a sufficient pressure has been created against the diaphragm 1292, a valve member 1293 is moved to an open position. Thus it can be seen that the transition delay cartridge provides a delay. As soon as cartridge 1271 opens, gas is supplied from the outlet 1268 of the inspiratory cartridge 1263 to the inlet 1269 of the transition delay cartridge 1271 and gas is supplied to the outlet 1294. The gas then flows through an interruption interval pressure rise needle valve 1295 which is provided with a knob 1296 (also knob E) accessible on the front panel 1223 through an isolation check valve 1297 and then to the socket 1033 which is connected by a line 1034 to the combination venturi jet and exhalation valve assembly or phasitron 1036. Thus inspiratory flow is supplied to the patient at a rate controlled by the control knob 1296 of the needle valve 1295 to control the inspiratory flow.

At the same time that the gas is being supplied from the outlet 1294 to the interruption interval pressure rise needle valve assembly 1295, gas is also supplied from the outlet 1294 of the transition delay cartridge 1271 through an isolation check valve 1298 to an inspiratory time metering valve 1299 which is provided with a knob 1301 (also knob D) accessible from the front panel 1223 which is provided for regulating the inspiratory time. Gas flows from the inspiratory time metering valve 1299 into a phasing segment 1302 of the pneumatic circuitry. Gas flows from the phasing segment 1302 into the inspiratory reset needle valve assembly 1303 which is provided with a knob 1304 (also knob C) accessible on the front panel 1223.

Gas metered by the inspiratory reset needle valve assembly 1303 is supplied to the inlet 1306 of the inspiratory reset cartridge 1277. However, as explained before since a pressure is applied to the diaphragm 1278 the valve member 1279 is in a closed position and prevents the gas from being supplied from the inlet 1306 to the outlet 1307 which is vented to ambient. Since gas cannot escape to ambient through the outlet 1307, gas which is metered through the needle valve 1299 is supplied to the servo port 1259 of the inspiratory cartridge 1263 and gradually builds up a pressure against the diaphragm 1261 and moves the valve member 1262 after a predetermined pressure build up as determined by the adjustment of the needle valve 1299 to a closed position. As soon as the inspiratory cartridge 1263 is closed, gas no longer is supplied from the outlet 1268 through the base line pause oscillation check valve 1281 to the servo port 1282 of the interruption interval cartridge 1283. As soon as gas under pressure is no longer being delivered to the servo port 1282, gas behind the diaphragm 1284 will be bled out through the base line pause needle valve 1287 through the perforated ambient muffler 1273 to ambient. At the same time the gas behind the diaphragm 1278 of the inspiratory reset cartridge 1277 is bled down through the perforated ambient muffler 1283 to ambient. As soon as the valve member 1279 of the inspiratory reset cartridge 1277 opens, gas behind the diaphragm 1261 of the inspiratory cartridge 1263 will be bled out through the needle valve 1303 and through the inlet 1306 and the outlet 1307 of the inspiratory reset cartridge 1277 to ambient. The valve member 1262 of the inspiratory cartridge 1263 then moves to its normally open position to start a new cycle.

This cyclic operation will continue at a rate determined by the positioning of the knobs 1301 (knob D) and 1304 (knob C) to provide an operation which is very similar to the operation of a time cycled convection ventilator. A frequency up to approximately 40 cycles per minute can be obtained with this time cycled operation.

The operation of the high frequency diffusion ventilation portion of the ventilator 1201 shown in FIG. 26 may now be described. Let it be assumed that the master on/off switch 1221 is turned on. Gas is supplied from the outlet 1266 to the inlet 1311 of a normally open primary oscillator cartridge 1312. Gas flows through the cartridge 1312 through an outlet 1313 to the servo port 1314 of oscillator reset cartridge 1316. This gas forces the diaphragm 1317 to move a valve member 1318 to a closed position. Gas also flows from the outlet 1313 into the servo port 1319 of a normally open failsafe oscillator or counterpulse cartridge 1321. The gas operates upon a diaphragm 1322 to move a valve member 1323 to a closed position. At the same time gas is also supplied from the outlet 1313 to an adjustable frequency needle valve 1324 which is connected to the counter pulse socket 1077 on the front panel 1223. The valve 1324 is provided with a knob 1326 (also knob A) accessible on the front panel 1223. If the knob 1326 is rotated to close needle valve 1324, oscillation will gradually decrease until it ceases. If the knob 1326 is rotated to open the needle valve 1324 gas will be drained more rapidly into the counterpulse socket 1077 and into line 1078 to cause a higher frequency of oscillation. Gas is also supplied from the outlet 1313 of the primary oscillator cartridge 1312 to a servo port 327 of a chopper frequency counter 1328. Gas supplied to the port 1327 operates upon the diaphragm 1329 which carries an L-shaped chopper flag 1331 which oscillates in accordance with the pressure pulses applied to the diaphragm 1329. The chopper flag 1329 forms a part of a conventional infrared frequency counter (not shown) which has an output display 1332 on the panel 1223. The counter is provided with a push to start button 1333 to display the frequency being measured. The counter is provided with its own self contained battery.

Gas is also supplied from the servo port 1317 of the primary oscillator cartridge 1312 through its outlet 1313 to a timing circuit which includes a primary oscillator isolation check valve 1337 and a normally open needle valve 1338. Means is provided for adjusting the needle valve 1338 and consists of an Allen head screw 1341 mounted on the front panel 1323 and identified as the E of the I/E ratio. When valve 1338 is wide open, gas flows through it very rapidly through the outlet 1339 into the phasing segment up to the inlet 1340 of the normally closed oscillator reset cartridge 1316. Since the valve 1318 of cartridge 1316, is closed, the gas has no where to flow but into the servo port 1342 of the primary oscillator cartridge 1312 and acts upon the diaphragm 1343 to move the valve member 1344 to a closed position. Movement of the valve member 1344 to the closed position occurs very rapidly to shut off the flow of gas through the outlet 1313 of the primary oscillator cartridge 1312.

In order to increase the time for close down of the primary oscillator cartridge or in other words increase the inspiratory time, it is merely necessary to adjust the needle valve 1338 on the front panel 1223 to a more closed position until the desired close down rate has been achieved. This adjustment of the valve 1338 changes the I/E ratio. This needle valve 1338 in effect provides a timing circuit for running of the counterpulse which is supplied to the socket 1077. If it is desired to shorten the time of the counterpulse, the valve 1338 is moved toward the open position.

The frequency rate of the counterpulse is controlled by the needle valve 1324 which is provided with a control knob 1326 (knob A) on the front panel 1223. The more that the valve 1324 is opened up, the faster the gas is bled down from the servo port 1317 of the oscillator reset cartridge 1316.

The area behind the diaphragm 1317 of the oscillator reset cartridge 1316 is bled down through a needle valve assembly 1348 which is provided with an Allen head adjustment 1349 on the front panel. The adjustment screw 1349 is identified as the I of the I/E ratio. After flowing through the valve assembly 1348, gas flows to the counterpulsing socket 1077 through the frequency valve 1324. By closing the valve assembly 1348, the frequency can be decreased to a rate of approximately 700 times a minute. By opening the needle valve 1348, the frequency can be readily increased, for example, to a rate up to 1,500 times a minute.

In the description of the operation of the ventilator 1201 shown in FIG. 26 thus far described, it can be seen that the frequency of the counterpulses can be varied without varying the amplitude and that the counterpulses are 180° out of phase from the pulses from the primary oscillator cartridge 1312. The amplitude of the counterpulses can be varied as hereinafter described.

When the master on/off switch 1222 is turned on, gas is supplied through an oscillatory CPAP/PEEP valve 1351 which is provided with a control knob 1352 (also knob B) on the front panel 1223. The needle valve 1351 meters gas through the normally open interruption interval cartridge 1283, then up through the normally open parallel oscillator cartridge 1321 which is being opened and closed by the timing circuit hereinbefore described 180° out of phase with or inverse to the opening and closing of the primary oscillator cartridge 1312.

The opening and closing of this timing circuit will determine the flow through the parallel oscillator cartridge 1321 which determines the flow of gas through the socket 1033 to the phasitron 1036. The amplitude or volume flow of the gases to the phasitron 1036 is controlled by the opening and closing of the needle valve 1351. The amplitude of the gases controlled by the valve 1351 (by knob B) is separated from the frequency controlled by the control knob 1326 (knob A). Thus it can be seen that there has been provided a timing circuit that provides a counterpulse or a subambient phase potential which also opens and closes the parallel oscillator cartridge 1321 that controls the primary flow to the phasitron socket 1033.

The interruption interval cartridge 1283 opens and closes every time the time cycled parallel oscillator cartridge 1321 opens and closes. Every time interruption interval cartridge 1283 closes gas cannot flow from the master on/off switch through the oscillatory CPAP/PEEP needle valve 1351 which controls the flow to the parallel oscillator cartridge 1321. When this flow is stopped, the counterpulses hereinbefore described are still provided to the swivel tee 1421 to provide diffusion. Thus there is provided a small amount of flow to the patient coming through the swivel tee 1421. This gas flow is not being supplied from the main gas flow from the socket 1033 to the venturi jet of the phasitron 1036. Thus it can be seen that a controllable diffusive ventilation system has been provided in the present ventilator in addition to the conventional convection ventilation system hereinbefore described. In order to provide this diffusive ventilation in the ventilator, the principal addition to the pneumatic circuitry, has been the parallel oscillator cartridge 1321.

The demand CPAP regulator 1217 is provided with a diaphragm 1356 which has a fixed spring 1357 which urges the valve member 1358 carried by the diaphragm 1356 to an open position and an adjustable spring 1359 which moves the valve member 1358 towards a closed position. The force applied to the adjustable spring 1359 is adjusted by a knob 1361. The demand CPAP regulator 1217 is provided with a servo port 1362 which is connected to the proximal airway monitor 1089 and is connected to the gauge socket 1087 on the front panel 1223 that is connected to the combination venturi jet and exhalation valve assembly 1036. The cartridge 1217 is also provided with an outlet 1363 which is connected to a CPAP isolation check valve 1364 that is connected to the phasitron socket 1033 on the front panel 1223. Thus it can be seen that the regulator 1217 will supply gas under demand to the airway of the patient when the gas pressure in the proximal airway of the patient drops below a predetermined value. The diaphragm 1356 of the cartridge 1217 always sees the proximal airway pressure. The adjustable spring 1359 can be adjusted by use of the knob 1361 to provide a predetermined airway pressure, as for example, five centimeters of water pressure before the valve member 1358 is moved to a closed position. Thus the cartridge 1217 will only move to a closed position when five centimeters of pressure is established in the patient airway. If the proximal airway pressure is reduced below this valve, the cartridge 1217 will open and provide an accelerating flow of gas. Thus for example, the patient by suction could cause the pressure to drop in the pressure airway to cause the operation of the demand CPAP cartridge 1217 thereby giving it its name. As explained previously, the demand output from the CPAP regulator 1217 is supplied through the isolation check valve 1364 to the phasitron socket 1033 which is connected to the combination venturi jet and exhalation valve assembly 1036. The demand CPAP regulator 1217 acting in conjunction with the combination venturi jet and exhalation valve assembly 1036 works well because the combination venturi jet and exhalation valve assembly 1036 acts as a pressure dampening governor.

Now let it be assumed that there has been an airway disconnect between the ventilator 1201 and the patient. As soon as this occurs, the demand CPAP regulator 1217 will sense this occurrence and will open to supply gas to the phasitron socket 1033. As the flow of the gas accelerates, there will be a pressure build up in the lines supplied to connect to the socket 1033 which are connected through the normally open failsafe cartridge 1242 to the audible and visual alarms 1248 and 1249.

In order to prevent an overpressure condition from occurring, an accessory pressure limiting regulator 1366 has been provided which is connected to the phasitron socket 1033. By way of example, this regulator 1366 can be adjusted to a suitable pressure as for example, a pressure of 16 psi which translates to approximately 90 centimeters of water pressure. When this pressure is reached, the regulator 1366 will vent to ambient through outlet 1367. The regulator 1366 is provided with a control knob 1368 accessible on the front panel 1211 for adjusting the pressure. This prevents a pressure above this predetermined pressure being established in the airway of the patient or even in the ventilator itself. So even if everything else fails in the ventilator, this would be the maximum peak pressure which could be provided by the ventilator.

An accessory socket 1371 is provided on the front panel 1211 and is connected to source gas. The rate of flow of gas through the accessory socket 1371 is controlled by a needle valve having a knob 1372 (knob J) on the front panel 1211.

The monitor module module 1284 which also can be characterized as a waveform analyzer is provided with a front panel 1381. It also includes an oscilloscope screen 1382 which is mounted in the front panel. The front panel also carries a sensitivity knob 1383 calibrated for full scale deflection in millimeters of $H_2O$, a sweep speed knob 1384 calibrated in millimeters per second, a power off-on switch 1386, a freeze on-off switch 1387 and an alarm reset push button 1388. The electronics provided within the monitor 1204 are substantially conventional and will not be described.

The monitor module 1204 senses the pressure in the proximal airway of the patient and places a trace on the screen 1382. The control knobs provided on the monitor make it possible to control the sensitivity and the sweep speed. By way of example, if a patient utilizing the ventilator has provided a good blood gas study and with the waveform on the screen 1382 properly calibrated, the waveform can be frozen. A wax pencil is then used to draw onto the screen 1382 over the frozen waveform so that a pencil tracing appears on the screen representing this waveform. This provides a pattern which can be compared by a nurse or other person monitoring the activities of the patient with the waveform appearing on the screen. If the waveform deviates from the pattern that has been traced on the screen, adjustments can be made on the ventilator 1201 to provide the desired pattern again. These features make it possible to monitor the operation of the ventilator on the patient in a very precise manner.

The ventilator 1201 includes a breathing circuit 1391. A block 1392 is secured to the handle 1011 of the accessory module 1203. A ring mount 1393 is secured to the block 1392 and carries a nebulizer 1394. A breathing harness 1396 is provided for connecting the nebulizer 1394 into the ventilator module 1302 and to the breathing circuit 1391.

Figure 27:
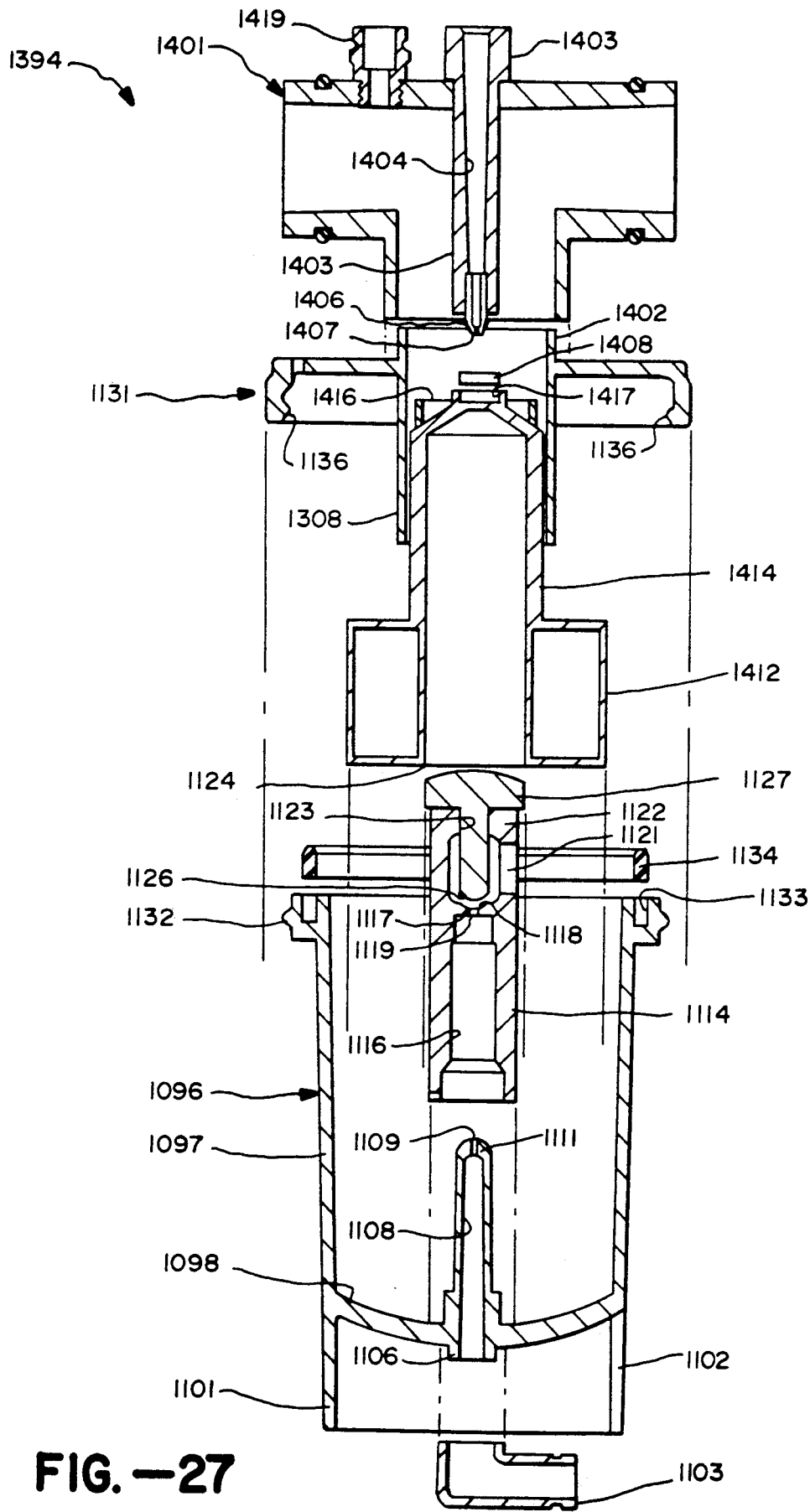
FIG. 27 is a cross sectional exploded view of the nebulizer utilized in the ventilator in FIG. 25.

The nebulizer 1394 as shown in FIG. 27 is very similar 0 in certain respects to the nebulizer 1029 shown in FIGS. 20 and 21. FIG. 27 shows an exploded view of the nebulizer 1394. The nebulizer 1394 is provided with features which make possible long term nebulization rather than the short term nebulization that can be provided by the nebulizer 1029 without the necessity for refilling. The nebulizer 1394 has many parts which are similar to the nebulizer 1029. Thus the cup-like member 1096 can be substantially identical as can be seen from FIGS. 20, 21 and 27. The nebulizer 1394 also includes a quick disconnect cap 1131 of the type described in connection with the nebulizer 1029. It also includes a tee 1401 which is bonded to an upwardly extending protrusion 1402 provided on the cap 1131 by a suitable means such as ultrasonic bonding. A bayonet or stamem 1403 is mounted in the tee 1401 and is mounted in such a way that it extends through the tee and extends downwardly into the sleeve 1138 provided as a part of the cap 1131. A fitting 1406 of a suitable material such as stainless steel is mounted on the lower extremity of the bayonet or stamem 1403 and is provided with an orifice 1407 of a suitable size, as for example, 0.013 of an inch. The fitting 1406 carrying an orifice 1407 serves as the stationary part of a valve assembly. The orifice 1407 is adapted to be engaged by a pad 1408 formed of a suitable flexible material such as Silastic which serves as a valve member of the valve assembly. The pad 1408 is carried by a float assembly 1409. The float assembly 1409 consists of a sealed annular float chamber 1411 formed of an annulus 1412 disposed on the lower portion of the float assembly 1409. The float assembly 1409 is provided with a centrally disposed passage 1413 of such a size so that the float assembly can ride up and down over the cap 1127 and the sleeve 1114.

A suitable number of upstanding posts 1414, as for example, three, spaced 120° apart, are provided on the annulus 1412. The upper extremities of the posts 1414 are provided with inclined portions 1414a and carry a cylindrical portion 1416 which is provided with a cylindrical recess 1417 that receives the pad 1408.

The bayonet or stamem 1403 can be connected to a standard intravenous set to supply liquid as desired to the nebulizer for humidifying the gases. This supply is shown as a refill source 1418 in FIG. 26. The flow of the liquid into the nebulizer is controlled by the float assembly 1409. When there is approximately 20 cc's of liquid in the nebulizer, the float assembly 1409 is raised into a position so that the pad 1408 serving as a valve member engages the orifice 1407 and occludes the same to prevent further liquid entering the nebulizer. As the nebulizer is used and the liquid level drops, the float assembly 1409 will drop permitting additional liquid to be supplied to the nebulizer. Thus it can be seen that automatic nebulization can be provided for the patient over lengthy periods of time.

In order to permit drugs and other liquids to be introduced into the nebulizer, a drug injection fitting 1419 has been provided on the tee 1401. The drug injection fitting 1419 can be capped when not in use. For example, during use of the apparatus by a patient, epinephrine can be introduced through the fitting 1418 and into the liquid in the nebulizer.

Figure 28:
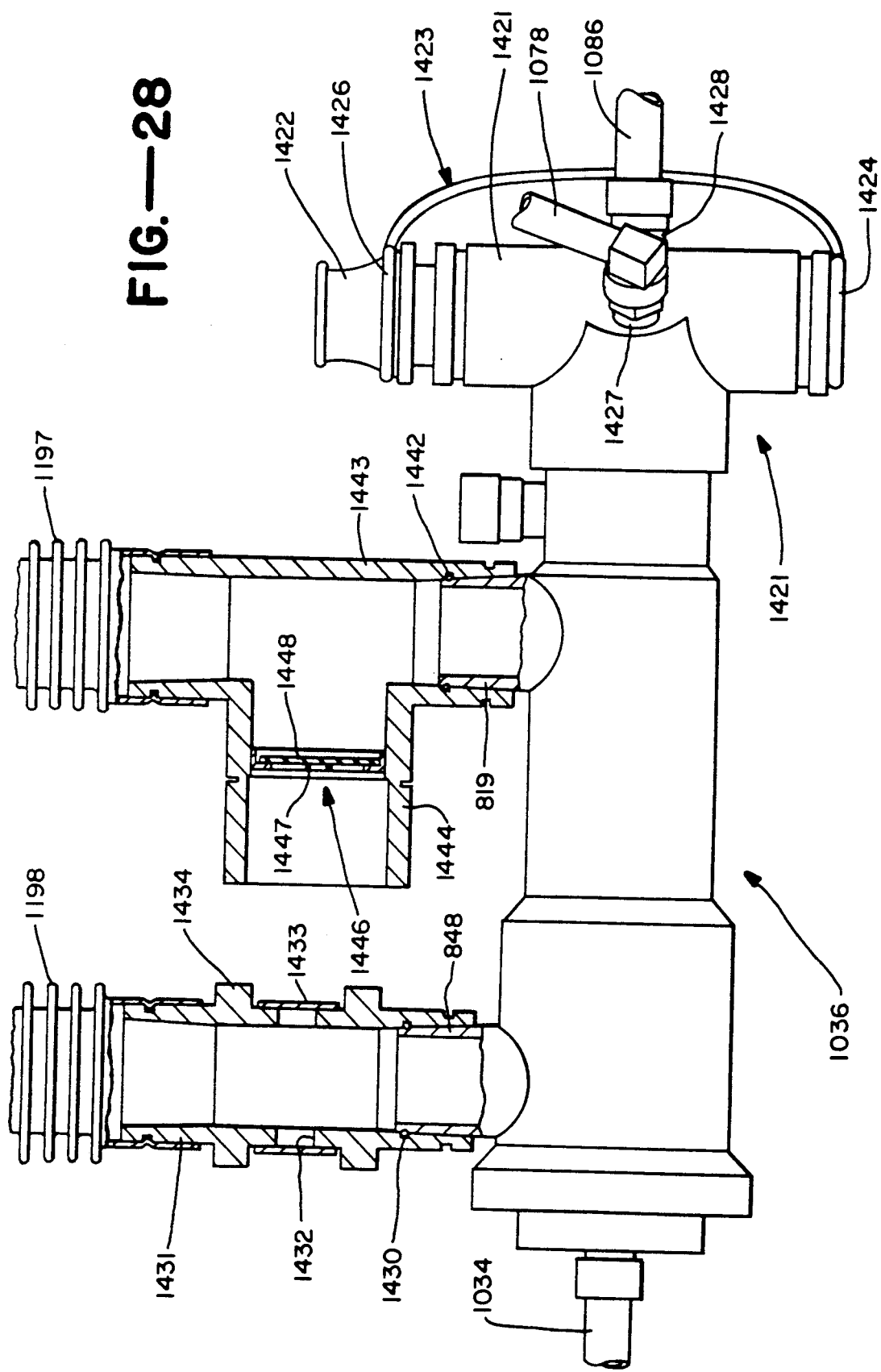
FIG. 28 is a cross sectional view of the combination venturi jet and exhalation valve assembly used in the ventilator in FIG. 25.

The breathing circuit 1391 as shown in FIG. 28 includes a combination venturi jet and exhalation valve assembly 1036 of the type hereinbefore described. A swivel tee 1421 is mounted on the assembly 1036. One leg of the tee 1421 is provided with a suitable patient adapter such as a mouthpiece 1422. The other leg of the tee 1421 has a retainer 1423 carried thereby. The retainer consists of a plug 1424 which is fitted into one leg of the tee and the other end carries a ring 1426 which is adapted to be secured to the patient adapter to hold it in place. A pair of fittings 1427 and 1428 are mounted in the tee 1421. The fitting 1427 is connected to the tube 1078 which is connected to the remote socket 1077 provided on the front panel 1223 and fitting 1428 is connected to the tube 1086 which is connected to the gauge socket 1087.

In the present application, the combination venturi jet and exhalation valve assembly 1036 also called a phasitron serves a number of purposes. It serves as an amplifier because it amplifies the stroke volume by entrainment of additional gases with pneumatic clutching. It also provides an exhalation valve. The phasitron 1036 is supplied with gas from the tube 1034 which is supplied from the socket 1033. The phasitron 1036 is provided with an inlet or entrainment port 848 which is used for entraining additional gases as the gas is introduced into the venturi jet from the tube 1034.

As shown in FIG. 28, the phasitron 1036 which is the phasitron shown in FIG. 10 is connected to a corrugated flexible inhalation tube 1198 which is connected by a coupling 1431 to the inlet port 848. An O-ring 1430 forms an air tight seal between the coupling 1431 and the inlet port 848. The coupling 1431 is provided with a plurality of circumferentially spaced oval-shaped holes 1432. By way of example, four such holes can be provided spaced 90° apart. A flexible sleeve 1433 formed of a suitable elastomeric material covers the holes 1432 and is disposed between spaced-apart annular flanges 1434 formed as a part of the coupling 1431.

Let it be assumed that for some reason that the ventilator 1201 becomes locked in the inspiratory phase with the exhalation valve remaining in the closed position. When this occurs, there will be a pressure build up within the phasitron 1036 and the venturi jet will no longer entrain gases. This increased gas pressure will pass through the openings 1432 and inflate the elastomeric sleeve 1433 which serves as a barrel valve and permits the excess pressure to flow to ambient. Thus it can be seen that the sleeve 1433 serves as an inspiratory fail safe valve.

The large breathing tube 1198 is connected through the water trap 1199 of a conventional type to the tee 1401 of the nebulizer 1394. The tee 1401 of the nebulizer is connected to a volume regulation manifold in the form of a cross 1436 as shown in FIG. 29. One leg 1437 of the cross 1436 is provided with an inspiratory check valve assembly 1438 which only permits gas flow into the tee 1401 of the nebulizer and prevents reverse flow. This check valve assembly includes a spider 1439 and a flapper valve 1441. Any undue pressure buildup in the large breathing tube 1198 will be relieved through the barrel-type valve provided by the sleeve 1433 as hereinbefore explained.

When the patient exhales, the exhaled gases will be discharged through the outlet port 819 into a swivel tee 1443 as shown in FIG. 28 which is mounted on the outlet 819. An O-ring 1442 provides an air-tight seal. The swivel tee 1443 is provided with a leg 1444 which has a check valve assembly 1446 mounted therein. The check valve assembly consists of a spider 1447 and a flapper valve 1448. The valve assembly 1446 serves as an expiratory valve safety governor. It will admit ambient air. Thus, for example, if for some reason the ventilator was turned off and no air was being supplied to the patient, the patient would still be able to breathe through the valve assembly 1446. Normally during the flow of exhalation gases through the tube 1197, the flapper valve 1448 will be in a closed position so that the exhaled gases from the patient will travel down the tube 1197 to the cross 1436 where it is connected to a leg 1451 of the cross as shown in FIG. 29. A valve assembly 1452 is provided in the leg 1451 and consists of a spider 1453 and a flapper valve 1454. The spider 1453 and flapper valve 1454 are arranged in such a manner that exhaust gases can only flow inwardly into the cross 1436 from the large breathing tube 1197 and not into the breathing tube from the cross. Gas passing into the cross 1436 from the tube 1197 will pass downwardly through a leg 1456 of the cross into the elastomeric bag 1196. As soon as the bag 1196 becomes overfilled, the additional exhaust gases will be discharged through the ambient purge port provided by another leg 1457 of the cross 1436 through a valve assembly 1458 consisting of a spider 1459 and a flapper valve 1461.

As hereinbefore explained, the bag 1196 is provided to provide additional inspiratory gases during peak inspiration. Rather than starving the patient during entrainment, gas will be pulled through the valve assembly 1452 into the large breathing tube 1197. By the provision of such a reservoir by use of the bag 1196, there is a partial rebreathing of exhaled gases. By providing such a reservoir, it is possible to ventilate at rates up to 30 to 50 liters a minute.

An exploded view of the failsafe governor alert 1248 is shown in FIG. 30. As shown therein it consists of a body 1466 formed of a suitable plastic. The body is provided with a cylindrical portion 1467 which adjoins a truncated conical portion 1468. An inlet 1469 is formed integral with the tapered or conical portion 1468 and is provided with an inlet flow passage 1471 which opens through the inlet 1469 and into a chamber 1472 within the cylindrical portion 1467. The body 1466 is also provided with an upwardly extending rim 1473. The rim 1473 is provided with a cylindrical recess 1474 which opens into the chamber 1472. A plurality of threads 1476 are provided on the outer surface of the cylindrical portion 1467 so that the governor alert 1248 can be threaded into the front panel 1211. A gate valve 1477 formed of a suitable material such as Teflon is provided and is adapted to seat against the interior of the conical portion 1468. The gate valve 1477 is provided with an inclined or tapered surface 1478 which generally corresponds to the incline of the conical portion 1468 which serves as a valve seat against which the gate valve 1477 can seat. A generally semi-spherical depression or recess 1479 is formed in the surface of the gate valve 1477 facing away from the inlet passage 1471. A valve stem 1481 also having a semi-spherical rounded end is adapted to seat in the depression or recess 1479 and extends outwardly from the gate valve 1477.

Means is provided for isolating the valve stem 1481 from the gate valve 1477 and consists of a pair of o-rings 1482 formed of a relatively soft rubber as for example, rubber having a hardness of approximately 40 durometers. The o-rings 1482 frictionally engage the valve stem 1481 and are placed one above the other and are adapted to engage the outer surface of the gate valve 1477 in such a manner so as to retain the lower extremity of the valve stem 1481 out of engagement with the depression or recess 1479 but still permitting the gate valve 1477 to pivot with respect to the valve stem. Means is provided for yieldably urging the valve stem into the depression or recess 1479 of the gate valve and consists of a spring 1483 concentrically mounted on the valve stem and having one end engaging a washer 1484 overlying the o-rings 1482 and having the other end adapted to be engaged by a nut 1486. The nut 1486 is threaded into a central portion 1487 of a spider 1488. The spider 1488 is mounted in the recess 1474 and retained therein by a clamping ring 1489.

The failsafe governor alert valve assembly 1248 serves two functions. It serves to provide a pressure relief above a predetermined pressure that is determined by the setting of the nut 1488 and its engagement with the spring 1483. It vents to atmosphere whenever the gas pressure against the gate valve 1477 exceeds the pressure which is sufficient to overcome the force of the spring 1483. At the same time the valve assembly 1248 is constructed in such a manner so that as when gas is being relieved under pressure through the valve assembly 1248 an audible alarm is provided by the periodic chatter of the gate valve 1477 on its seat. This chatter has been found to be particularly reliable and audible because of the fact that the gate valve 1477 has been isolated from the valve stem 1481. The valve assembly has been made particularly efficacious because of the isolation of the valve stem 1483 from the gate valve 1477 by the use of the two O-rings 1432. The audible signal given off by the alarm is very distinguishable. The outer clamping ring 49 provided serves as an amplifier to increase the intensity of the alarm. In addition, the clamping ring 49 physically protects the valve stem 1481.

Another embodiment of a breathing head assembly is shown in FIG. 31 and is one which is utilized for providing differential ventilation. This breathing head assembly 1501 consists of two separate combination venturi jet and exhalation valve assemblies or phasitrons 1036 which are coupled together with two tee assemblies 1502 and 1503. The tee assembly 1502 is connected to the inlet fittings 848 of the phasitrons 1036 whereas the tee assembly 1503 is connected to the exhalation outlets 819 of the phasitrons 1036.

The tee assembly 1502 is similar to the coupling 1431 provided in FIG. 28. The tee assembly 1502 includes a tee 1504. The tee 1504 is provided with legs 1506, 1507 and 1508. The legs 1506 and 1507 are provided with o-rings 1509 seated within annular recesses 1511 provided in the legs. These o-rings 1509 are adapted to frictionally engage and seat in annular recesses 1512 provided on the exterior surfaces of the inlets 848 on the phasitrons 1036. In this way, fluid-tight connections are made between the inlets 848 and the tee 1504.

The tee 1504 is also provided with a fitting 1513 which is adapted to receive a cap (not shown) which may be removed to introduce drugs and the like into the breathing circuit. The remaining leg 1508 of the tee 1504 is adapted to receive one end of a coupling 1516. The coupling 1516 is similar to the coupling 1431 shown in FIG. 28. The coupling is provided with an annular recess 1518 in one end which carries an o-ring 1517. The o-ring is adapted to snap into a recess 1519 provided on the leg 1508. The coupling is provided with a pair of spaced apart parallel annular flanges 1521. The coupling is also provided with a plurality of oval-shaped openings 1522 which are spaced circumferentially around the coupling. An elastomeric sleeve valve 1523 is carried by the coupling 1522 and is disposed between the flanges 1521. The other end of the coupling 1516 is connected to the large breathing tube 1198. The inlet fittings 866 of the phasitron 1036 are connected to the tubes or lines 1034 and 1078 which are connected respectively to the sockets 1033 and 1077.

The tee assembly 1503 is constructed of a tee 1526 having legs 1527, 1528 and 1529. The legs 1527 and 1528 are provided with o-rings 1531 seated in annular recesses 1532. The o-rings 1531 are adapted to friction and seat in recesses 1533 provided on the outlet fittings 819 of the phasitrons 1036 and form fluid-tight connections therewith. The leg 1529 is provided with an annular recess 1534 on the interior surface thereof. Another tee 1536 is provided having legs 1537, 1538 and 1539. An o-ring 1541 is mounted in an annular recess 1542 in the outer surface of the leg 1537. The o-ring 1541 is adapted to seat in the annular recess 1534 provided in the leg 1529 of the tee 1526. The other leg 1538 is adapted to receive the large exhalation hose 1197. A flapper valve 1543 is provided in the leg 1539 and is retained in position by a spider 1544 supported in the tee 1539 by a retainer ring 1546. The gauge tube 1086 which is connected to the socket 1087 is connected to the fitting 821 provided on one of the phasitrons 1036.

From the foregoing it can be seen that the inlets of the two phasitrons 1036 have been interconnected by a tee to interconnect the inspiratory failsafe valves. Essentially the same thing has been done on the expiratory side where the expiratory failsafe ports of the phasitrons 1036 have been interconnected.

The dual phasitron assembly 1501 shown in FIG. 31 has numerous applications where it is desired to utilize differential ventilation. Let it be assumed, for example, that a patient has a good lung and a bad lung, as for example, from a car accident in which a steering wheel injured one lung and the other lung was satisfactory. When such is the case it is desired to ventilate the damaged lung and to do very little, if anything, for the other lung. When this is the case, the line 1034 which is connected to the phasitron 1036, is connected to the inlet 866 of the phasitron 1036 which is to be connected to the damaged lung. A counterpulsing line 1078 can be connected to the other inlet 866 of the other phasitron 1036. The good lung would be connected to the phasitron 1036 which has the normal phasitron line 1034 connected thereto. The damaged lung, on the other hand, would be connected to the phasitron having the counterpulsing line 1078 connected thereto.

By use of the controls of the ventilator as hereinbefore described and by adjusting the IE ratio it is possible to control the damaged lung with both a frequency rate and a desired IE ratio. The damaged lung can be treated until it stabilizes while providing normal ventilation for the other lung.

Another advantage of such a breathing head is that it makes it possible for a surgeon to operate on one lung and to still ventilate the other lung. Also with respect to the lung on which the physician is operating, he does not want that lung to collapse. The present breathing head would make is possible to pulse a lung and keep the lung inflated and aerated at any desired level while the surgeon was operating on the same, as for example, excising a segment of the lung.

Operation of the ventilator shown in FIGS. 25 through 31 may now be briefly reviewed as follows. The ventilator 1201 as hereinbefore described is a ventilator which can provide conventional ventilation through conventional time cycling and which also can provide diffusive ventilation using convection. With these two basic types of ventilation being provided, the ventilator 1201 also has many other features. For example, it is provided with a demand CPAP and it is provided with a manual override. In addition, nebulization is also provided.

The expiratory failsafe exhalation valve assembly 1446 mounted on the combination venturi jet and exhalation valve assembly 1036 is in relatively close to the proximal airway so there is very little dead space. This is particularly important in protecting against a gas source failure. When a gas source failure would occur, the patient would first empty the reservoir bag 1196 and as soon as this gas has been exhausted, the expiratory failsafe valve opens to continue to permit the patient to breathe by bringing in ambient air. Thus by providing this expiratory failsafe valve 1446, protection has been provided against inspiratory failure, expiratory failure and a gas source failure.

Another safety feature provided in the ventilator is the use of the elastomeric safety loop formed by the retainer 1423 which serves to prevent disconnects between the patient adapter 1422 which can be in the form of a mouthpiece or endotracheal tube and the swivel tee 1421 which is connected to the combination venturi jet and exhalation valve assembly 1036. In addition, the plug 1424 of the retainer 1423 can be removed from the tee 1421 and the opening used. This opening can be utilized in conjunction with a bronchial scope. Also other tools can be introduced through the opening, as for example, tools for excising tissue while at the same time providing ventilation to the patient.

As hereinbefore explained, the counterpulsing flow which is provided in the ventilator provides a pulsive flow which is 180° out of phase with the flow provided by the timing circuit. The flows of gases from the counterpulsing circuit and the timing circuit pass through a large orifice at the top of the swivel tee 1421 and through the physiological airway port of the phasitron. The entrance of gas through this fitting dumps fresh gas into the combination venturi jet and exhalation valve assembly 1036. It also washes out any rebreathing gases. As also hereinbefore explained, the counterpulsing circuit makes it possible to provide differential ventilation for the two lungs of a patient.

Upon operation of the counterpulse cartridge 1321 a subambient pulse is delivered to the counterpulse socket 1077 which is delivered to the swivel tee 1421 carried by the combination venturi jet and exhalation valve assembly 1036. In order to increase the effectiveness of the subambient pulse, a venturi body may be provided. It is mounted into the assembly 1036 to provide a powerful suction apparatus by providing a pressure of $-30$ to $-40$ centimeters of water in the patient airway. The venturi body by narrowing the passage provides more effective venturi with greater velocity. This feature is particularly useful with small babies and with small animals to overcome resistance and draw air out of the lungs. The subambient pressure provides a washout so as to limit rebreathing of gases.

In FIGS. 32, 33 and 34 there are shown clinical waveforms which have been obtained utilizing the ventilator shown in FIGS. 25 through 30. As noted, the waveforms have been plotted in seconds and centimeters of $H_2O$.

The curve 1551 in FIG. 32 shows a diffusive ambulatory pattern which starts at a baseline of zero and is provided with a plurality of peaks 1552 which show oscillation which gradually increases in centimeters of $H_2O$ until pneumatic clutching occurs which causes the pressure rise to level off as shown in the curved portion 1551. This pneumatic clutching occurs at a predetermined value of centimeters of $H_2O$, for example, between 10 and 15 psi. A variable frequency is provided with an independent variable IE and with the amplitude controlled by a knob 1352 (knob B). The frequency is controlled by knob 1326 (knob A). By examining FIG. 32, it can be seen that the pneumatic clutching occurs at approximately the point where the amplitude reaches a maximum which on the curve would be approximately 12 centimeters of water. This maximum amplitude is determined by the setting of the knob 1352. If knob 1352 is rotated counterclockwise to open it up further, the amplitude is increased to higher values, as for example, to 30 or 40 centimeters of water. Typical settings of the knob 1352 for neonates, would range from 15 to 20 psi, for pediatrics 20 to 25 psi, for adults 20 to 35 psi and for giants 35 to 40 psi. The frequency 1326 is set to the appropriate frequency. The IE ratio is also set at an appropriate value, typically it can be one-to-one. To obtain percussion, it can range from 1:2 to 1:3.

As shown in FIG. 2, the oscillations can continue for a suitable period of time, as for example, approximately 15 seconds. At this time, the transition delay cartridge 1271 takes over in the manner hereinbefore described so that pressure in the patient airway drops down to near the baseline as shown by the portion of the curve 1551$b$ in FIG. 32. This baseline is established by the demand CPAP regulator 1217 under the control of knob 1351. The demand CPAP can be turned off in which case the baseline is at ambient or zero centimeters of water as shown by the curve in FIG. 32. However, it should be appreciated that, if desired, the baseline can be set at any desired value, as for example 5 or 6 centimeters of $H_2O$.

The conventional ventilator is then programmed for an inspiratory time which is determined by the adjustment of the knob 1301 (knob D) and by the inspiratory flow by the adjustment of the knob 1296 (knob E) which will determine the pressure rise as a conventional tidal volume is delivered into the lungs of the patient. After the tidal volume is delivered to the patient's lungs, the pressure drops to the baseline and a pause can be introduced by adjustment of the knob 1288 (knob F). This pause can range from various periods of time, as for example, from 1 second to 4 or 5 seconds typically in the range of approximately two seconds. The length of the pause determines the time that is permitted for blood to be returned into the pulmonary circuit by the patient's heart.

In the curve 1551 shown in FIG. 32 there is a convective drop to the baseline as represented by the portion 1551$b$ of the curve 1551, a convective rise to the maximum pressure as shown by the portion 1551$c$ and thereafter a convective drop back to the baseline represented by the portion 1551$d$ of the curve 1551. Thereafter, there is a portion 1551$e$ of the curve 1551 during which counterpulses are being introduced which greatly enhance diffusion within the lung. As shown in FIG. 2, this waveform is then repeated as the ventilator continues to operate.

The waveform pattern which is shown in FIG. 32 is a typical pattern which could be utilized on neonates, pediatrics and adults where a respiratory distress syndrome is present. This is the unique situation where the lung is damaged or incomplete caused by accidental trauma, infection or by the undeveloped nature of a premature baby's lungs. This waveform shown in FIG. 32 represents a combination of diffusive and convective ventilation. In the portion 1551a of the curve 1551 there is high frequency diffusive ventilation at the rate of 300 to 600 oscillations a minute after which convective ventilation takes place and drops the pressure back down to the baseline permitting the patient to exhale to move the gases out of the lungs of the patient after which the lung is filled up again with a constant flow of gas to provide a conventional tidal volume to the patient with a counterpulse on it which helps to provide additional diffusion. After which this tidal volume is released from the lung as shown by the portion 1551d of the curve. Thereafter, the curve is repeated by high frequency diffusive ventilation followed by convective ventilation and this is repeated. By this combination of diffusive and convective ventilation, it can be seen that during the diffusive ventilation, the gases are mixed up in the lung by the high frequency ventilation after which these gases are dumped out of the lung in portion 1551b and thereafter the lung is rapidly refilled with a tidal volume and then emptied again and then held in a pause for a period of time to permit the blood to come back into the lungs.

In FIG. 33 there is shown a pattern which could be utilized with a patient having obstructive pulmonary disease. In such a case, it is important to obtain good mixing of the gases. In this situation, the convective or conventional ventilator is utilized to produce a pause only. A tidal volume is not delivered. The frequency is selected by adjustment of the knob 1326 (knob A) and the knob 1352 (knob B) is adjusted to provide a high amplitude. Thus as shown in the curve 1556 in FIG. 33 as soon as the respirator cycles on, it begins to oscillate and the amplitude increases rapidly until pneumatic clutching is achieved at the pressure set by the knob 1352 and is represented by the portion of the curve 1556a. In the portion of the curve 1556a, gas is delivered in increments to the patient preventing the gas from flowing in and out during the time that the amplitude is being increased. The portion 1556a of the curve 1556 shows that there are pulses with a pressure rise and a pressure drop followed by a pressure rise and a pressure drop. Each time the pressure drops, the pressure is equilabrated in the lung. This provides a relatively smooth curve which is substantially in the form of a sign wave and provides excellent intrapulmonary distribution in the lungs of the patient. By providing such high frequency pulses of gases, it is possible for the ventilator to accommodate various types of lung problems, as for example, puncture wounds, pneumothorases, interstitial air leaks and the like. By such an approach, it is possible for the ventilator to compensate for massive air leaks in the lungs and still ventilate the lungs. Thereafter the pressure drops down to the baseline as represented by the portion 1556b of the curve 1556 after which there is a pause represented by the portion 1556c of the curve. Thereafter the same waveform is repeated. In FIG. 33 the knob 1352 was adjusted to gradually increase the flow rate to increase the amplitude up to approximately 35 centimeters of $H_2O$. As can be seen, the convection tidal volume delivered by the conventional ventilator portion of the ventilator has been removed and all that is provided is diffusive high frequency ventilation. Counterpulsing, however, is still present as can be seen by the small pulses superimposed on the waveform.

In FIG. 34 there is shown another waveform 1557 which has been particularly efficacious on neonates. As shown in FIG. 34 as the ventilator is turned on, high frequency oscillations are supplied to the lung of the patient as represented by the curve portion 1557a until the pneumatic clutching pressure is reached at approximately 10 centimeters of $H_2O$ at which time there is delivered a short tidal volume as represented by the curve portion 1557b after which there is a drop to the baseline as represented by the curve 1557c. After a pause as represented by the curve portion 1557d of a suitable period, as for example, two seconds, the waveform is repeated until the right hand side of the waveform shown in FIG. 34 at which time the knobs 1352 and 1326 are turned off so that all that remains is convective ventilation as is represented by the peaks 1557b. These peaks are controlled by the knobs 1301 (knob D) and knob 1296 (knob E).

The adjustments of the knobs on the ventilator have been provided such that when the knobs are in a 12:00 o'clock position, the ventilator will function in a normal manner. Thus if an operator is unsure or becomes confused as to the adjustment of the knobs, the ventilator can be operated in a safe manner by turning all the knobs to the 12:00 position.

Another embodiment of the sleeve check valve or flow obtunder shown in FIG. 19 is shown in FIGS. 35 and 6. This sleeve check valve 1561, which also can be called a flow obtunder, consists of a cylindrical body or housing 1562 which has disposed therein a stem 1563. The cylindrical housing 1562 is provided with a cylindrical recess 1564 which is in communication with a passageway 1566 extending through a cylindrical extension 1567. The extension 1567 is provided with circumferential ribs 1568 spaced longitudinally of the extension and which are adapted to frictionally engage flexible tubing of a suitable type such as plastic tubing which is pushed onto the extension 1567. The housing 1562 also is provided with an annular recess 1569 which adjoins a chamfer 1571 making a graduated transition between the annular recess 1569 and the cylindrical recess 1564.

The stem or body 1563 is provided with a radially extending flange 1572 which is adapted to be secured to the cylindrical 1562 by suitable means such as ultrasonic welding. The stem or body 1563 is also provided with cylindrical portions 1573 and 1574 which are adapted to seat within the cylindrical recess 1569 and within the cylindrical recess 1564 respectively. The stem or body 1563 is also provided with cylindrical lands 1576 and 1577 which are spaced longitudinally away from the flange 1572. For reasons hereinafter described, the land 1576 is of a slightly larger diameter than the land 1577. By way of example, the land 1576 can have a diameter of 0.215 inches and the land 1577 can have a diameter of 0.205 inches. The stem or body 1563 is provided with a radially extending lip 1578 on the outer extremity of the same. The stem or body 1563 is also provided with a cylindrical extension 1579 on the side opposite the side the lands 1576 and 1577 are disposed. The extension 1579 is provided with spaced apart annular ribs 1581 which are adapted to be engaged by a flexible hose or tube (not shown) pushed over the extension 1579. The extension 1579 is provided with a flow passage 1582 which extends longitudinally of the stem or body 1563 into the region of the lands 1576 and 1577. A cross hole 1583 is provided in the stem or body 1563 between the lands 1576 and 1577 which opens into a pair of arcuate recesses 1584 and 1586 extending circumferentially of the stem or body 1563. It can be seen that the recesses 1584 and 1586 are of such a length so that there remain raised portions or ribs 1587 (see FIG. 36) extending between the lands 1576 and 1577. The recesses 1584 and 1586 are formed so that the portion of the recess adjacent the land 1576 in cross section is in the form of a quarter circle 1584a and that the portion of the recess adjacent the land 1577 is in the form of an inclined plane 1584 which adjoins a vertical surface 1584c. The surface 1584c adjoins the circular portion 1584a.

An elastomeric sleeve 1589 is disposed on the stem or body 1563 and is formed of a suitable material such as rubber. It is sized in such a manner so that it makes a relatively tight fit with the land 1576 but is relatively loose with respect to the land 1577. The sleeve 1589 is prevented from being blown off of the stem or body 1563 by the circumferential lip or flange 1578 and is therefore captured.

Assuming that a gas is introduced into the passage 1582 from the extension 1579, the gas will flow inwardly of the passage 1582 and will exit through the cross holes 1583. The gas will take the path of least resistance and will flow over the inclined ramp surface 1584b and then out circumferentially around the sleeve 1589 and then the land 1577. Gas released by the sleeve will then pass out through the passage 1566 provided in the cylindrical body 1562. It is has been found that by constructing the sleeve check valve in this manner, fluttering or dancing of the sleeve 1589 at high frequencies in a range of 1500 to 2000 times a minute has been eliminated. This is made possible because the sleeve is captured by the land 1576 and is held stationary while leaving the other end of the sleeve to flex to permit the escape of the gas from the cross holes 1583. In order to prevent flaking off of the distal extremity of the sleeve 1589, it has been found that it is desirable to radius the inside distal extremity of the sleeve to provide a curved surface 1591. With such a construction it has been found that the sleeve check valve 1561 can operate under high frequency conditions for long periods of time.

In FIGS. 37 and 38, there is shown a normally open flow/timing cartridge 1601 which is particularly useful in the present invention. It consists of a manifold body 1602 and a cartridge body 1603. The manifold body 1602 is generally cylindrical as shown and is provided with a radially extending flange 1604 provided on one extremity thereof. The flange 1604 is provided with an annular recess 1605.

The manifold body 1602 is provided with three threaded bores 1606, 1607 and 1608 disposed circumferentially around the circumference of the body 1602 adjacent the rear extremity of the body 1602. As shown in the drawings, the bores 1606 and 1607 are spaced 180° apart with respect to each other whereas the bore 1608 is disposed between the bores 1606 and 1607 and is spaced 90° therefrom. The bores 1606 and 1607 are in communication with a flow passage 1609 extending diametrically of the body. The flow passage 1609 is in communication with a flow passage 1611 which can be identified as a first flow passage for the manifold body 1602. The flow passage 1611 extends at right angles to the flow passage 1609 and opens into a threaded bore 1612 provided in an externally threaded cylindrical extension 1613 provided on the rear extremity of the body 1602. Another flow passage 1614 is provided in the body 1602 and is in communication with the threaded bore 1612 and is in communication with the bore 1608. Fittings 1616 are provided in certain of the bores 1606, 1607 and 1608 and are adapted to be connected to flexible tubes of the type hereinbefore described.

The manifold body 1602 is also provided with another threaded bore 1617 extending radially of the body and spaced forwardly of the bores 1606 and 1607. It is also provided with a fitting 1616. The bore 1617 is in communication with a flow passage 1618 extending radially of the bore and is in communication with another flow passage 1619 extending perpendicular thereto and which opens through the forward extremity of the body 1602 into a dish-shaped recess 1621. The flow passage 1619 can be identified as a second flow passage for the manifold body 1602.

The cartridge body 1603 has a generally bell-shaped configuration. It is provided with a port or flow passage 1623 on its forward extremity which is axially aligned with the cartridge body and is in communication with a generally bell-shaped plenum chamber 1624 which opens through the rear of the cartridge body 1603. The flow passage 1623 can be identified as a first flow passage for the cartridge body 1603. The cartridge body is also provided with a side port 1626 mounted therein. The ports 1623 and 1626 are configured in such a manner so that quick disconnect fittings of the type hereinbefore described can be utilized in conjunction with the same.

A poppet valve assembly 1627 is disposed within the bell-shaped chamber 1624 and is engaged by the manifold body 1602 which is removably secured to the cartridge body 1603 by suitable means such as a C-type lock ring 1628 which engages the rear side of the flange 1604 of the manifold body 1602 and an annular inwardly extending lip 1629 provided at the rear extremity of the cartridge body 1603. The poppet valve assembly 1627 includes a circular diaphragm 1631 formed of a suitable material such as rubber which has a bead 1632 formed on its outer margin which is captured between the manifold body 1602 and the cartridge body 1603. As shown, this bead 1632 is disposed in the annular recess 1605 of the flange 1604 and seats against a shoulder 1633 of the cartridge body 1603. The shoulder 1633 is provided with a raised rounded lip 1634 which also serves to capture the bead 1632.

The diaphragm 1631 is provided with a curved semicircular portion 1636 which is relatively thin to permit flexing of the diaphragm. The diaphragm is also provided with a central circular thicker portion 1637 which is of a size so that it is adapted to fit within the dish-shaped recess 1621 of the manifold body 1602. The central portion 1637 is provided with a plurality, in this case, four cylindrical projections or feet 1638 which are uniformly spaced on the surface of the central portion 1637. The underside of the diaphragm 1631 is in communication with a flow passage 1619 of the manifold body 1602. At least a portion of the flow passage 1619 can be considered to be a second flow passage for the cartridge body 1603.

The central portion 1637 is also provided with a centrally disposed cylindrical protrusion 1639 on the side opposite on which the projections or feet 1638 are disposed. The centrally disposed protrusion 1639 serves as a seat for a cam button 1641 of a suitable material such as plastic. The cam button is provided with a recess 1642 which receives the protrusion 1639. It is also provided with a radially extending flange 1643 which terminates short of the semicircular portion 1636 of the diaphragm 1631. The cam button 1641 extends through a ring or washer 1644 formed of a suitable non-corrosive metal such as brass or stainless steel. The forward extremity of the cam button engages a disphragm seal 1646 formed of a suitable material such as rubber. The seal 1646 is provided with an outer annular bead 1647 which is captured between the washer 1644 and a shoulder 1648. The washer 1644 is held in place by a C-type lock ring 1649 which engages an annular recess 1650 provided in the cartridge body 1603.

An elastomeric percussion pad 1651 is disposed in the ring 1644 between the seal 1646 and the top of the cam button 1641 and has a diameter slightly greater than that of the cam button. This pad can be loaded with 15 to 20% graphite so as to provide a slippery permanent shock absorbing and compression absorbing interface between the cam button 641 and the disc 1646. Thus, the bottom surface of the seal 1646 is protected from abrasion by compression and stretching of the seal by movement of the cam button 1641.

A poppet or poppet valve plunger 1652 is provided which is seated over the disc 1646. The valve plunger or poppet 1652 is made of a suitable material such as a relatively hard plastic and is provided with a stem 1653. The stem 1653 is generally cylindrical in form and extends at right angles or forwardly from a radially extending flange or poppet head 1654. The flange 1654 is provided with a circular recess 1656 facing rearwardly and which has disposed therein a pad 1657. The pad 1657 is formed of a suitable elastomeric with a 15 to 20% loading of graphite.

The pad 1657 has a diameter greater than that of the cam button 1641 and serves to protect the seal 1646 from abrasion caused by compression and stretching of the diaphragm seal between the poppet head 1654 and the cam button 1641.

The valve plunger 1652 is provided with an annular recess 1658 on the upper extremity of the stem 1653 and has mounted therein an O-ring 1659. The O-ring 1659 is adapted to form a sealing engagement with an annular inclined valve seating surface 1661. Compression of the O-ring is limited by limiting the travel of the plunger 1652. The plunger 1652 cannot travel beyond the point where the head 1654 strikes the shoulder 1662. A pilot bore or chamber 1663 adjoins the valve seating surface 1661 and the plenum chamber 1624.

In the event that the diaphragm seal 1646 is breached, vent holes 1664 to ambient in the cartridge body 1603 are sufficient to limit the pressure rise caused by onservoing against the forward side of the master diaphragm 1631. These vent holes 1664 are sufficiently large to assure there is sufficient venting to negate any possible high temperature stall as the diaphragm becomes more pliant at high temperatures as well as potential hard open servoing.

The cartridge 1601 is provided with a needle valve assembly 1666 which is threaded into the bore 1612. It is provided with a control knob 1667 for adjusting the position of a needle valve 1668 to control the flow of gas from the passage 1611. The cartridge 1601 can be supported in a suitable manner such as by mounting it on a panel 1669 and securing it thereto by a nut 1671 as shown in FIG. 37.

Operation and use of the normally open flow/timing cartridge 1601 shown in FIGS. 37 and 38 may now be briefly described as follows. Let it be assumed that the cartridge 1601 is in its normally open position. In this position gas may flow from the port 1626 to the port 1623 or vice versa. Let it now be assumed that it is desired to interrupt this flow of gas from the port 1626 to the port 1623. This is accomplished by applying gas under pressure to the servo port 1617. This gas passes through the passages 1618 and 1619 to the underside of the diaphragm 1631 to cause it to rapidly move the poppet valve in the form of the O-ring 1659 into rapid engagement with the seat 1661 to prevent further flow of gases from the port 1626 to the port 1623.

Now let it be assumed that it is desired to move the cartridge 1601 from the closed position to its normally open position. To accomplish this, the pressure from behind the diaphragm 1631 is bled down gradually. As soon as there has been some bleed down, the poppet valve 1652 will have a tendency to open at least a slight amount. This permits the pressure of the gas which is in the port 1623 to act upon the very small area of the end of the poppet valve 1652, as for example, approximately one quarter of an inch in diameter and to act upon the diaphragm 1631 which because of its much larger area would cause the poppet valve to snap rapidly to a completely open position. Conversely when pressure is applied to the servo port 1606, the poppet valve 1652 is cammed rapidly into a closed position. This snap opening and closing of the poppet valve 1652 is created because of the large differential between the quarter of an inch diameter surface represented by the O-ring 1659 at the top of the poppet valve and the one-half inch diameter surface of the diaphragm. In other words by providing this large differential it is possible to obtain almost instantaneous opening and closing of the poppet valve. This rapid opening and closing makes possible very high frequency of operation of the cartridge.

The cartridge 1601 will work over a very wide range of operational pressures because the same operational pressure is used in the inlet port 1623 as in the servo port 1617. Thus, for example, it is possible to operate this type of cartridge with pressures ranging from 2 pounds to 100 pounds per square inch. As hereinafter explained, it is this capability of the cartridge which makes it possible to operate down to the neonatal range and up to an adult range and also makes it possible to provide a respirator which has a single control.

There are a number of features in the construction of the cartridge 1601 which makes this long life possible. As pointed out above, the poppet or valve plunger 1652 has been provided with an insert pad 1657 which is provided with graphite. This pad has a diameter which is slightly greater than that of the compression of the cam button. There is therefore provided a slippery permanent shock and compression absorbing interface between the cam button 1641 and the valve plunger 1652. This shock and compression absorbing interface also minimizes abrasion caused by compression and stretching of the diaphragm.

From the construction shown it can be seen that the poppet 1652 resides in a cylindrical chamber with a pilot bore 1663 rising from the inclined valve seat 1661. The pilot bore above the valve seat provides a centering effect for alignment purposes as the poppet stem 1653 carrying the O-ring 1659 moves towards the closed position. Gas flowing into the inlet port 1623 passes around the O-ring and causes centering alignment of the poppet assembly. Flow against the O-ring provides an opening piston effect against the poppet carrying the O-ring. The outlet port 1626 is disposed so that the gases exit around the stem and also cause the stem to be held in alignment within the conical valve seat limits.

This arrangement of the poppet assembly inhibits erratic functioning of the poppet valve. Adequate clearance is provided between the O-ring 1659 and the valve seat 1661. A definitive pressure drop across the O-ring 1659 which serves as a valve gate is maintained during all flow conditions to maintain full flutter-free opening as well as an opening servoing force. These requirements are satisfied by the cylindrical bore 1663 rising from the valve seat 1661 which is inclined at a 45° angle with sufficient height to accommodate the full stroke with a diameter that allows maximum flow while centering the poppet stem carrying the O-ring within the conical seat area. The differential diameter between the O-ring gate valve and the diaphragm seal is at least 1 to 2 causing a pressure buildup in the poppet cylinder at the point of opening to back servo the diaphragm seal to allow the poppet to ride against the ascending diaphragm dome. Lateral movement of the O-ring gate is limited by the pilot bore 1663 thereby capturing the valve gate so that it remains in alignment during its stroke.

The amount of O-ring compression has been limited. When the closing servoing pressures exceed 25 psi (which is beyond the normal operating pressure range) the poppet head 1654 reaches the shoulder 1662 which limits further forward travel and further O-ring compression. The travel of the servoing master diaphragm 1631 is limited by progressive diaphragmatic unloading as the semi-circular portion or convolution is flexed. This flexing is limited by the geometry of the bell-shaped chamber 1624.

The present design utilizing the elastomeric graphite filled pads 1651 and 1657 permits the use of a thin low durometer diaphragm seal 1646 to rapidly respond to both mechanical opening and closing pressures under various working conditions while still providing the necessary resistance to abrasion so as to provide a long working life. By keeping the poppet 1652 centered, the friction between the poppet head rim and the walls of the chamber are minimized. The cartridge 1601 makes possible the delivering of pulsatile stroke volumes at a selected opening and closing ratio and time as inlet pressures are increased.

From the arrangement hereinbefore described it can be seen that the poppet 1652 is cellularized in its chamber by a captured diaphragm seal 1646 which in turn is actuated downward by a cam button 1641 under the control of the master servoing diaphragm 1631. While closing is mechanical in nature, opening is caused by a pressure rise in the plenum chamber 1624 acting to cause a yield of all components of elastomeric closing. Piston effects acting upon differential servoing areas balance operations between servoing and valving actions as operational pressures are changed. The flight path of the poppet valve gate captured on the poppet assembly is precisly guided within its valve seat cone by the pilot bore 1663 above the valve seat.

By constructing the cartridge 1601 in the manner hereinbefore described, it has been found that diaphragm seal life has been greatly prolonged. The cartridge can operate at high frequencies with very little noise. Peak flow restrictions are overcome and stalling is inhibited. Pressures ranging from 15 to 100 psi are readily accommodated. Cylic operation from 1 to 1800 cycles per minute could be readily accommodated. Sufficient operational stroke and clearance of the poppet valve is provided to permit back servoing in proportion to outflow within a flow range from 5 to 200 liters per minute. Valve opening and closing is substantially instantaneous to provide maximum flow during the valve open interval. It has been found to be capable of operating for prolonged periods of time at high frequency oscillation without self destructing. Billions of cycles of operation can be performed before overhaul is required Another embodiment of the normally open flow/timing cartridge is shown in FIGS. 39 and 40. As shown therein, the cartridge 1676 consists of a manifold section 1677 and a cartridge section 1678 both of which combined perform the same function as the cartridge 1601. The manifold section 1677 is provided with a cylindrical manifold body 1679 provided with three threaded bores 1681, 1682 and 1683 which are arranged in the same manner as the bores 1606, 1607 and 1608 in the manifold body 1602. They are connected by passages 1684, 1686 and 1687 in the same way that passages 1609, 1611 and 1614 interconnect the bores 1606, 1607 and 1608. The passage 1686 serves as the first passage for the manifold section 1677. In a similar manner, the manifold body 1679 is provided with a threaded bore 1688 which extends into an exteriorly threaded protrusion 689. The bore 1688 is in communication with the passages 1686 and 1687. The manifold body 1679 is also provided with another threaded bore 1691 which is offset longitudinally as well as circumferentially of the bores 1681, 1682 and 1683. The bore 1691 is in communication with a flow passage 1692 which extends at right angles to another flow passage 1693 extending axially of the manifold body 1679. The flow passage 1693 extends through an extension 1694 and serves as a second flow passage for the manifold section 1677. The extension 1694 is provided with a configuration so that it can be utilized with the quick disconnect fittings 1696 of the type hereinbefore described in FIGS. 12 and 13. The fitting 1696 is utilized for interconnecting the two sections 1677 and 1678. Typically, the manifold section 1677 can be mounted on a front panel 1697 and secured thereto by a hexagonal nut 1698. A knob 1699 is provided which adjusts the position of a needle valve 1701 which can be utilized for controlling the flow of gas through the passage 1686.

The cartridge section 1678 is substantially identical to the cartridge body 1606 as are the components which are disposed within the body. The principal difference is that the closure for the master diaphragm 1631 is provided with a circular member 1706 which takes the place of the flange 1604 provided on the manifold body 1602. This member 1706 is provided with an extension 1707 which has a conformation which is adapted for use with a quick disconnect 1696 of the type hereinbefore described so that the extension 1694 receives one end of the quick disconnect connector and the other end receives the extension 1707 carried by the member 1706. The member 1706 is held in place by the C-type lock ring 1628. The extension is provided with a bore 1708 which receives the extension 1694. The extension 1694 carries an O-ring 1709 for forming a gas-tight seal between the extensions 1694 and 1707. The member 1706 is provided with a passage 1711 in communication with the bore 1708. The passage 1711 serves as a second flow passage for the cartridge section 1678.

Operation and use of the cartridge 1676 in FIGS. 39 and 40 is substantially identical to that of the cartridge 1601 with the exception that the cartridge 1678 can be separated from the manifold 1677 when desired merely by pulling the same apart through operation of the quick disconnect fitting 1696 interconnecting the two. Thus it can be seen that if it is desired to change the cartridge section 1678, it is merely necessary to disconnect the tubes which are connected thereto and to pull it apart from the manifold section 1677. Similarly, the cartridge section 1678 can be replaced by inserting it into the quick disconnect fitting 1696 and thereafter connecting the hose or tubing to the cartridge section.

This feature greatly aids interchange of cartridges in that it saves considerable time and also expense. It can be seen that such an arrangement particularly facilitates repairs in the field. It also should be appreciated that the fittings provided in each end of the cartridge section 1678 are such that either end of the cartridge can be secured to the quick disconnect fitting 1696 connected to the manifold section 1677. This makes it possible to utilize the same cartridge section 1678 for performing different functions. When the cartridge section 1678 is mounted in the way shown in FIG. 39, the master diaphragm can be servoed through the manifold. By mounting the cartridge section 1678 in the opposite direction, the master diaphragm can be servoed directly by connecting the outer side of the diaphragm to a source of gas.

In FIG. 41 there is disclosed a cross sectional view of an augmented nebulizer incorporating the present invention and which can be utilized with ventilators or respirators of the type herein described. As shown in FIG. 41, the augmented nebulizer has similarities to the nebulizer hereinbefore described in conjunction with FIGS. 20 and 21. The augmented nebulizer 1726 shown in FIG. 41 consists of a cup-like member or container 727 which is provided with a cylindrical sidewall 1728 and a dished bottom wall 1729. The cup-like member 1727 is adapted to carry a liquid 1730 which is used for forming an aerosol as hereinafter described. The cup-like member 1729 is formed with a depending rim 1731 which has its lower extremity lying in a horizontal plane. The depending rim 1731 is provided with a cutout (not shown) through which a hose or other tubular member (not shown) can extend and be connected to a fitting 1733 formed integral with the bottom wall and having a flow passage 1734 therein extending upwardly into an interior extension 1736 formed integral with the bottom wall 1729. The other components interior of the nebulizer 1726 are very similar to those described in connection with those shown in FIGS. 20 and 21.

A cap or cover 1737 is removably mounted on the upper end of the cup-like container and is adapted to close the same. Means is provided for introducing air into the interior of the container through the cap or cover 1737 and consists of a tee 1738 which is formed integral with the cover 1737. The tee 1738 is provided with inlet ports 1739 which is adapted to be connected to gasses supplied from a volume regulator or from the reservoir of the ventilators hereinbefore described. Another leg of the tee 1738 is provided with a fitting 1740 which is adapted to be connected to a counterpulsing flow of gasses supplied by the ventilators of the type hereinbefore described. In this way it can be seen that gases introduced through the port 1739 and through the fitting 1740 will be introduced through the other leg of the tee into the interior of the cup-like member 1727.

An automatic refill float 1741 is positioned within the cup-like member 1727 and is utilized to ensure that the liquid 1742 provided in the bottom of the cup-like member 1727 remains at a relatively constant level. The liquid is supplied to the cup-like member 1727 through a refill port 1743 carried by the tie 1739. The opening and closing of the port 1743 is controlled by the automatic refill float 1741. A drug injection port 1744 is provided.

The cup-like member 1727 is provided with a large opening or port 1746 in the side wall which is in general alignment with the region in the cup-like member in which the liquid is broken up during the nebulization process. A rigid augmentation tube 1747 has one extremity of the same mounted in the port 1746. The augmentation tube 1747 can be constructed of any suitable material. For reasons hereinafter explained, it has been found to be desirable to form it of a suitable heat conducting material such as copper. The tube is mounted in the port 1746 in such a manner so that it can be readily removed. It has a diameter of approximately ¾ of an inch and has a length of approximately six inches. The nebulizer itself has a diameter of approximately one and one half inches. An annular insert 1748 is provided in the distal extremity of the tube 1747 and serves as an anti-spill ring. As indicated in the drawing, the tube 1747 can be directly connected to the phasitron hereinbefore described.

Operation and use of the augmented nebulizer 1726 shown in FIG. 41 may now be described as follows. Let it be assumed that it is desired to ventilate a patient which requires additional nebulization. Let it also be assumed that the augmented nebulizer 1726 has been properly connected into the respiratory circuitry and to the patient. As soon as the respirator is turned on, respiratory gases under pressure of approximately 40 psi are delivered into the fitting 1733. This air under pressure is introduced upwardly into the nebulizer and causes a suction to be created which brings liquid from the bottom of the cup-like member 1727 into contact with the air flow through the nebulizer from the reservoir of the volume regulator in one direction and counterpulsing flow from the percussionator in the opposite direction. In order to prevent the particles which are formed during the nebulization process from raining out on the side walls of the cup-like container 1727 and in order to increase the nebulized particles in the gas stream supplied to the patient, the augmentation tube 1747 is utilized. The augmentation tube 1747 in connection with the cup-like member 1727 forms one end of a tee which creates a venturi effect to in effect drop the pressure at the entrance to the tee to entrain additional molecules and particles of the liquid in the gas. In previous embodiments, the use of a counterpulse was described. In the present embodiment the counterpulsing flow can be delivered to the nebulizer as shown which can be utilized for providing additional molecules or particles to be entrained in the gas as it passes through the augmentation tube.

The augmentation tube 1747 makes the nebulizer appear to have walls which are spaced apart by a diameter which is equal to the length of the augmentation tube plus the original diameter of the nebulizer. It has been found that by providing the tube, the particles of liquid, rather than impacting on the side walls of the cup-like member 1727, instead rush down thrugh the tube as indicated by the arrows 1751 and would be carried down the tube in a venturi-like fashion and be discharged at the end of the tube into the phasitron or other device utilized in conjunction with the augmented nebulizer. It has been found by the use of the augmentation tube that the output from the augmented nebulizer 1726 can be increased from approximately 60 to 160 milliliters an hour using the same operating pressure of 40 psi.

It should be appreciated that if desired still additional augmentation can be obtained by placing another port in the side wall 180° removed from the port 1746 and another augmentation tube placed in that port to again markedly increase the capacity of the nebulizer in direct proportion to the added length of the augmentation tube.

It can be seen that by using one or more augmentation tubes increased nebulization can be obtained while the actual nebulizer can be kept relatively small in size.

Use of a conductive metal as, for example, copper for the augmentation tube provides several desirable features. For example, it can transfer heat into the air stream passing through the tube or transfer heat out of the air stream. It operates as a heat sink in either case. It has been found that there is a 15° temperature drop in the gases passing through the augmentation tube because of evaporative cooling within the tube. This is particularly true when oxygen is utilized as the gas.

In many cases it is undesirable to deliver gases to the physiological airway of the patient at such a reduced temperature. By utilizing copper tubing, heat is transferred from the ambient atmosphere in the room into the gases passing through the tube. If it is desired to further heat the gases to ensure that the gases will be delivered at a proper temperature to the airway of the patient, a heating coil 1754 can be wrapped around the augmentation tube. Electrical energy can be supplied to the heating coil 1754 from a conventional 110 volt 60 cycle AC source 1756. The energy supplied can be controlled automatically by the use of a potentiometer 1757 controlled by a thermistor 1758 located in a position close to the patient airway to sense the gas temperature. In this way the temperature increase is controlled so that the gas is delivered to the patient airway at approximately 37° C.

An enhancement circuit for use in the circuitry shown in FIG. 26 is shown in FIG. 42. As shown in FIG. 42, the enhancement circuit involves the interruption interval cartridge 1283 that is provided with a valve member 1286 that is actuated by the diaphragm 1284. The diaphragm 1284 is operated from a servo port 1282. The inlet of the interruption interval cartridge 1283 is supplied with gas through the oscillatory CPAP/PEEP needle valve 1351. An adjustable needle valve 1769 is provided as a part of the enhancement circuit shown in FIG. 42 and is connected between the outlet and the inlet of the interruption interval cartridge 1283.

As disclosed previously, the ventilator is shown in FIG. 26 prior to the modification which is disclosed in FIG. 42 when the master on/off switch 1222 is turned on, gas is supplied through the oscillatory CPAP/PEEP valve 1351 which meters gas through the normally open interruption interval cartridge 1283 and then up through the normally open parallel oscillator cartridge 1321 which is being opened and closed by the timing circuit hereinbefore described 180° out of phase with or inverse to the opening and closing of the primary oscillator cartridge 1312. The amplitude or volume flow of the gas to the phasitron 1036 is controlled by the needle valve 1351. The interruption interval cartridge 1283 opens and closes every time the time cycled parallel oscillator cartridge 1321 opens and closes. Every time interruption interval cartridge 1283 closes, gas cannot flow from the master on-off switch 1222 through the oscillatory C-PAP/PEEP needle valve 1351 which controls the flow to the parallel oscillator cartridge 1321. When this flow is stopped, the counterpulses hereinbefore described are still provided to the swivel tee 1421 to provide diffusion. Thus there is provided a small amount of flow to the patient coming through the swivel tee 1421. During the time that flow is interrupted by the interruption interval cartridge 1283, the pressure in the patient airway will be at a base line or at a static constant positive airway pressure (CPAP).

The enhancement metering needle valve 1769 which is provided in FIG. 42 when added to the circuitry shown in FIG. 26 serves to bypass the interruption interval cartridge 1283 and supplies gas from the oscillatory CPAP/PEEP needle valve 1351 to the parallel oscillator cartridge 1331. This causes gas to be delivered to the phasitron 1036. This gas flow is interrupted periodically by the oscillations of the parallel oscillator cartridge 1331 so that there is provided a base line oscillation of adjustable magnitude as adjusted by the opening of the enhancement metering valve 1769 to provide what can be called oscillatory demand CPAP or OD CPAP.

In FIGS. 43 and 44 there are shown graphs of two different wave forms which can be provided with such a ventilator utilizing OD CPAP. In FIG. 43 there is shown a wave form 1771 which is provided with oscillatory base line portions 1771a, and oscillatory rising portions 1771b and falling portions 1771c. The wave form in FIG. 43 should be compared with the wave form which is shown in FIG. 33. In FIG. 33 it can be seen that there is an ascending portion 1556a in which the pulses increase progressively as the lung is inflated until the peak pressure is reached after which the lung is deflated through the curve 1556b to a flat base line portion 1556c. On the other hand, as shown in FIG. 43, by utilizing the enhancement metering needle valve 1769 hereinbefore described, there is provided a flat base line portion 1771a, on which there are superimposed oscillations or stroke volumes of generally the same amplitude. On the ascending wave form portion 1771b, the stroke volumes or pulses are at their maximums and these are gradually decreased as the lung is inflated until they reach a minimum after which the lung is deflated as in the wave form portion 1771c returning to the oscillatory base line portion 1771a. The rate of decrease of amplitude of the oscillatory pulses or stroke volumes is determined by the rate of opening of the interrupter cartridge. Thus the faster the opening the more rapidly the amplitude of the stroke volumes decrease. By utilizing such decreasing stroke volumes as the lung is inflated, it has been found that the hoop stress which is created during use of the ventilator on the lung is greatly reduced. This is particularly important for use in situations where the patient has a very stiff lung which also often can be what is characterized as a "tissue paper" lung which is readily torn. By utilizing a procedure such as represented by the wave form 1771 in which smaller stroke volumes are applied as the lung is inflated, much less hoop stress is generated and therefore there is much lesser tendency of pneumothoracy. In the wave form 1772 shown in FIG. 44 there is also provided oscillatory base line portions 1772a, rising portions 1772b and falling portions 1772c. However, the wave form has almost a sinusoidal characteristic which makes it particularly useful on applications ranging from neonatal to adult patients. To produce a wave form such as shown in FIG. 44, the flow to the diaphragm 1284 of the interruption interval cartridge 1283 is controlled so that it opens very slowly, as for example, over a period of approximately 2 seconds. It can be seen that the slower the interruption interval cartridge opens the more time there is for gas to flow through the enhancement metering valve 1769. Therefore it can be seen that the amplitude of the oscillations provided by the enhancement metering valve 1769 gradually increase as the opening time for the interruption interval cartridge 1283 is increased. As this gradual opening occurs, the base line of the wave form 1772 is gradually raised in a very smooth transition as shown in FIG. 44. The amplitude of the oscillations decreases slightly as the lung is inflated. When the peak inflation is reached, the wave form again drops down to the base line in the portion 1772c. However, again it can be seen that the drop to the base line is relatively gradual. By using such a wave form, it can be seen that a very gentle type of ventilation is provided to the lungs of the patient.

By utilization of the enhancement circuit which is shown in FIG. 42, it can be seen that it is possible to still utilize CPAP to cause blood to flow from the right side of the heart through the lungs to the left side of the heart without reducing the cardiac output. This is made possible because oscillations are provided at all times on the wave form during inhalation and exhalation of the patient. Thus it can be seen that blood is actually pumped from the right side of the heart to the left side of the heart. This provides for vesicular peristalsis in terms of pulmonary and systemic blood flow as well as enhancing cardiac output during mechanical ventilation of the lungs of a patient.

It should be appreciated that if it is desired to obtain a wave form which is still much more sinusoidal than that which is shown in FIG. 44 it is possible to obtain such a wave form by introducing a ramping orifice of a suitable size, as for example, 0.024 inches (not shown) in the servo port to the interruption interval cartridge 1283. Such a ramping orifice allows a more gradual opening and closing of the interruption interval cartridge 1283 with a net result of causing a slow start for oscillation as well as a slow oscillatory return to the base line and thereby providing a much truer sinusoidal pattern when OD-CAP is employed. Significantly, the ramping effect at the start of the oscillation greatly reduces hoop stress within the physiological airways further minimizing tendencies toward baro-trauma.

In FIG. 45 there is shown a partial schematic view of the primary oscillator cartridge 1312 which is shown in the ventilator in FIG. 26 and the manner in which the loading valve 1337 as been repositioned to achieve stability for the ventilator at different altitudes. In the embodiment shown in FIG. 26 it was found that the gases leaving the loading or check valve 1337 in the position shown in FIG. 26 that compression occurring with increasing altitude created turbulence. This required a more competent check valve with a higher opening pressure to obtain stability which in turn decreased peak oscillatory frequencies. Since this was undesirable, it was found that these deficiences could be overcome by shifting the check valve or loading valve 1337 from where it was immediately adjacent the outlet 13 to a position at which it is opposite the outlet 1339 or on the opposite side of the needle valve 1338. By making this change of position, it has been found that the ventilator now produces a remarkably stable pulsation over the entire frequency range at various altitudes. Turbulence has been eliminated by using a check valve of the type described in FIGS. 35 and 36.

It should be appreciated that as another embodiment of the ventilator herein disclosed, the check valve or the loading valve provided on the outlet of the oscillator cartridge can also be shifted so that it is positioned after the needle valve in the timing circuit. Thus, for example, in the ventilator shown in FIG. 18, the check valve 1067 can be shifted into a position so that it immediately follows the outlet 1071 from the impact metering cartridge 1069. By making such a rearrangement, there is a more effective timing circuit unloading. The stroke volume at all frequencies is improved With such a rearrangement it has been found that a stable operation can be achieved down to 10 psi operating pressure.

In FIG. 26 as hereinbefore explained, an accessory pressure limiting regulator 1336 is provided which is connected to the phasitron socket 1033. When the predetermined pressure is reached, the socket 1033 is vented to ambient. Such pressure limiting means is not particularly effective in limiting the pressure rise in time cycled pressure variable ventilators. Rather than using a pressure limiting regulator 1366 in the manner indicated in FIG. 26, it has been found to be preferable with respect to time cycled pressure variable ventilators to use such a device. The device has its output connected to the phasitron socket 1033 and its input connected through a one-way valve to the servo port of the normally open oscillator cartridge 1312. When the relieving pressure of the pressure limiting regulator is reached, the gas volume released serves to charge the pulsatile timing circuit and thereby causes early termination of the timed pulse opening by decreasing the pulse generator valve opening time. The tidal volume delivery is limited resulting in a servoed form of peak pressure limiting. In this way it is possible to provide pressure limiting during the delivery of large tidal volumes under high peak pressures and/or during ambient density change (altitude) with inspiratory times of over 1.5 seconds without effecting stroke delivery with inspiratory time of under 0.5 seconds. It has been found this has been a particularly efficacious way to minimize the tendency of a time-cycled pressure variable ventilator to increase tidal volume delivery during an ascent to a higher altitude secondary to an increase in operational pressure.

In FIG. 46, there is disclosed mode switching circuitry which can be utilized with ventilators of the present invention and in particular a ventilator of the type described in FIG. 18 which has a capability of mode selection between intermittent mandatory ventilation and intermittent percussive ventilation, IMV-IPV. The components which are schematically illustrated in FIG. 46 are given the same identification as they were in the embodiment of the ventilator shown in FIG. 23. An additional CPAP isolation check valve 1781 has been provided which is in series with the demand CPAP cartridge 1174 and the phasitron 1036. In order to make two way mode selection possible, a two-way mode selector 1782 has been provided. As can be seen, the mode selector 1782 is connected between the port of the reset cartridge 1044 and the phasitron 1036 and alternatively with the IMV timing circuit dump orifice 1184.

The two-way mode selector 1782 makes it possible to select between IPV or IMV functions allowing isolation of demand CPAP during IPV functions. When IPV functions are selected, all demand CPAP functions, whether "on"[or "off" are isolated from phasic ventilation. Selection of the IMV mode allows the combined use of phasic ventilation and CPAP/PEEP as long as the CPAP/PEEP is of less magnitude than the phasic delivery of tidal volumes.

The penalty for use of the circuit shown in FIG. 46 is minimal. However, there is a slight gas leak from the IMV timing circuit dump orifice 1184 which is of 0.018 size during the delivery of either a stroke or tidal volume. This gas delivery is necessary as entrainment gas during IMV functions when demand CPAP/PEEP is not employed. During IPV usage, the mandated leak would reduce transport time on a cylinder of gas by approximately five minutes.

The two-way valve 1184 is connected so that its common port delivers gas to the inlet of the phasitron 1036 with inlet ports selecting either the IMV segment which is downstream of the timing circuit isolation check valve 1051 or IMV with timing circuit isolation or IPV by selecting the outlet flow from the oscillator cartridge 1038 flowing against the IMV timing circuit dump orifice which dumps to ambient through either the reservoir or the remote switch of the ventilator.

The timing circuit CPAP/PEEP isolation during IMV functions while employing the mandated dump orifice with selectable IPV without employing the 0.018 timing circuit dump orifice 1184 is made possible by an alteration of the flow direction through the two-way pneumatic valve 1784. This requires the common port of the pneumatic valve to accept flow from the oscillator cartridge 1038 outlet with selectable delivery into either the phasitron inlet port for IPV (without isolation) or the inlet of the 0.018 orifice 1184 to ambient (with isolation) for IMV. Should demand CPAP be selected during IPV isolations with a pressure rise above that programmed for phasic ventilation, the phasic ventilation would be muted. Therefore the clinician would not program IMV and demand CPAP as concommitant functions. Such a circuit would allow the separate use of either IPV or demand CPAP for weaning. In addition there is a maximum conservation of medical gases during IPV functions. From the foregoing it can be seen that there have been provided a number of embodiments of ventilators incorporating the present invention utilizing oscillators which have produced pulsatile gases which are supplied to the airway of the patient and which can be impressed upon a constant positive airway pressure. The pulsatile gases can be supplied under manual control to the patient airway or alternatively can be supplied with automatic timing or phasing. In addition, tidal volumes can be manually or automatically superimposed upon the pulsatile gases supplied to the patient or alternatively pulsatile gases can be interrupted during the time that the tidal volumes are being delivered to the airway of the patient. Particularly novel oscillator circuits are provided for delivering the pulsatile gases to the airway of the patient. In addition, a particularly novel nebulizer has been provided for use in the breathing circuit. Also, a particularly novel venturi jet and exhalation valve assembly has been provided which makes possible high frequency phase oscillation. The oscillators are constructed in modular form so that ventilators having various capabilities can be provided with a minimum amount of changes. The ventilators of the present invention make it possible to supply percussive pulsatile gases to the physiological and cardiopulmonary structures of the patient to maintain maximum blood/gas interface and cardiac output while mobilizing intrasecretions with minimal tendency toward pulmonary barotrauma. The pulsatile gases can be supplied to the airway of the patient with a programmable amplitude to produce the desired intrapulmonary mechanical mixing in the patient airway. At least certain of the ventilators of the present invention can be operated to meet the lung size requirements of the mammalian patient by increasing or decreasing source pressures as for example 25 psi for neonates, 35 psi for pediatrics and 50 psi for adults. As the source of pressure is reduced, the frequency range is increased thereby maintaining optimal clinical parameters of both frequency and pressure rise for the mammal being treated. Alarm and failsafe functions are provided in the ventilators in the event that programmed mean airway pressures are exceeded. In the event of explosive decompression, oxygen enrichment is provided while at the same time providing venting to the atmosphere and maintaining a constant positive airway pressure for the patient.

In addition, from the foregoing, it can be seen that there has been provided a ventilator which makes possible volumetric diffusion respiration, oscillatory demand CPAP, intermittent percussive ventilation and routine ventilatory procedures along with mechanical assist-/control and spontaneous respiratory combinations in all mammalian lungs. The particular exhalation valve assembly utilized makes it possible to work with gas pressure substantially below the conventional 50 psi required as, for example, as low as 20 psi.

Also, from the foregoing it can be seen that there has been provided a ventilator in FIGS. 25 through 31 which has many desirable features. It is possible to provide ventilation ranging all the way from neonates to giants. Control is provided over inspiratory time, expiratory time, inspiratory flow rate, demand CPAP/PEEP and aerosal generation. Negative and positive IE ratios can be programmed. Inspiratory times can range from 0.03 to 3 seconds with expiratory times ranging from 0.3 to off. Inspiratory flow rates can be varied from off to 100 liters per minute to ambient. Demand CPAP/PEEP can be selected from off to 30 centimeters of $H_2O$ with programming to 60 centimeters of $H_2O$ in reserve. Flow generation pressure is selectable from off to source pressure. Time cycled expiratory/inspiratory intervals can be provided.

In addition, full intermittent mandatory ventilation at all demand CPAP values to 30 centimeters of $H_2O$ can be provided. Ventilatory frequencies with selectable IE ratios from to 150 to 600 cycles per minute can be obtained. Intrapulmonary percussive ventilation for endobronchial secretion control to 150 cycles per minute can be obtained.

The ventilator has been provided with a modular construction with coded quick disconnect assemblies which facilitate use and servicing of the ventilator.

What is claimed is:

1. In a ventilator for use with a source of gas under pressure for supplying such gas to the airway of a patient, an inlet adapted to be connected to the source of gas, an outlet adapted to be connected to the airway of the patient, oscillator means having an inlet and an outlet, means coupling the inlet of the oscillator means to the inlet of the ventilator, and means coupling the outlet of the oscillator to the outlet of the ventilator and pneumatic control means coupled to the inlet of the ventilator and coupled to said oscillator means causing said oscillator means to supply successive small volumes of gas through the outlet of the oscillator means and the outlet of the ventilator to the airway of the patient to cause diffusive ventilation of the lungs of the patient, said pneumatic control means operating solely under pneumatic control, said oscillator means including a body having the inlet and the outlet, a flow passage interconnecting the inlet and outlet of the body, a valve seat encircling the flow passage, a valve member mounted in the body in the flow passage and being movable between open and closed positions with respect to the valve seat to control the flow of gas through the flow passage from the inlet to the outlet of the body, diaphragm means carried by the body for moving the valve member between said open and closed positions, said valve member being disposed on one side of the diaphragm means, a servo port mounted on the body on the other side of the diaphragm means, means connecting the outlet of the body to the servo port for supplying gas to one side of the diaphragm means for moving the diaphragm means to cause movement of the valve member to one of said open and closed positions, said means connecting the outlet of the oscillator means to the servo port including adjustable metering valve means for controlling the rate of flow of gas into and out of the servo port to thereby control the rate of oscillation of the oscillation means and thereby the frequency rate the successive small volumes of gas supplied to the outlet of the ventilator.

2. A ventilator as in claim 1 wherein said means coupled to the outlet includes pneumatic clutching means coupled to the outlet of the ventilator permitting the patient to exhale during the time that the successive small volumes of gas are being delivered to the outlet of the ventilator for delivery to the airway of the patient.

3. A ventilator as in claim 1 wherein said pneumatic control means includes timing means for controlling the timing of the supplying of successive small volumes of gas to the airway whereby the length of the inspiratory and expiratory phases of the ventilator can be controlled.

4. A ventilator as in claim 1 wherein said pneumatic control means includes valve means for enhancing the stroke volume of the oscillator means and thereby the amplitude of the successive small volumes of gas supplied to the outlet of the ventilator.

5. A ventilator as in claim 1 wherein said pneumatic control means includes master timing means for providing time cycled ventilation, said master timing means including oscillator timing reset means, said oscillator timing reset means including a body having the inlet and the outlet, a flow passage interconnecting the inlet and the outlet, a valve seat encircling the flow passage, a valve member mounted in the body movable between open and closed positions with respect to the valve seat to control the flow of gas from the inlet to the outlet, diaphragm means carried by the body for moving the valve member between said open and closed positions, a servo port mounted on the body for supplying gas to one side of the diaphragm means for moving the valve member to one of said open and closed positions, metering valve means coupled to the servo port of the oscillator timing reset means, means coupling the inlet of the oscillator timing reset means to the inlet of the ventilator and means coupling the outlet of the oscillator timing reset means to the outlet of the oscillator means for controlling the flow of successive small volumes of gas from the outlet of the oscillator means to the outlet of the ventilator.

6. A ventilator as in claim 5 wherein said means coupling the outlet of the oscillator timing reset means includes a manually operated valve.

7. A ventilator as in claim 6 together with volumetric ventilator means having an inspiratory phase and an expiratory phase in its operational cycle and means connecting the volumetric ventilator means to the outlet of the ventilator and to the outlet of the oscillator means and means for alternatively selecting time cycled ventilation provided by the master timing means and volume cycled ventilation provided by the volumetric ventilation means.

8. A ventilator as in claim 1 wherein said pneumatic control means includes master timing means, said master timing means including timing means, said timing means including a body having the inlet and the outlet and a flow passage establishing communication between the inlet and the outlet, a valve seat encircling the flow passage, a valve member carried by the body movable between open and closed positions with respect to the valve seat to control the flow of gas through the flow passage, a diaphragm carried by the body and connected to the valve member for moving the valve member to the closed position, a servo port carried by the body for supplying gases to the diaphragm to move the diaphragm to move the valve member to a closed position, means connecting the inlet of the timing means to the inlet of the ventilator, said master timing means also including oscillator timing reset means, said oscillator timing reset means including a body having the inlet and the outlet, a flow passage connecting the inlet and the outlet, a valve seat encircling the flow passage, a valve member movable between open and closed positions with respect to the valve seat to control the flow of gas through the last named flow passage, diaphragm means carried by the body form forming the valve member to a closed position and a servo port carried by the body for supplying gas to the diaphragm means to move the valve member to the closed position, metering valve means connected to the outlet of the timing means and connected to the servo port of the timing means, means connecting the outlet of the timing means to the servo port of the oscillator timing reset means, adjustable metering valve means connected between the inlet of the oscillator timing reset means and the servo port of the timing means and means connected to the outlet of the oscillator timing reset means and coupled to the outlet of the ventilator so that gas can be discharged therefrom.

9. A ventilator as in claim 8 wherein said master timing means includes a timing reservoir connected between the adjustable metering means connected to the inlet of the oscillator timing reset means and the servo port of the timing means.

10. A ventilator as in claim 1 wherein said means coupling the outlet of the oscillator means to the outlet of the ventilator includes an encapsulated venturi coupled to the outlet of the oscillator means, and an exhalation valve mounted on the encapsulated venturi and coupled to the outlet of the oscillator means.

11. A ventilator as in claim 10 wherein said encapsulated venturi includes a body having a venturi-like passage therein coupled to the outlet of the ventilator, an additional body encapsulating said first-named body and providing a circumferential space therebetween, means coupled to the outlet of the oscillator means for supplying a jet of gas through the venturi and nebulizer means connected to the encapsulated venturi and being in communication with the circumferential space surrounding the first-named body of the encapsulated venturi.

12. A ventilator as in claim 11 wherein said nebulizer means includes a cylindrical member, a reservoir cup supported by the cylindrical member adapted to carry medication, wall-like means carried by the cylindrical member and having a hollow cylindrical tube extending axially of the cylindrical member and downwardly into the reservoir cup, a capillary tube extending through the hollow cylindrical tube and into the reservoir cup and having an outlet end, means in the cylindrical member forming a venturi-like passageway in communication with the outlet end of the capillary tube, a nozzle carried by the cylindrical member and coupled to the inlet of the ventilator for supplying a jet of gas to the venturi-like passageway to cause liquid to be drawn up through the capillary tube and to be formed into an aerosol and to be supplied to the circumferential space.

13. In a ventilator for use with a source of gas under pressure for supplying gas under pressure to the airway of a patient, an inlet adapted to be connected to the source of gas under pressure, an outlet adapted to be connected to the airway of the patient, oscillator means, timing reset means, said oscillator means and said timing reset means each having a body provided with an inlet and an outlet and a flow passage establishing communication between the inlet and the outlet of the body, a valve seat encircling the flow passage, a valve member disposed in the flow passage and movable between open and closed positions with respect to the valve seat for controlling the flow of gas from the inlet to the outlet of the body, a diaphragm coupled to the valve member, a servo port for supplying gas to the diaphragm to move the valve member to one of said open or closed positions, said valve member being disposed on one side of the diaphragm and said servo port being disposed on the other side of the diaphragm, means connecting the inlet of the oscillator means to the inlet of the ventilator, combination venturi jet and exhalation valve means having a body with an inlet and an outlet and a flow passage extending therebetween, means connecting the outlet of the combination venturi jet and exhalation valve means to the outlet of the ventilator, a nebulizer having an inlet and an outlet, means coupling the outlet of the nebulizer to the body of the combination venturi jet and exhalation valve means so that the outlet of the nebulizer is in communication with the flow passage in the body, means coupling the outlet of the oscillator means to the servo port of the timing reset means and to the inlet of the combination venturi jet and exhalation valve means, the application of gas from the outlet of the oscillator means to the timing reset means causing the valve member of the timing reset means to be moved to a closed position to occlude the flow of gas from the inlet to the outlet of the timing reset means, adjustable impact metering means having an inlet and an outlet, means connecting the outlet of the oscillator means to the inlet of the adjustable impact metering means, adjustable frequency metering means having an inlet and an outlet, means connecting the inlet of the timing reset means to the outlet of the frequency metering means, means connecting the outlet of the impact metering means to the servo port of the oscillator means and to the inlet of the frequency metering means whereby when said timing reset means is in a closed position, gas is supplied to the servo port of the oscillator means to move the diaphragm and the valve member actuated thereby to a closed position to occlude the flow of gas from the inlet to the outlet of the oscillator means, the rate of movement of the valve member of the oscillator means to the closed position being determined by the rate of flow of gas through the frequency metering means, the closing of the valve of the oscillator means permitting gases behind the diaphragm of the reset means to be bled to ambient through the combination venturi jet and exhalation valve means whereby the timing reset means moves to a closed position from a normally open position permitting gas behind the diaphragm of the oscillator means to be bled out through the frequency metering means and through the inlet and the outlet of the timing reset means and means connected to the inlet of the ventilator and to be nebulizer for supplying gas to the nebulizer so that aerosoled gases can be supplied from the nebulizer to the combination venturi jet and exhalation valve means.

14. A ventilator as in claim 13 together with manual push button means connected to the inlet of the ventilator and to the inlet of the combination venturi jet and exhalation valve means for controlling the supply of gases to the patient.

15. A ventilator as in claim 13 wherein said means connecting the outlet of the oscillator means to the timing reset means and to the combination venturi jet and exhalation valve means includes a flow obtunder, said flow obtunder including a body having a chamber therein and an outlet in communication with the chamber, a protrusion secured to the body and extending into the chamber, said protrusion having an inlet and a flow passage therein in communication with the inlet and opening into the chamber and a resilient sleeve mounted on said protrusion and occluding the opening of said flow passage into the chamber, said sleeve being expandable to permit flow of gas from the flow passage into the chamber and out through the outlet of the flow obtunder.

16. A ventilator as in claim 13 together with a constant positive airway pressure means having an inlet and an outlet, a flow passage interconnecting the inlet and the outlet, a valve seat encircling the flow passage, a valve member movable between open and closed positions with respect to the valve seat for controlling the flow from the inlet to the outlet, a diaphragm coupled to the valve member, a servo port, means connecting the servo port to the outlet of the ventilator, means coupling the inlet of the constant positive airway pressure means to the inlet of the ventilator, means connecting the outlet of the constant positive airway pressure means to the combination venturi jet and exhalation valve means to provide constant positive airway pressure while the ventilator is time cycling.

17. A ventilator as in claim 16 together with a flow obtunder connected between the servo port of the reset means and the inlet of the combination venturi jet and exhalation valve means.

18. A ventilator as in claim 17 together with a one-way check valve means connected between the servo port of the reset means and the flow obtunder.

19. A ventilator as in claim 16 together with adjustable valve means for controlling the flow of gas to the airway of the patient.

20. A ventilator as in claim 19 together with a flow obtunder connected between the servo port of the reset means and the adjustable valve means.

21. A ventilator as in claim 13 wherein said means connecting the outlet of the oscillator means to the servo port of the reset means includes one-way check valve means.

22. A ventilator as in claim 13 wherein said means connecting the outlet of the oscillator means to the inlet of the impact metering means includes one-way check valve means.

23. A ventilator as in claim 13 wherein said means connecting the outlet of the impact metering means to the servo port of the oscillator means and to the inlet of the frequency metering means includes a one-way check valve.

24. A ventilator as in claim 13 together with a flow restricting orifice connected between the servo port of the reset means and the outlet port of the reset means.

25. A ventilator as in claim 13 together with mode selection means connected between the servo port of the timing reset means and the combination venturi jet and exhalation valve means for selecting either IPV or IMV ventilation.

26. A ventilator as in claim 13 together with pressure limiting regulator means having an input and an output, means connecting the input to the servo port of the oscillation means and means connecting the outlet to the combination venturi and exhalation valve means.

27. In a ventilator for use with a source of gas under pressure for supplying gas under pressure to the airway of a patient, an inlet adapted to be connected to the source of gas under pressure, an outlet adapted to be connected to the airway of the patient, primary oscillator means and counterpulse oscillator means, said primary and counterpulse oscillator means each having an inlet end and an outlet and a flow passage establishing communication between the inlet and the outlet, a valve seat through which the flow passage extends, a valve member movable between open and closed positions with respect to the valve seat for controlling the flow of gas from the inlet to the outlet, a diaphragm coupled to the valve member for actuating the valve member, means forming a servo port for supplying gas to one side of the diaphragm, the valve seat member being disposed on one side of the diaphragm and the means forming a servo port being disposed on the other side of the diaphragm, means for supplying gas from the inlet of the ventilator to the inlet of the primary oscillator means, means for supplying gas from the outlet of the primary oscillator means to the means forming a servo port of the counterpulse oscillator means, means including adjustable valve means for supplying gas from the inlet of the ventilator to the means forming a servo port of the primary oscillator means, timing means coupled between the outlet of the primary oscillator means and the means forming a servo port of the primary oscillator means and causing said primary oscillator means and said counterpulse oscillator means to operate out of phase with each other, and means connecting the outlets of the primary oscillator means and the counterpulse oscillator means to the outlet of the ventilator whereby pulses of gas are supplied to the patient by the primary oscillator means and the counterpulse oscillator means which are out of phase with each other.

28. A ventilator as in claim 27 wherein said timing means including first and second needle valve means each having an inlet and an outlet, means connecting the outlet of the primary oscillator means to the inlet of the first needle valve means, means connecting the outlet of the first needle valve means to the means forming a servo port of the primary oscillator means, oscillator reset means having an inlet, an outlet and means forming a servo port, means connecting the inlet of the ventilator to the means forming a servo port of the oscillator reset means, means connecting the outlet of the first needle valve means to the inlet of the oscillator reset means, means connecting the means forming a servo port of the oscillator reset means to the inlet of a second needle valve means, a frequency rate adjust needle valve assembly having an inlet and an outlet, means connecting the outlet of the second needle valve means to the inlet of the frequency rate adjust needle valve assembly and means coupling the outlet of the frequency rate adjust needle valve assembly to the outlet of the ventilator.

29. In a ventilator for use with a source of gas under pressure for supplying gas under pressure to the airway of a patient, an inlet adapted to be connected to the source of gas under pressure, an outlet to be adapted to connected to the airway of the patient, primary oscillator means, oscillator reset means, counterpulse oscillator means, interruption interval means, inspiratory means, inspiratory reset means, transition delay means, each of said primary oscillator means, oscillator reset means, counterpulse oscillator means, interruption interval means, inspiratory means, inspiratory reset means and transition delay means including a body having an inlet and an outlet and a flow passage establishing communication between the inlet and the outlet of the body, a valve seat encircling the flow passage, a valve member movable between open and closed positions with respect to the valve seat for controlling the flow of gas from the inlet to the outlet of the body, a diaphragm coupled to the valve member, a servo port for supplying gas to the discharge to move the valve member to one of said open and closed positions, said valve member being disposed on one side of the diaphragm and said servo port being disposed on the other side of the diaphragm, means connecting the inlet of the primary oscillator means and the inspiratory means to the inlet of the ventilator, means including adjustable needle valve means for connecting the inlet of the interruption interval means to the inlet of the ventilator, combination venturi jet and exhalation valve means having an inlet an outlet with the outlet being coupled to the outlet of the ventilator, a nebulizer having an inlet and an outlet, means connecting the inlet of the nebulizer to the outlet of the ventilator, means connecting the outlet of the nebulizer to the combination venturi jet and exhalation valve means, means including an adjustable needle valve means connecting the outlet of the inspiratory means to the servo port of the transition delay means, means connecting the outlet of the inspiratory means to the servo port of the inspiratory reset means, the outlet of the inspiratory reset means being vented to ambient, means including needle valve means connecting the inlet of the inspiratory reset means to the servo port of the inspiratory means, means including adjustable needle valve means connecting the servo port of the inspiratory means to the outlet of the transition delay means, coupling means including an interruption interval pressure rise needle valve means connecting the outlet of the transition delay means to the inlet of the combination venturi jet and exhalation valve vase to provide pulses of gas to the airway of the patient, means connecting the inlet of the transition delay means to the servo port of the inspiratory reset means, means connecting the outlet of the inspiratory means to the servo port of the interruption interval means, base lines pause needle valve means connecting the outlet of the inspiratory means to the servo port of the inspiratory reset means, means connecting the outlet of the primary oscillator means to the servo port of the oscillator reset means, means including adjustment valve means connecting the outlet of the primary oscillator means to the servo port of the primary oscillator means, the outlet port of the oscillator reset means being open to ambient, means connecting the inlet of the oscillator reset means to the servo port of the primary oscillator means, and means connecting the outlet of the primary oscillator means to the combination venturi jet and exhalation valve means to provide counterpulses of gas to the airway of the patient.

30. A ventilator as in claim 29 together with fail-safe sensitivity means and fail-safe means, said fail-safe sensitivity means and said fail-safe means each including a body provided with an inlet and an outlet and a flow passage establishing communication between the inlet and the outlet of the body, a valve member movable between open and closed positions for controlling the flow of gas from the inlet to the outlet of the body, a diaphragm coupled to the valve member and a servo port for supplying gas to the diaphragm to move the valve member to a closed position, means connecting the outlet of the primary oscillator means to the inlet of the fail-safe sensitivity means, means connecting the outlet of the primary oscillator means to the servo port of the fail-safe sensitivity means including adjustable needle valve means, means connecting the outlet of the fail-safe sensitivity means to the servo port of the fail-safe means, means connecting the outlet of the primary oscillator means to the inlet of the fail-safe means and alarm means connected to the outlet of the fail-safe means.

31. In a ventilator for use with a source of gas under pressure for supplying gas under pressure to the airway of a patient, an inlet adapted to be connected to the source of gas under pressure and an outlet adapted to be coupled to the airway of the patient, combination venturi jet and exhalation valve means having an inlet and an outlet with the outlet being connected to the outlet of the ventilator, timed cycled pneumatically controlled ventilation means connected to the inlet of the ventilator adapted to be connected to the source of gas under pressure for supplying gas to the inlet of the combination venturi jet and exhalation valve means, diffusive high frequency ventilation means connected to the inlet of the ventilator adapted to be connected to the source of gas under pressure and connected to the inlet of the combination venturi jet and exhalation valve means for supplying pulses of gas under high frequency, and means for selecting alternatively time cycled and diffusive high frequency ventilation for the patient.

32. A ventilator as in claim 31 wherein the high frequency diffusive ventilation means includes means for supplying counterpulses of gas to the combination venturi jet and exhalation valve means which are out of phase with the first named pulses supplied by the high frequency diffusive ventilation means.

33. In a ventilator for use with a source of gas under pressure for supplying gas under pressure to the airway of a patient during the inspiratory phase, an inlet adapted to be connected to the source of gas under pressure, an outlet adapted to be connected to the airway of the patient, a normally open interruption interval cartridge having an inlet and an outlet, valve means connected to the inlet of the ventilator for supplying gas to the inlet of the interruption interval cartridge, an oscillator cartridge having an inlet and an outlet and valve means for controlling the flow of gas from the inlet to the outlet, means connecting the outlet of the interruption interval cartridge to the inlet of the oscillator cartridge, timing means for opening and closing the valve means of the oscillator cartridge, means for controlling the operation of the interruption interval cartridge, means connecting the outlet of the oscillator cartridge to the outlet of the ventilator, and enhancement circuit means including a needle valve for bypassing the interruption interval cartridge to supply a controlled amount of gas to the inlet of the oscillator cartridge whereby pulses of gas are produced and supplied to the patient by the oscillator cartridge.

34. A ventilator as in claim 33 together with means for controlling the speed of the opening and closing of the interruption interval cartridge so as to change the rapidity at which the lung of the patient is inflated, said change in the speed of opening of the interruption interval cartridge creating a change in the amplitude of the pulses supplied during the inspiratory phase.

35. A ventilator as in claim 33 including means for providing a constant positive airway pressure upon which there is superimposed the pulses of gas.

* * * * *